United States Patent [19]

Oshiro et al.

[11] Patent Number: 5,017,724
[45] Date of Patent: May 21, 1991

[54] HYDROFLUORENE DERIVATIVES

[75] Inventors: Yasuo Oshiro; Tatsuyoshi Tanaka; Yoji Sakurai; Seiji Sato, all of Tokushima, Japan

[73] Assignee: Otsuka Pharmaceutical Co., Ltd., Tokyo, Japan

[21] Appl. No.: 532,341

[22] Filed: Jun. 4, 1990

Related U.S. Application Data

[63] Continuation of Ser. No. 116,698, Nov. 4, 1987, abandoned.

[30] Foreign Application Priority Data

Nov. 4, 1986 [JP] Japan ................................ 61-263561

[51] Int. Cl.$^5$ ............................................ C07C 211/42
[52] U.S. Cl. ................................................... 564/427
[58] Field of Search ......................................... 564/427

[56] References Cited

U.S. PATENT DOCUMENTS

| | | | |
|---|---|---|---|
| 3,010,972 | 11/1961 | Kaiser et al. | 564/427 X |
| 3,159,677 | 12/1964 | Godefroi | 564/427 X |
| 3,553,267 | 1/1971 | Ward | 564/427 |
| 4,113,726 | 9/1978 | Hauck et al. | 564/427 X |
| 4,788,130 | 11/1988 | Oshiro et al. | 514/661 |
| 4,792,628 | 12/1988 | Oshiro et al. | 564/428 |

Primary Examiner—Richard L. Raymond
Assistant Examiner—Brian Bembenick
Attorney, Agent, or Firm—Finnegan, Henderson, Farabow, Garrett & Dunner

[57] ABSTRACT

Novel hydrofluorene derivatives and salts thereof represented by the formula (1) which possess excellent activities for improving anoxemic and hypoxic symptoms and syndromes accompanied therewith, therefore said derivatives are useful as cerebral activators, preventive agents for arrhythmia and heart failure caused by the shortage of oxygen and others. Furthermore, said hydrofluorene derivatives and salts thereof possess actions for scavenging active oxygen radicals, therefore, the derivatives are useful prophylactic and treating agents for various disturbances and diseases caused by the excessive formation of active oxygen radicals. In addition to the above, the hydrofluorene derivatives are useful as anti-oxidative agents for fats and oils.

Yet, further, the hydrofluorene derivatives and salts thereof accelerate the uptaking of high-affinity choline in the central nerve system and/or the releasing of acetylcholine therefrom, therefore, the hydrofluorene derivatives and salts thereof are useful cholinergic nerve system activating agents.

11 Claims, No Drawings

HYDROFLUORENE DERIVATIVES

This application is a continuation of application Ser. No. 07/116,698 filed Nov. 4, 1987 now abandoned.

FIELD OF THE INVENTION

The present invention relates to novel hydrofluorene derivatives and salt thereof and process for preparing the same, as well as it relates to pharmaceutical compositions for improving and/or curing hypoxia and for improving and/or curing cerebral diseases being caused by lowering the functions of acetylcholinergic nerve system.

PRIOR ART

The hydrofluorene derivatives and salt thereof according to the present invention are novel compounds and they have not been known in any prior art literatures.

There have been known some compounds which possess activities for improving and/or curing hypoxia in prior art literatures, however such compounds having chemical structural formulas which are different from those of the present hydrofluorene derivatives and salt thereof. (Cf. European Patent No. 173,331, U.K. Patent No. 2,135,999, German Patent No. 3,407,842 and European Patent No. 226,441, etc.).

On the other hand, there have been known some hydrofluorene compounds having similar chemical structural formulas to those of the present hydrofluorene derivatives and salts thereof, however, such known hydrofluorene compounds possess different pharmacological activities as compared with those of the present hydrofluorene derivatives. (Cf. U. S. Patent No. 3,553,267, British Patent No. 1,176,173 and J. Medicianl Chem., 20, (11), pp. 1400–1408 (1977).).

BRIEF DESCRIPTION OF THE INVENTION

An object of the present invention is to provide novel hydrofluorene derivatives and salt thereof.

Another object of the present invention is to provide processes for preparing the hydrofluorene derivatives and salt thereof.

Further object of the present invention is to provide pharmaceutical compositions for improving and/or curing hypoxia and for improving and/or curing diseases being caused by improving and/or curing cerebral diseases being caused by lowering the functions of acetylcholinergic nerve system.

DETAILED EXPLANATION OF THE INVENTION

The novel hydrofluorene derivatives and salts thereof according to the present invention are represented by the following general formula (1),

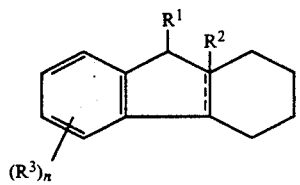

wherein $R^1$ is a group of the formula $=N-R^4$ (wherein $R^4$ is a hydroxy group or a lower alkyl group), a group of the formula

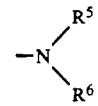

(wherein $R^5$ and $R^6$ are each the same or different, and are each a hydrogen atom, a cycloalkyl group, a lower alkenyl group, a lower alkynyl group, a phenyl group, a phenyl-lower alkyl group, an unsubstituted-$C_1$-$C_8$ alkyl group, a substituted-$C_1$-$C_8$ alkyl group having hydroxy groups as substituents, an unsubstituted lower alkanoyl group, a substituted lower alkanoyl group having halogen atoms as substituents, an unsubstituted piperidinyl group, a substituted piperidinyl group having phenyl-lower alkyl groups as substituents, an unsubstituted piperidinyl-lower alkyl group, a substituted piperidinyl-lower alkyl group having phenyl-lower alkyl groups as substituents, an unsubstituted pyrrolidinyl-lower alkyl group, a substituted pyrrolidinyl-lower alkyl group having lower alkyl groups as substituents, a pyridylcarbonyl group, or a group of the formula

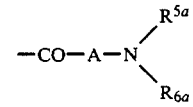

((wherein A is a lower alkylene group, $R^{5a}$ and $R^{6a}$ are each the same or different, and are each a hydrogen atom or a lower alkyl group, further $R^{5a}$ and $R^{6a}$ may form, together with the adjacent nitrogen atom being bonded thereto, and further with or without an additional nitrogen atom or oxygen atom, a saturated 5- or 6-membered heterocyclic group, said heterocyclic group may have 1 to 3 substituents selected from the group consisting of a lower alkyl group, a lower alkenyl group, a lower alkynyl group, an unsubstituted phenyl group and a substituted phenyl group having 1 to 3 substituents selected from the group consisting of a halogen atom and a lower alkoxy group)); further said $R^5$ and $R^6$ may form, together with the adjacent nitrogen atom being bonded thereto, and further with or without an additional nitrogen atom or oxygen atom, a saturated 5- or 6-membered heterocyclic group, said heterocyclic group may have an oxo group as substituent), or a group of the formula

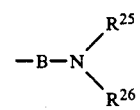

(wherein B is a lower alkylene group, $R^{25}$ and $R^{26}$ are each the same or different, and are each a hydrogen atom, an unsubstituted lower alkyl group, a substituted lower alkyl group having lower alkanoylamino groups, carboxy groups, carbamoyl groups or hydroxy groups as substituents, a pyridyl-lower alkyl group, an unsubstituted pyrrolidinyl-lower alkyl group, substituted pyrrolidinyl-lower alkyl group having lower-alkyl groups as substituents, a furyl-lower alkyl group, further $R^{25}$ and $R^{26}$ may form, together with the adjacent nitrogen atom being bonded thereto, and further with or without an additional nitrogen atom or oxygen atom, a saturated 5- or 6-membered heterocyclic group, said heterocyclic group may have 1 to 3 substituents selected from the group consisting of a lower alkyl group, an amino group, an amino group having lower alkyl groups as substituents, an unsubstituted phenyl group and a substituted phenyl group having 1 to 3 substituents selected from the group consisting of a lower alkyl group, a lower alkoxy group and a halogen atom);

$R^2$ is a hydrogen atom, a lower alkoxy group or a lower alkyl group;

$R^3$ is a hydrogen atom, a lower alkyl group, a halogen atom, a lower alkenyl group, a phenyl-lower alkenyl group, a nitro group, a cycloalkyl-lower alkyl group, a phenyl-lower alkyl group, a lower alkoxy group, a lower alkylthio group, a lower alkylthio-lower alkyl group, a cyano group, a lower alkanoyl group, a carboxy group, a hydroxy group, an amino-lower alkyl group, an amino-lower alkyl group having lower alkyl groups as substituents, a cycloalkyl group, a cycloalkenyl group having one double bond in the cycloalkyl ring, an amino group and an amino group having lower alkyl groups or lower alkanoyl groups as substituents;

n is an integer of 0 to 3;

the carbon-carbon bond between 4a- and 9a-positions in the hydrofluorene skeleton is a single or double bond, provided that when the carbon-carbon bond between 4a- and 9a-positions in the hydrofluorene skeleton is a double bond, then $R^2$ should not be substituted at 9a-position in said skeleton.

Hydrofluorene derivatives and salts thereof represented by the general formula (1) according to the present invention possess excellent activities for improving anoxemic and hypoxic symptoms and syndromes accompanied therewith. More specifically, hydrofluorene derivatives and salts thereof represented by the general formula (1) are useful as for example, cerebral activators, curative agents for amnesia, curative agents for presbyophrenia, curative agents for respiratory arrest caused by poisoning with potassium cyanide, improving agents for hypoxia, preventive agents for arrhythmia and heart failure caused by the shortage of oxygen and others.

Hydrofluorene derivatives and salts thereof according to the present invention are useful as the above-mentioned cerebral activators, for example agents for improving disturbance of consciousness caused by cerebral blood vessel disturbance (e.g., cerebral hemorrhage, cerebral infarction, subarachnoidal hemorrhage, hypertensive encephalopathy and the like), encephalitis, cerebral tumor, head injuries, psychosis, dysbolism, chemical poisonings and physical injuries; also they are useful agents for curing and/or improving sequelas, depressions of attention, hyperkinesia, speech disturbance and mental retardation caused by the above-mentioned diseases.

Hydrofluorene derivatives and salts thereof according to the present invention are low toxici substances and they are featured with less side effects.

Generally speaking, oxygen is an essential element to the living body for sustaining the life through release of energies and metabolisms. Oxygen is converted into so-called "active oxygen radicals", for example, oxygen anion radicals, peroxide ions, hydroxy radicals, etc., which are formed in various biochemical reactions, such as energy releasing reactions, enzymatic reactions and other reactions caused by exposures of ultraviolet rays and various radiations.

The active oxygen radicals are indeed useful for the living body in the actions of oxygenase and of phagocytosis carried out by leucocytes. On the other hand, the active oxygen radicals promote peroxidation reaction of unsaturated fatty acids, such as oleic acid, linoleic acid, linolenic acid and arachidonic acid, etc., such unsaturated fatty acids are existing abundantly in the living body and are the main constituents of the biomembranes. The peroxidation of said unsaturated fatty acids produce peroxidized substances such as peroxidized lipids. Furthermore, similar to the above-mentioned active oxygen radicals, said peroxidized substances also produce alkoxy radicals and hydroxy radicals which will attack the biomembranes and will result disorder of the biomembranes and deactivation of various useful enzymes which are working in the living body. [Cf. "TAISHA" (Metabolisms), Vol. 15, No. 10, (1978)—Special Issue on Active Oxygen.]

On the other hand, there are existing some other enzymes, such as superoxide dismutase (hereinafter referred to as "SOD"), catalase, glutathion peroxide, etc., in the living body. These enzymes prevent the deactivation of metabolisms from the attack caused by the active oxygen radicals. Additionally, there are existing several vitamins, such as tocopherols (vitamin E groups) having antioxidative activities in the living body.

Generally, the normal homeostasis mechanisms in the living body are sustained by the actions of these enzymes and vitamins having antioxidative activities. However, sometimes the prophylazis mechanisms in the living body being suitably maintained by the actions of these enzymes and vitamins may be defected by certain reasons, and the formation of the active oxygen radicals in an amount exceeds the ability of the prophylaxis mechanisms in the living body, as well as the formation and accumulation of the peroxidized substances are observed.

In such cases, when the prophylaxis mechanisms in the living body are defected, then several disorders such as various diseases caused by the aggregation of the platelets, inflammations, disorders of the liver, arteriosclerosis, hemolysis, senescence or presbyophrenia, retinosis, disorder of the lungs, disorders of the heart and the lungs caused by the actions of certain drugs, ischematic coronary heart disease and the like will be occurred by accompanying with the progressive chain reactions of the peroxidation.

Hitherto, compounds having actions for scavenging the active oxygen radicals which are considered to be the main factors of the above-mentioned various diseases, and for preventing or lowering the formation and accumulation of the peroxidized substances in the living body were known and called them as antioxidants. A number of studies on prophylaxis and curative effects by using these antioxidants have been reported in several literatures.

As to enzymatic preparations containing SOD and other enzymes as mentioned previously are reported in "SUPEROXIDE TO IGAKU" (Superoxide and Medicines) by Yoshihiko Ohyanagi, pp. 137–141, published from Kyoritsu Publishing Co., Ltd.; and some articles relating to butylhydroxytoluene (BHT), butylhydroxyanisol (BHA), α-tocopherol (vitamin E) and others, reported by Makoto Mino and Hidetaka Tanaka: "IYAKU JOURNAL" (Pharmaceutical Journal), Vol. 19, No. 12, pages 2351–2359, (1983); and by Toshihiko Suematsu: Ibid., Vol. 19, No. 5, pages 909-914, (1983) and others.

In addition to the above, hydrofluorene derivatives and salts thereof according to the present invention possess actions for scavenging active oxygen radicals and for preventing and lowering the formation of peroxidized lipids in the living body. Therefore, hydrofluorene derivatives and salts thereof according to the present invention are useful prophylactic and treating agents for various disturbances and diseases caused by the excessive formation of the above-mentioned active oxygen radicals, the accumulation of peroxidized lipids in the living body or for deficiencies of protective mechanisms in the living body against such active oxygen radicals and peroxidized lipids. Thus hydrofluorene derivatives and salts thereof according to the present invention are useful as anti-arteriosclerosis agents, preventive agents of cancer, anti-inflammatory agents, analgesics, treating agents for auto-immune diseases, inhibitory agents for aggregation of plateles, hypotensive agents, anti-hyperlipemia agents, prophylactic and treating agents for retinosis of immature infant and for cataract and the like.

Furthermore, hydrofluorene derivatives and salts thereof according to the present invention are useful not only as the above-mentioned pharmaceutical uses, but also useful as anti-oxidative agents for fats and oils being contained in various processed food products.

Hydrofluorene derivatives and salts thereof according to the present invention accelerate the uptaking of high-affinity choline in the central nerve system, and/or the releasing of acetylcholine therefrom, also said derivatives and salts thereof improve the memory-lerning disturbance induced by scopolamine which is an anticholinergic agent.

In the case of Alzheimer's disease which is come out as one of the typical syndromes of presbyophrenia, it is reported that some important changes are occurred in the cerebral cholinergic nerve system and the functions of said system are decreased thereby. [Cf. E. K. Perry, and R. H. Perry: "Biochemistry of Dementia" (1980), page 135, published by John, Wiley & Sons, Inc.; and T. D. Reisine, H. I. Yamamura, E. D. Bird, R. Spokes and S. J. Enna: Brain Research, Vol. 159, pages 477-481 (1978)].

Therefore, hydrofluorene derivatives and salts thereof according to the present invention, which accelerate the functions of the cholinergic nerve systems in the brain, are considered to be useful curing agents for sequelas and mental disorder caused by lowering of the functions of acetylcholinergic nerve system, for example Alzheimer's disease which is one of the typical syndromes of presbyophrenia, amnesia, disturbance of memories and external head injuries, brain surgeries, chemical poisoning, disturbance of circulation, cerebral dysbolisms, encephalitis and the like.

In the present specification, the substituents represented by symbols $R^1$ to $R^5$, $R^{5a}$, $R^{6a}$, $R^{25}$, $R^{26}$, A, and B are exemplified more specifically as follows.

The lower alkyl group, means a straight-chain or branched-chain alkyl group having 1 to 6 carbon atoms, and the examples including methyl, ethyl, propyl, isopropyl, butyl, tert-butyl, pentyl, hexyl, 1-methylpropyl, 2-methylpropyl, 1,1-dimethylpropyl, 1-methylbutyl, 2-methylbutyl, 3-methylbutyl, 2,2-dimethylpropyl, 2,3-dimethyl propyl, 1-methylpentyl, 1,1-dimethylbutyl and 1-ethylbutyl groups.

The halogen atom, including a fluorine atom, chlorine atom, bromine atom and iodine atom.

The phenyl-lower alkyl group means a phenylalkyl group in which the alkyl moiety is a straight-chain or branched-chain alkyl group having 1 to 6 carbon atoms, and the examples including benzyl, 2-phenylethyl, 1-phenylethyl, 3-phenylpropyl, 4-phenylbutyl, 1,1-dimethyl-2-phenylethyl, 5-phenylpentyl, 6-phenylhexyl and 2-methyl-3-phenylpropyl groups.

The unsubstituted lower alkanoyl group and substituted lower alkanoyl group having halogen atoms as substituents mean an unsubstituted straight-chain or branched-chain alkanoyl group having 1 to 6 carbon atoms, and a substituted straight-chain or branched-chain alkanoyl group having 1 to 6 carbon atoms and having 1 to 3 halogen atoms as substituents, and the examples including formyl, acetyl, propionyl, butyryl, isobutyryl, pentanoyl, tert-butylcarbonyl, hexanoyl, 2,2,2-trifluoroacetyl, 2,2,2-trichloroacetyl, 2-chloroacetyl, 2-bromoacetyl, 2-fluoroacetyl, 2-iodoacetyl, 2,2-difluoroacetyl, 2,2-dibromoacetyl, 3,3,3-trifluoropropionyl, 3,3,3-trichloropropionyl, 3-chloropropionyl, 2,3-dichloropropionyl, 4,4,4-trichlorobutyryl, 4-fluorobutyryl, 5-chloropentanoyl, 3-chloro-2-methylpropionyl, 6-bromohexanoyl and 5,6-dibromohexanoyl groups.

The lower alkylene group means a straight-chain or branched-chain alkylene group having 1 to 6 carbon atoms, and the examples including methylene, ethylene, trimethylene, 2-methyltrimethylene, 2,2-dimethyltrimethylene, 1-methyltrimethylene, methylmethylene, ethylmethylene, tetramethylene, pentamethylene and hexamethylene groups.

The lower alkoxy group means a straight-chain or branched-chain alkoxy group having 1 to 6 carbon atoms and the examples including methoxy, ethoxy, propoxy, isopropoxy, butoxy, tert-butoxy, pentyloxy and hexyloxy groups.

The phenyl group and substituted phenyl group having 1 to 3 substituents selected from the group consisting of a halogen atom and a lower alkoxy group on the phenyl ring mean a phenyl group and a substituted phenyl group having 1 to 3 substituents selected from the group consisting of a halogen atom and a straight-chain or branched-chain alkoxy group having 1 to 6 carbon atoms on the phenyl ring, and the examples including phenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-iodophenyl, 3-iodophenyl, 4-iodophenyl, 3,5-dichlorophenyl, 2,6-dichlorophenyl, 3,4-dichlorophenyl, 3,4-difluorophenyl, 3,5-dibromophenyl, 3,4,5-trichlorophenyl, 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 4-hexyloxyphenyl, 3,4-dimethoxyphenyl, 3,4-diethoxyphenyl, 3,4,5-trimethoxyphenyl, 2,5-dimethoxyphenyl, 3-ethoxy-4-chlorophenyl, 2-chloro-6-methoxyphenyl and 2-methoxy-3-chlorophenyl groups.

The cycloalkyl group means a cycloalkyl group having 3 to 8 carbon atoms, and the examples including cyclopropyl, cyclobutyl, cyclopentyl, cyclohexyl, cycloheptyl and cyclooctyl groups.

The unsubstituted amino-lower alkyl group and substituted amino-lower alkyl group mean a straight-chain or branched-chain alkyl group having 1 to 6 carbon atoms having amino group and a straight-chain or branched-chain alkyl group having 1 to 6 carbon atoms having amino group which having 1 to 2 straight-chain or branched chain alkyl groups having 1 to 6 carbon atom as substituents, and the examples including aminomethyl, 2-aminoethyl, 1-aminoethyl, 3-aminopropyl, 4-aminobutyl, 5-aminopentyl, 6-aminohexyl, 2-methyl-3-aminopropyl, 1,1-dimethyl-2-aminoethyl, methylaminomethyl, 2-(ethylamino)ethyl, 1-(propylamino)ethyl, 3-(n-butylamino)propyl, 4-(pentylamino)butyl, 5-(hexylamino)pentyl, 6-(dimethylamino)hexyl, 2-methyl-3-(diethylamino)propyl, 1,1-dimethyl-2-(diisopropylamino)ethyl, 3-(dihexylamino)propyl, 4-(methyl, ethylamino)butyl, 5-(methyl, pentylamino)pentyl, 6-(ethyl, propylamino)hexyl, 2-methyl-3-(methyl, hexylamino)propyl, and 1,1-dimethyl-2-(dimethylamino)ethyl groups.

The unsubstituted pyrrolidinyl-lower alkyl groups and substituted pyrrolidinyl-lower alkyl group mean an unsubstituted pyrrolidinylalkyl group and substituted pyrrolidinylalkyl group in which the alkyl moiety is a straight-chain or branched-chain alkyl group having 1 to 6 carbon atoms, and having a straight-chain or branched-chain alkyl group having 1 to 6 carbon atoms as substituent in the pyrrolidine ring, and the examples including pyrrolidinylmethyl, 2-pyrrolidinylethyl, 1-pyrrolidinylethyl, 3-pyrrolidinylpropyl, 4-pyrrolidinylbutyl, 1,1-dimethyl-2-pyrrodidinylethyl, 5-pyrrolidinylpentyl, 6-pyrrolidinylhexyl, 2-methyl-3-pyrrolidinylpropyl, (1-ethyl-2-pyrrolidinyl)methyl, 1-(1-methyl-2-pyrrolidinyl)ethyl, 2-(5-propyl-2-pyrrolidinyl)ethyl, 3-(3-butyl-2-pyrrolidinyl)propyl, 4-(4-pentyl-3-pyrrolidinyl)butyl, 5-(5-hexyl-3-pyrrolidinyl)pentyl, 6-(2-methyl-4-pyrrolidinyl)hexyl, 2-methyl-3-(2-methyl-5-pyrrolidinyl)propyl and 1,1-dimethyl-2-(1-ethyl-2-pyrrolidinyl)ethyl groups.

The phenyl-lower alkenyl group means a phenylalkenyl group in which the alkenyl moiety is a straight-chain or branched-chain alkenyl group having 2 to 6 carbon atoms, and the examples including 2-phenylvinyl, 3-phenylallyl, 1-phenylallyl, 2-phenylallyl, 4-phenyl-2-butenyl, 3-phenyl-2-butenyl, 2-phenyl-2-butenyl, 1-phenyl-2-butenyl, 4-phenyl-3-butenyl, 3-phenyl-3-butenyl, 2-phenyl-3-butenyl, 1-phenyl-3-butenyl, 3-phenyl-1-methylallyl, 1-methyl-1-phenylallyl, 2-phenyl-1-methylallyl, 5-phenyl-2-pentenyl, 6-phenyl-2-hexenyl, 1-phenyl-2-hexenyl and 1-phenyl-2-pentenyl groups.

The unsubstituted $C_1$–$C_8$ alkyl group and substituted $C_1$–$C_8$ alkyl group mean an unsubstituted straight-chain or branched-chain alkyl group having 1 to 8 carbon atoms, and a straight-chain or branched-chain alkyl group having 1 to 8 carbon atoms and having hydroxy groups as substituents, and the examples including, in addition to the above-mentioned examples of the lower alkyl groups, heptyl, octyl, hydroxymethyl, 1-hydroxyethyl, 2-hydroxyethyl, 3-hydroxypropyl, 4-hydroxybutyl, 5-hydroxypentyl, 6-hydroxyhexyl, 2-methyl-3-hydroxypropyl, 1,1-dimethyl-2-hydroxyethyl, 7-hydroxyheptyl and 8-hydroxyoctyl groups.

The lower alkenyl group means a straight-chain or branched-chain alkenyl group having 2 to 6 carbon atoms, and the examples including vinyl, allyl, 2-butenyl, 3-butenyl, 1-methylallyl, 2-pentenyl and 2-hexenyl groups.

The lower alkynyl group means a straight-chain or branched-chain alkynyl group having 2 to 6 carbon atoms, and the examples including ethynyl, 2-propynyl, 2-butynyl, 3-butynyl, 1-methyl-2-propynyl, 2-pentynyl and 2-hexynyl groups.

The unsubstituted piperidinyl group and substituted piperidinyl group having phenyl-lower alkyl groups as substituents mean an unsubstituted piperidinyl group and a substituted piperidinyl group having phenylalkyl groups as substituents in which the alkyl moiety is a straight-chain or branched-chain alkyl groups having 1 to 6 carbon atoms, and the examples including 1-benzyl-4-piperidinyl, 1-(2-phenylethyl)-4-piperidinyl, 1-(1-phenylethyl)-3-piperidinyl, 1-(3-phenylpropyl)-2-piperidinyl, 2-(4-phenylbutyl)-4-piperidinyl, 3-(5-phenylpentyl)-4-piperidinyl, 4-(6-phenylpentyl)-2-piperidinyl and 1-(2-methyl-3-phenylpropyl)-4-piperidinyl groups.

The unsubstituted piperidinyl-lower alkyl group and substituted piperidinyl-lower alkyl group having phenyl-lower alkyl groups as the substituents mean an unsubstituted piperidinylalkyl group in which the alkyl moiety is a straight-chain or branched-chain alkyl group having 1 to 6 carbon atoms and substituted piperidinylalkyl group in which the alkyl moiety is a straight-chain or branched-chain alkyl group having 1 to 6 carbon atoms, and having phenylalkyl groups as the substituents in which the alkyl moiety is a straight-chain or branched chain alkyl group having 1 to 6 carbon atoms, and the examples including (1-benzyl-4-piperidinyl)methyl, 2-[1-(2-phenylethyl)-4-piperidinyl]ethyl, 1-[1-(1-phenylethyl)-3-piperidinyl]ethyl, 3-[1-(3-phenylpropyl)-2-piperidinyl]propyl, 4-[2-(4-phenylbutyl)-4-piperidinyl]butyl, 5-[3-(5-phenylpentyl)-4-piperidinyl]pentyl, 6-[4-(6-phenylpentyl)-2-piperidinyl]hexyl and 2-methyl-3-[1-(2-methyl-3-phenylpropyl)-4-piperidinyl]propyl groups.

The unsubstituted amino group and substituted amino group having lower alkyl groups or lower alkanoyl groups as the substituents mean an unsubstituted amino group and substituted amino group having a straight-chain or branched-chain alkyl group having 1 to 6 carbon atoms as substituents or having a straight-chain or branched-chain alkanoyl group having 1 to 6 carbon atoms as substituents, and the examples including amino, methylamino, ethylamino, propylamino, tert-butylamino, pentylamino, hexylamino, dimethylamino, diethylamino, d-n-propylamino, di-n-butylamino, dipentylamino, dihexylamino, N-methyl-N-n-butylamino, N-methyl-N-pentylamino, N-ethyl-N-hexylamino, acetylamino, formylamino, propionylamino, butyrylamino, pentanoylamino, hexanoylamino, N-methyl-N-acetylamino, N-ethyl-N-propionylamino, N-methyl-N-butyrylamino, N-n-propyl-N-pentanoylamino and N-ethyl-N-hexanoylamino groups.

The lower alkylthio group means a straight-chain or branched-chain alkylthio group having 1 to 6 carbon atoms, and the examples including methylthio, ethylthio, propylthio, isopropylthil, butylthio, tertbutylthio, pentylthio and hexylthio groups.

The lower alkylthio-lower alkyl group means a straight-chain or branched-chain alkylthioalkyl group having 1 to 6 carbon atoms in which the alkyl moiety is a straight-chain or branched-chain alkyl group having 1 to 6 carbon atoms, and the examples including methylthiomethyl, 2-methylthioethyl, 1-ethylthioethyl, 3-propylthiopropyl, 4-isopropylthiobutyl, 1,1-dimethyl-2-butylthioethyl, 5-tert-butylthiopentyl, 6-pentylthiohexyl and 2-methyl-3-hexylthiopropyl groups.

The lower alkanoyl group means a straight-chain or branched-chain alkanoyl group having 1 to 6 carbon atom, and the examples including formyl, acetyl, propionyl, butyryl, isobutyryl, pentanoyl and hexanoyl groups.

The cycloalkyl-lower alkyl group means a cycloalkylalkyl group having 3 to 8 carbon atoms in which the alkyl moiety is a straight-chain or branched-chain alkyl group having 1 to 6 carbon atoms, and the examples including cyclopropylmethyl, cyclobutylmethyl, cyclopentylmethyl, cyclohexylmethyl, cycloheptylmethyl, cyclooctylmethyl, 2-cyclohexylethyl, 1-cyclohexylethyl, 1-cyclohexylpropyl, 3-cyclopentylpropyl, 2-cyclopentylethyl, 4-cyclobutylbutyl, 5-cycloheptylpentyl, 6-cyclooctylhexyl, 1,1-dimethyl-2-cyclopropylethyl and 2-methyl-3-cyclopentylpropyl groups.

The cycloalkyl group and cycloalkenyl group having one double bond in the cycloalkyl ring mean a cycloalkyl group having 3 to 8 carbon atoms and a cycloalkyl group having 3 to 8 carbon atoms and having one double bond in the cycloalkyl ring, and the examples including cyclopropyl, cyclobutyl, cyclopentyl, cyclohexyl, cycloheptyl, cyclooctyl, cyclobutenyl, cyclopentenyl, cyclohexenyl, cycloheptenyl, and cyclooctenyl groups.

The pyridyl-lower alkyl group means a pyridylalkyl group in which the alkyl moiety is a straight-chain or branched-chain alkyl group having 1 to 6 carbon atoms, and the examples including (2-, 3- or 4-pyridyl)methyl, 2-(2-, 3-, or 4-pyridyl)ethyl, 1-(2-, 3- or 4-pyridyl)ethyl, 3-(2-, 3- or 4-pyridyl)propyl, 4-(2-, 3- or 4-pyridyl)butyl, 1,1-dimethyl-2-(2-, 3- or 4-pyridyl)ethyl, 5-(2-, 3- or 4-pyridiyl)pentyl, 6-(2-, 3- or 4-pyridyl)hexyl, and 2-methyl-3-(2-, 3- or 4-pyridyl)propyl groups.

The unsubstituted lower alkyl group and substituted lower alkyl group having lower alkanoylamino groups, carboxy groups, carbamoyl groups or hydroxy groups as substituents mean an unsubstituted straight-chain or branched-chain alkyl group having 1 to 6 carbon atoms and substituted straight-chain or branched-chain alkyl group having 1 to 6 carbon atoms and having 1 to 3 substituents selected from the group consisting of a straight-chain or branched-chain alkanoylamino group having 1 to 6 carbon atoms, a carboxy group, a carbamoyl group and a hydroxy group, and the examples including, in addition to the above-mentioned lower alkyl group, hydroxylmethyl, 1-hydroxyethyl, 2-hydroxyethyl, 3-hydroxylpropyl, 4-hydroxybutyl, 5-hydroxypentyl, 6-hydroxyhexyl, 2-methyl-3-hydroxylpropyl, 1,1-dimethyl-2-hydroxyethyl, 2,3,4-trihydroxypentyl, 1,2,3-trihydroxybutyl, 2,3-dihydroxypropyl, 1,2-dihydroxyethyl, 1,3-dihydroxypropyl, 1,4-dihydroxybutyl, 5,6-dihydroxyhexyl, carboxymethyl, 1-carboxyethyl, 2-carboxyethyl, 3-carboxylpropyl, 4-carboxybutyl, 5-carboxypentyl, 6-carboxyhexyl, 2-methyl-3-carboxypropyl, 1,1-dimethyl-2-carboxyethyl, carbamoylmethyl, 1-carbamoylethyl, 2-carbamoylethyl, 3-carbamoylpropyl, 4-carbamoylbutyl, 5-carbamoylpentyl, 6-carbamoylhexyl, 2-methyl-3-carbamoylpropyl, 1,1-dimethyl-2-carbamoylethyl, formylaminomethyl, 2-acetylaminoethyl, 1-propionylaminoethyl, 3-butyrylaminopropyl, 4-isobutyrylaminobutyl, 5-pentanoylaminopentyl, 6-tert-butylcarbonylaminohexyl and hexanoylaminomethyl groups.

The unsubstituted lower amino group and mean an amino group and a substituted amino group having 1 to 2 straight-chain or branched-chain alkyl groups having 1 to 6 carbon atoms as substituents, and the examples including amino, methylamino, ethylamino, propylamino, tert-butylamino, pentylamino, hexylamino, dimethylamino, di-n-propylamino, di-n-butylamino, dipentylamino, dihexylamino, N-methyl-N-n-butylamino, N-methyl-N-pentylamino and N-ethyl-N-hexylamino groups.

The unsubstituted phenyl group and substituted phenyl group having 1 to 3 substituents selected from the group consisting of a lower alkyl group, a lower alkoxy group and a halogen atom on the phenyl ring mean an unsubstituted phenyl group and substituted phenyl group having 1 to 3 substituents selected from the group consisting of a straight-chain or branched-chain alkyl group having 1 to 6 carbon atoms, a straight-chain or branched-chain alkoxy group having 1 to 6 carbon atoms and a halogen atom on the phenyl ring, and the examples including phenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-iodophenyl, 3-iodophenyl, 4-iodophenyl, 3,5-dichlorophenyl, 2,6-dichlorophenyl, 2,3-dichlorophenyl, 3,4-difluorophenyl, 3,5-dibromophenyl, 3,4,5-trichlorophenyl, 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 4-hexyloxyphenyl, 3,4-dimethoxyphenyl, 3,4-diethoxyphenyl, 3,4,5-trimethoxyphenyl, 2,5-dimethoxyphenyl, 3-ethoxy-4-chlorophenyl, 2-chloro-6-methoxyphenyl, 2-methoxy-3-chlorophenyl, 2-methylphenyl, 3-methylphenyl, 4-methylphenyl, 2-ethylphenyl, 3-ethylphenyl, 4-ethylphenyl, 4-isopropylphenyl, 3-hexylphenyl, 3,4-dimethylphenyl, 3,4-diethylphenyl, 3,4,5-trimethylphenyl, 3-methyl-4-bromophenyl, 2-chloro-3-methylphenyl and 2-methyl-3-chlorophenyl groups.

The substituted heterocyclic group having 1 to 3 substituents selected from the group consisting of a lower alkyl group, an unsubstituted amino group, a substituted amino group having lower alkyl groups as substituents, an unsubstituted phenyl group and a substituted phenyl group having 1 to 3 substituents on the phenyl ring, selected from the group consisting of a lower alkyl group, a lower alkoxy group and a halogen atom mean the above-mentioned saturated 5- or 6-membered heterocyclic groups having 1 to 3 substituents selected from the group consisting of a straight-chain or branched-chain alkyl group having 1 to 6 carbon atoms, an amino group, a substituted amino group having 1 to 2 straight-chain or branched-chain alkyl groups having 1 to 6 carbon atoms as substituents, a phenyl group, a substituted phenyl group having 1 to 3 substituents on the phenyl ring selected from the group consisting of a straight-chain or branched-chain alkyl group having 1 to 6 carbon atoms, a straight-chain or branched-chain alkoxy group having 1 to 6 carbon atoms and a halogen atom, and the examples including 4-methyl-1-piperzinyl, 4-ethyl-1-piperazinyl, 4-propyl-1-piperazinyl, 4-butyl-1-piperazinyl, 4-pentyl-1-piperazinyl, 4-hexyl-1-piperazinyl, 2-methyl-1-pyrrolidinyl, 3-ethyl-1-pyrrolidinyl, 2-propyl-1-pyrrolidinyl, 3-butyl-1-pyrrolidinyl, 2-pentyl-1-pyrrolidinyl, 3-hexyl-1-pyrrolidinyl, 2-methyl-1-piperidinyl, 3-ethyl-1-piperidinyl, 4-propyl-1-piperidinyl, 2-butyl-1-piperidinyl, 3-pentyl-1-piperidinyl, 4-hexyl-1-piperidinyl, 2-methylmorpholino, 3-methylmorpholino, 2-ethylmorpholino, 3-propylmorpholino, 2-butylmorpholino, 3-pentylmorpholino, 2-hexylmorpholino, 2,6-dimethylmorpholino, 2,6-dimethyl-1-piperidinyl, 3,4-dimethyl-1-piperazinyl, 3,4,5-trimethyl-1-piperazinyl, 3-amino-1-piperazinyl, 2-methylamino-1-piperazinyl, 4-amino-1-piperidinyl, 4- methylamino-1-piperidinyl, 4-dimethylamino-1-piperidinyl, 3-ethylamino-1-piperidinyl, 2-propylamino-1-piperidinyl, 4-tert-butylamino-1-piperidinyl, 3-pentylamino-1-piperidinyl, 2-hexylamino-1-piperidinyl, 4-diethylamino-1-piperidinyl, 2-aminomorpholino, 3-methylaminomorpholino, 2-dimethylaminomorpholino, 4-(N-methyl-N-butylamino)-1-piperidinyl, 2-methylamino-1-pyrrolidinyl, 3-amino-1-pyrrolidinyl, 3-dimethylamino-1-pyrrolidinyl, 3-ethylamino-1-pyrrolidinyl, 2-propylamino-1-pyrrolidinyl, 3-tert-butylamino-1-pyrrolidinyl, 2-pentylamino-1-pyrrolidinyl, 3-hexylamino-1-pyrrolidinyl, 3-diethylamino-1-pyrrolidinyl, 4-phenyl-1-piperazinyl, 4-(3-methylphenyl)-1-piperazinyl, 4-(3-methoxyphenyl)-1-piperazinyl, 4-(3-chlorophenyl)-1-piperazinyl, 4-(2,3-dichlorophenyl)-1-piperazinyl, 4-(2-methyl-3-chlorophenyl)-1-piperazinyl, 4-(3,4,5-trimethoxyphenyl)-1-piperidinyl, 2-(4-methoxy-2chlorophenyl)morpholino, 3-(4-fluorophenyl)morpholino, 3-(2-bromophenyl)-1-piperidinyl, 2-(2-methyl-3-chlorophenyl)morpholino, 3-(2-methoxyphenyl)-1-pyrrolidinyl, 3-amino-4-methyl-1-pyrrolidinyl, 3-methylamino-4-methyl- 1-pyrrolidinyl, and 3-methyl-4-dimethylamino-1-piperidinyl groups can be exemplified.

The pyridyl-lower alkanoyl group means a pyridyl-substituted straight-chain or branched-chain alkanoyl group having 2 to 6 carbon atoms, and the examples including 2-(3-pyridyl)acetyl, 2-(2-pyridyl)acetyl, 2-(4-pyridyl)acetyl, 3-(3-pyridyl)acetyl, 4-(2-pyridyl)acetyl, 5-(4-pyridyl)acetyl and 6-(3-pyridyl)acetyl groups.

The saturated 5- or 6-membered heterocyclic group formed by combining $R^5$ and $R^6$; $R^{5a}$ and $R^{6a}$; and $R^{25}$ and $R^{26}$ together with the adjacent nitrogen atom being bonded thereto, further with or without an additional nitrogen atom or oxygen atom, the examples including pyrrolidinyl, piperidinyl, piperazinyl and morpholino groups.

The heterocyclic group having oxo group as substituent, the examples including 2-oxo-1-pyrrolidinyl, 3-oxo-1-pyrrolidinyl, 2-oxo-1-piperidinyl, 3-oxo-1-piperidinyl, 4-oxo-1-piperidinyl, 2-oxo-1-piperazinyl, 3-oxo-1-piperazinyl, 2-oxomorpholino and 3-oxomorpholino groups.

The heterocyclic group having 1 to 3 substituents selected from the group consisting of a lower alkyl group, a lower alkenyl group, a lower alkynyl group, an unsubstituted phenyl group and a substituted-phenyl group having 1 to 3 substituents selected from the group consisting of a halogen atom and a lower alkoxy group means a 5- or 6-membered saturated heterocyclic group having 1 to 3 substituents selected from the group consisting of a straight-chain or branched-chain alkyl group having 1 to 6 carbon atoms, a straight-chain or branched-chain alkenyl group having 2 to 6 carbon atoms, a straight-chain or branched-chain alkynyl group having 2 to 6 carbon atoms, a phenyl group and a substituted-phenyl group having 1 to 3 substituents selected from the group consisting of a halogen atom and a straight-chain or branched chain alkoxy group having 1 to 6 carbon atoms, and the examples including 4-methyl-1-piperazinyl, 4-ethyl-1-piperazinyl, 4-propyl-1-piperazinyl, 4-butyl-1-piperazinyl, 4-pentyl-1-piperazinyl, 4-hexyl-1-piperazinyl, 2-methyl-1-pyrrolidinyl, 3-ethyl-1-pyrrolidinyl, 2-propyl-1-pyrrolidinyl, 3-butyl-1-pyrrolidinyl, 2-pentyl-1-pyrrolidinyl, 3-hexyl-1-pyrrolidinyl, 2-methyl-1-piperidinyl, 3-ethyl-1-piperidinyl, 4-propyl-1-piperidinyl, 2-butyl-1-piperidinyl, 3-pentyl-1-piperidinyl, 4-hexyl-1-piperidinyl, 2-methylmorpholino, 3-methylmorpholino, 2-ethylmorpholino, 3-propylmorpholino, 2-butylmorpholino, 3-pentylmorpholino, 2-hexylmorpholino, 2,6-dimethylmorpholino, 2,6-dimethyl-1-piperidinyl, 3,4-dimethyl-1-piperazinyl, 3,4,5-trimethyl-1-piperazinyl, 3-allyl-1-piperazinyl, 2-(2-butenyl)-1-piperazinyl, 4-(3-butenyl)-1-piperazinyl, 4-allyl-1-piperidinyl, 4-(1-methylallyl)-1-piperazinyl, 3-(2-pentenyl)-1-piperazinyl, 2-(2-hexenyl)-1-piperazinyl, 4-(1-methylallyl)-1-piperidinyl, 3-(2-pentenyl)- 1-piperidinyl, 2-(2-hexenyl)-1-piperidinyl, 3-allylmorpholino, 2-(2-butenyl)morpholino, 2-allyl-1-pyrrolidinyl, 3-(1-methylallyl)-1-pyrrolidinyl, 4-(2-propynyl)-1-piperazinyl, 4-(2-butynyl)-1-piperazinyl, 4-(1-methyl-2-propynyl)-1-piperazinyl, 4-(2-pentynyl)-1-piperazinyl, 4-(2-hexynyl)-1-piperazinyl, 4-(2-propynyl)-1-piperidinyl, 3-(1-methyl-2-propynyl)-1-piperidinyl, 2-(2-propynyl)morpholino, 3-(2-pentynyl)morpholino, 2-(2-propynyl)-1-pyrrolidinyl, 3-(2-butynyl)-1-pyrrolidinyl, 4-phenyl-1-piperazinyl, 4-(3-methoxyphenyl)-1-piperazinyl, 4-(3-chlorophenyl)-1-piperazinyl, 4-(2,4-dichlorophenyl)-1-piperazinyl, 4-(2-methoxy-3-chlorophenyl)-1-piperazinyl, 4-(3-ethoxyphenyl)-1-piperazinyl, 4-(4-iodophenyl)-1-piperazinyl, 4-(3,4,5-trimethoxyphenyl)-1-piperidinyl, 2-(4-methoxy-2-chlorophenyl)morpholino, 3-(4-chlorophenyl)morpholino, 3-(2-bromophenyl)-1-piperidinyl, 3-(2-methoxyphenyl)-1-pyrrolidinyl, 3-allyl-4-methyl-1-pyrrolidinyl, 3-(2-propynyl)-4-methyl-1-pyrrolidinyl and 3-methyl-4-phenyl-1-piperidinyl groups.

The lower alkanoylamino group means a straight-chain or branched-chain alkanoylamino group having 1 to 6 carbon atoms, and the examples including formylamino, acetylamino, propionylamino, butyrylamino, isobutyrylamino, pentanoylamino, tert-butylcarbonylamino and hexanoylamino groups.

The furyl-lower alkyl group means a furylalkyl group in which the alkyl moiety is a straight-chain or branched-chain alkyl group having 1 to 6 carbon atoms, and the examples including (2-furyl)methyl, 2-(3-furyl)ethyl, 1-(2-furyl)ethyl, 3-(2-furyl)propyl, 4-(3-furyl)butyl, 1,1-dimethyl-2-(2-furyl)ethyl, 5-(3-furyl)pentyl, 6-(2-furyl)hexyl and 2-methyl-3-(3-furyl)propyl groups.

The compound of the present invention can be produced by various methods, and representative examples of the methods will be shown below.

Reaction process formula-1

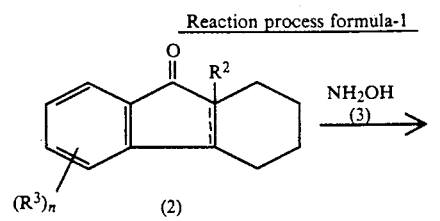

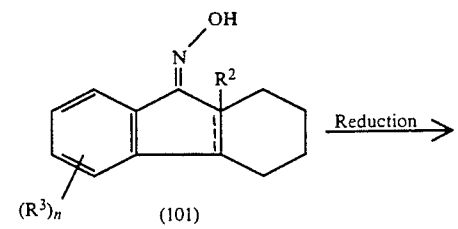

-continued
Reaction process formula-1

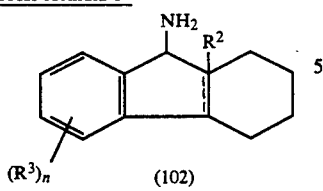

(102)

wherein R², R³ and n are the same as defined above.

The reaction of the compound of the general formula (2) with hydroxylamine (3) can be carried out in a suitable inert solvent in the presence or absence of a basic compound. The basic compound used in this reaction includes for example inorganic basic compounds such as sodium hydroxide, potassium hydroxide, sodium carbonate, potassium carbonate, etc., and organic bases such as piperidine, pyridine, triethylamine, 1,5-diazabicyclo[4,3,0]nonene-5 (DBN), 1,8-diazabicyclo[5,4,0]undecene-7 (DBU), 1,4-diazabicyclo[2,2,2]octane (DABCO), etc. The inert solvent used may be any of those exerting no adverse effect on the reaction, and there may be given for example lower alcohols (e.g. methanol, ethanol, isopropanol), ethers (e.g. dioxane, tetrahydrofuran, diethyl ether, ethylene glycol monomethyl ether), aromatic hydrocarbons (e.g. benzene, toluene, xylene), halogenated hydrocarbons (e.g. dichloromethane, dichloroethane, chloroform, carbon tetrachloride), dimethylformamide, dimethyl sulfoxide, hexamethylphosphoric acid triamide, pyridine and mixtures thereof. The amount of hydroxylamine (3) used is generally at least an equimolar amount, preferably from an equimolar amount to 5 times by mole based on the compound of the general formula (2). The reaction temperature is generally from room temperature to 200° C., preferably from 50° to 150° C. Generally, this reaction comes to an end in from about 1 to about 30 hours.

Reduction of the compound of the general formula (101) may be carried out using a condition for the reduction of the compound of the general formula (109) shown in the Reaction process formula-6 described later. Preferably, however, it can be carried out by catalytic hydrogenation in a suitable solvent in the presence of a catalyst. The solvent used includes for example water, acetic acid, alcohols (e.g. methanol, ethanol, isopropanol), hydrocarbons (e.g. hexane, cyclohexane), ethers (e.g. diethylene glycol dimethyl ether, dioxane, tetrahydrofuran, diethyl ether), esters (e.g. ethyl acetate, methyl acetate), aprotic polar solvents (e.g. dimethylformamide), and mixtures thereof. The catalyst used includes for example palladium, palladium black, palladium-carbon, platinum, platinum oxide, copper chromite, Raney nickel, etc. A preferred amount of the catalyst is generally from 0.02 to 1 time by weight based on the compound of the general formula (101). The reaction temperature is generally from the vicinity of −20° C. to the vicinity of 100° C., preferably from the vicinity of 0° C. to the vicinity of 70° C., and a preferred hydrogen pressure is generally from 1 to 10 atm. Generally, said reaction comes to an end in from about 0.5 to about 20 hours.

When R³ is a halogen atom, it is sometimes reduced to turn hydrogen atom. When R³ is a phenyl lower alkenyl, lower alkenyl, nitro or cycloalkenyl group, it is sometimes similarly reduced to turn phenyl lower alkyl, cycloalkyl lower alkyl, lower alkyl, amino or cycloalkyl group.

Reaction process formula-2

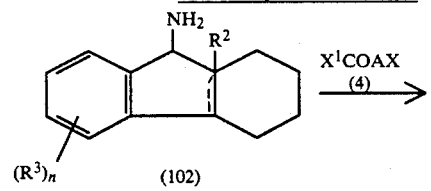

(102)

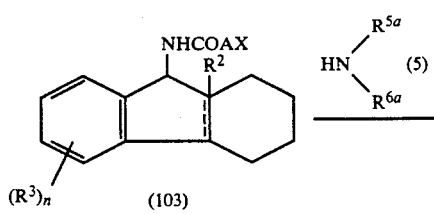

(103)

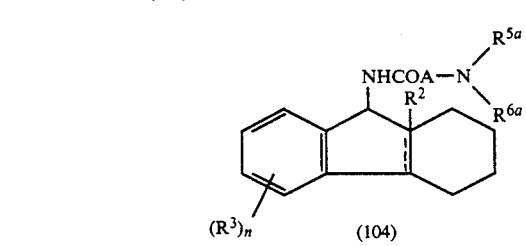

(104)

wherein R², R³, R⁵ᵃ, R⁶ᵃ, A and n are the same as defined above, and X¹ and X each represents a halogen atom.

Reaction of the compound of the general formula (102) with the compound of the general formula (4) is carried out in a suitable inert solvent in the presence of a dehydrohalogenating agent. The inert solvent used here includes halogenated hydrocarbons (e.g. dichloromethane, chloroform), ethers (e.g. tetrahydrofuran, diethyl ether), aromatic hydrocarbons (e.g. benzene, toluene, xylene), esters (e.g. methyl acetate, ethyl acetate), polar solvents (e.g. dimethylformamide, dimethyl sulfoxide, hexamethylphosphoric acid triamide, acetonitrile, acetone, acetic acid, pyridine, water), etc. The dehydrohalogenating agent used includes for example organic bases such as triethylamine, trimethylamine, pyridine, dimethylaniline, N-methylborpholine, 4-dimethylaminopyridine, 4-(1-pyrrolidinyl)pyridine, 1,5-diazabicyclo[4,3,0]nonene-5 (DBN), 1,8-diazabicyclo[5,4,0]undecene-7 (DBU), 1,4-diazabicyclo[2,2,2]octane (DABCO), sodium acetate, etc., and inorganic bases such as sodium hydride, potassium carbonate, sodium carbonate, potassium hydrogencarbonate, sodium hydrogencarbonate, potassium hydroxide, sodium hydroxide, etc. The amount of the compound (4) based on the compound (102) is generally at least an equimolar amount, preferably from an equimolar amount to 3 times by mole. Said reaction is carried out at a temperature of, generally, from about −20° to about 150° C., preferably from 0° to 100° C., and it comes to an end in a reaction time of from about 5 minutes to about 15 hours. Thus, the compound (103) is obtained.

The compound (103) can be converted to the compound (104) by reaction with the compound (5). Reaction of the compound (103) with the compound (5) is carried out in a suitable inert solvent in the presence of a dehydrohalogenating agent. The inert solvent used here includes for example alcohols (e.g. methanol, ethanol, propanol, butanol, 3-methoxy-1-butanol, ethyl cellosolve, methyl cellosolve), ethers (e.g. tetrahydrofuran, diethyl ether), aromatic hydrocarbons (e.g. benzene, toluene, xylene), aprotic polar solvents (e.g. acetone, acetonitrile, dimethylformamide, dimethyl sulfoxide, hexamethylphosphoric acid triamide), halogenated hydrocarbons (e.g. methylene chloride, dichloroethane, chloroform), esters (e.g. methyl acetate, ethyl acetate) and mixtures thereof. The dehydrohalogenating agent used includes common basic compounds, for example organic bases such as triethylamine, trimethylamine, pyridine, dimethylaniline, N-methylmorpholine, 4-dimethylaminopyridine, 4-(1-pyrrolidinyl)pyridine, DBN, DBU, DABCO, sodium acetate, etc., inorganic bases such as potassium carbonate, sodium carbonate, potassium hydrogencarbonate, sodium hydrogencarbonate, potassium hydroxide, sodium hydroxide, sodium hydride, potassium hydride, sodium amide, etc., and alkali metal alcoholates such as sodium methylate, sodium ethylate, etc. The amount of the compound (5) based on the compound (103) is generally at least an equimolar amount, preferably, from an equimolar amount to 3 times by mole. In this case, the compound (5) may be used in excess to make it act as the dehydrohalogenating agent. Said reaction is carried out at a temperature of, generally, from about 0° to about 120° C., preferably from room temperature to 100° C., and generally, it comes to an end in from about 0.5 to about 10 hours. Thus, the compound (104) is obtained.

Reaction process formula-3

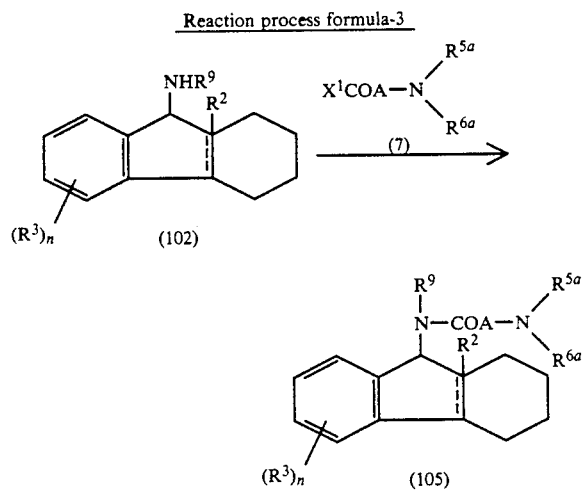

wherein $R^2$, $R^3$, $R^{5a}$, $R^{6a}$, A, n, $X^1$ and the 4a-9a bond of the hydrofluorenone skeleton are the same as defined above; and $R^9$ is the same as defined below.

Reaction of the compound (102) with the compound (6) can be carried out under the same condition as in the foregoing reaction of the compound (102) with the compound (4).

atom as a substituent or pyridylcarbonyl group, and $R^9$ represents a

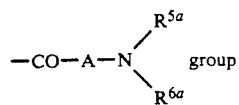

or the foregoing $R^5$ except a lower alkanoyl group which may have a halogen atom as a substituent or pyridylcarbonyl group.

Reaction of the compound of the general formula (106) with the compound of the general formula (7) is attained by subjecting the compounds to the usual amide bond-forming reaction. In this case, the carboxylic acid (7) may be an activated compound. For forming the amide bond, the condition of the common amide bond forming reaction may be applied. For example, the following methods can be employed:

(a) a mixed acid anhydride method wherein the carboxylic acid (7) is reacted with an alkylhalocarboxylic acid to obtain a mixed acid anhydride which is then reacted with the compound (106), (b) an active ester or active amide method wherein the carboxylic acid (7) is converted to an active ester such as for example p-nitrophenyl ester, N-hydroxysuccinimide ester, 1-hydroxybenzotriazole ester, etc., or to an active amide with benzoxazoline-2-thione, and the resulting ester or amide is reacted with the compound (106), (c) a carbodiimide method wherein the carboxylic acid (7) and the compound (106) are condensed with each other in the presence of a dehydrating agent such as for example dicyclohexylcarbodiimide, carbonyldiimidazole, etc.;

(d) a carboxylic acid halide method wherein the carboxylic acid (7) is converted to its halide which is then reacted with the compound (106), and (e) other methods such as a method wherein the carboxylic acid (7) is converted to its anhydride by means of a dehydrating agent such as for example acetic acid anhydride, etc., and the resulting anhydride is then reacted with the compound (106), and a method wherein the carboxylic acid (7) is converted to its ester with, for example, a lower alcohol, and the resulting ester is then reacted with the compound (106) under high pressure and high temperature. Further, there may also be employed a method wherein the carboxylic acid (7) is activated with a phosphorus compound such as triphenyl phosphine, diethyl chlorophosphate, etc., and the resulting activated compound is then reacted with the compound (106).

The alkylhalocarboxylic acid used in the mixed acid anhydride method includes for example methyl chloro- Reaction process formula-4

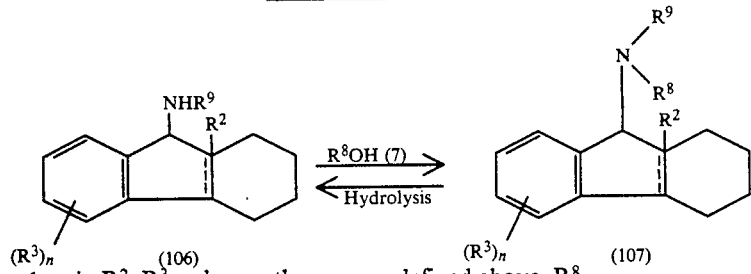

wherein $R^2$, $R^3$ and n are the same as defined above, $R^8$ represents a lower alkanoyl which may have a halogen formate, methyl bromoformate, ethyl chloroformate, ethyl bromoformate, isobutyl chloroformate, etc. The mixed acid anhydride is obtained by the usual Schotten-Bauman reaction, and the anhydride obtained is reacted with the compound (106) without being usually separated to obtain the compound (107). The Schotten-Bauman reaction is generally carried out in the presence of a basic compound. The basic compound used is a compound commonly used in the Schotten-Bauman reaction, and it includes for example organic bases such as triethylamine, trimethylamine, pyridine, dimethylaniline, N-methylmorpholine, 4-dimethylaminopyridine, DBN, DBU, DABCO, etc., and inorganic bases such as potassium carbonate, sodium carbonate, potassium hydrogencarbonate, sodium hydrogencarbonate, etc. Said reaction is carried out at a temperature of from about −20° to about 100° C., preferably from 0° to 50° C. The reaction time is from about 5 minutes to about 10 hours, preferably from 5 minutes to 2 hours. Reaction of the mixed acid anhydride with the compound (106) is carried out at a temperature of from about −20° to about 150° C., preferably from 10° to 50° C. for about 5 minutes to about 10 hours, preferably from about 5 minutes to about 5 hours. The mixed acid anhydride method does not need particularly a solvent, but generally, it is carried out in a solvent. The solvent used may be any of those which are customarily used in the mixed acid anhydride method, and specifically, it includes halogenated hydrocarbons (e.g. methylene chloride, chloroform, dichloroethane), aromatic hydrocarbons (e.g. benzene, toluene, xylene), ethers (e.g. diethyl ether, diisopropyl ether, tetrahydrofuran, dimethoxyethane), esters (e.g. methyl acetate, ethyl acetate), aprotic polar solvents (e.g. dimethylformamide, dimethyl sulfoxide, hexamethylphosphoric acid triamide), etc. The amounts of the carboxylic acid (7), alkyl-halocarboxylic acid and compound (106) are generally at least equimolar with one another, but preferably, the amounts of the alkyl-halocarboxylic acid and compound (106) are each 1 to 2 times by mole based on the carboxylic acid (7).

Referring to the above active ester or active amide method shown in (b) with reference to a case wherein for example benzoxazoline-2-thioneamide is used, it is carried out at a temperature of from 0° to 150° C., preferably from 10° to 100° C. for from 0.5 to 75 hours using a suitable solvent not affecting the reaction, for example 1-methyl-2-pyrrolidone, etc. in addition to the same solvent as used in the foregoing mixed acid anhydride method. In this case, the amount of benzoxazoline-2-thioneamide based on the compound (106) is generally at least an equimolar amount, preferably from an equimolar amount to 2 times by mole. When N-hydroxysuccinimide ester is used, the reaction proceeds advantageously by using a suitable base, for example the same base as used in the carboxylic acid halide method described later.

The above carboxylic acid halide method shown in (c) is carried out by reacting the carboxylic acid (7) with a halogenating agent to obtain a carboxylic acid halide and then reacting the resulting halide, either after separated and purified or without being separated and purified, with the compound (106). Reaction of the carboxylic acid halide with the compound (106) is carried out in a suitable solvent in the presence of a dehydrohalogenating agent. For the dehydrohalogenating agent, basic compounds are generally used, and they include, in addition to the basic compounds used in the above Schotten-Bauman reaction, sodium hydroxide, potassium hydroxide, sodium hydride, potassium hydride, silver carbonate, alkali metal alcoholates (e.g. sodium methylate, sodium ethylate), etc. In this case, the compound (106) may be used in excess to make it act as the dehydrohalogenating agent. The solvent used includes, in addition to the solvents used in the above Schotten-Bauman reaction, water, alcohols (e.g. methanol, ethanol, propanol, butanol, 3-methoxy-1-butanol, ethyl cellosolve, methyl cello-solve), pyridine, acetone, acetonitrile and mixtures of two or more of them. The ratio of the amounts of the compound (106) and carboxylic acid halide used is not particularly limited, but selected from a wide range, and the amount of the latter is generally at least an equimolar amount, preferably from an equimolar amount to 3 times by mole based on the former. The reaction temperature is generally from about −30° to about 180° C., preferably from about 0° to about 150° C., and generally, the reaction comes to an end in from 5 minutes to 30 hours. The carboxylic acid halide used is produced by reacting the carboxylic acid (7) with a halogenating agent with or without a solvent. The solvent may be any of those giving no adverse effect on the reaction, and it includes for example aromatic hydrocarbons (e.g. benzene, toluene, xylene), halogenated hydrocarbons (e.g. chloroform, methylene chloride, carbon tetrachloride), ethers (e.g. dioxane, tetrahydrofuran, diethyl ether), dimethylformamide, dimethyl sulfoxide, etc. For the halogenating agent, the usual ones capable of converting the hydroxyl group of a carboxy group to halogen can be used, and they include for example thionyl chloride, phosphorus oxychloride, phosphorus oxybromide, phosphorus pentachloride, phosphorus pentabromide, etc. The ratio of the amounts of the carboxylic acid (7) and halogenating agent is not particularly limited, but selected from a wide range. When the reaction is carried out without a solvent, the latter is generally used in large excess of the former, and when the reaction is carried out with a solvent, the amount of the latter is generally at least about an equimolar amount, preferably from 2 to 4 times by mole based on the former. The reaction temperature and reaction time are not particularly limited. Generally, however, the former is from about room temperature to about 100° C., preferably from 50° to 80° C., and the latter is from about 30 minutes to about 6 hours.

The method wherein the carboxylic acid (7) is activated with a phosphorus compound such as triphenyl phosphine, diethyl chlorophosphate, etc. and then reacted with the compound (106), is carried out in a suitable solvent. The solvent may be any of those not affecting the reaction, and specifically, it includes halogenated hydrocarbons (e.g. methylene chloride, chloroform, dichloroethane), aromatic hydrocarbons (e.g. benzene, toluene, xylene), ethers (e.g. diethyl ether, tetrahydrofuran, dimethoxyethane), esters (e.g. methyl acetate, ethyl acetate), aprotic polar solvents (e.g. dimethylformamide, dimethyl sulfoxide, hexamethylphosphoric acid triamide), etc. In said reaction, since the compound (106) acts as a basic compound in itself, the reaction well proceeds by using the compound in excess of the theoretical amount. If necessary, however, there may also be used other basic compounds, for example organic bases such as for example triethylamide, trimethylamine, pyridine, dimethylaniline, N-methylmorpholine, 4-dimethylaminopyridine, DBN, DBU, DABCO, etc., and inorganic bases such as potassium carbonate, sodium carbonate, potassium hydrogencarbonate, sodium hydrogencarbonate, etc. Said reaction is attained by carrying it out at a temperature of from about 0° to 150° C., preferably from about 0° to about 100° C. for from about 1 to about 30 hours. Any of the amounts of the phosphorus compound and carboxylic acid (7) based on the compound (106) is generally at least about an equimolar amount, preferably from 1 to 3 times by mole.

To the hydrolysis of the compound of the general formula (107) may be applied any of the usual hydrolysis conditions, and specifically, the hydrolysis is carried out in a solvent in the presence of a basic compound or an acid. The basic compound includes sodium hydroxide, potassium hydroxide, barium hydroxide, etc.; the acid includes mineral acids (e.g. sulfuric acid, hydrochloric acid, nitric acid) and organic acid (e.g. acetic acid, aromatic sulfonic acids); and the solvent includes water, alcohols (e.g. methanol, ethanol, isopropanol), ketones e.g. acetone, methyl ethyl ketone), ethers (e.g. dioxane, ethylene glycol, dimethyl ether), acetic acid and mixtures thereof. Said reaction proceeds at a temperature of, generally, from room temperature to 200° C., preferably from the vicinity of 50° to the vicinity of 150° C., and generally it comes to an end in from about 0.5 to about 6 hours. Thus, the compound of the general formula (106) is obtained.

Reaction process formula-5

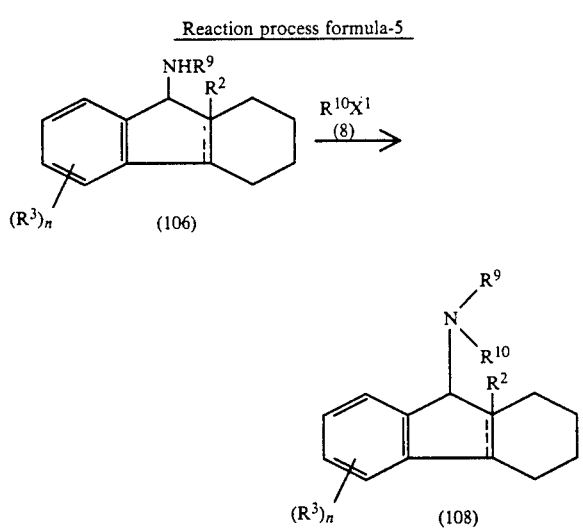

wherein $R^2$, $R^3$, $R^9$, n and $X^1$ are the same as defined above; $R^{10}$ represents a cycloalkyl group, lower alkenyl group, lower alkynyl group, phenyl lower alkyl group, $C_1$-$C_8$ alkyl group which may have a hydroxyl group as a substituent, piperidinyl group which may have a phenyl lower alkyl group as a substituent, piperidinyl lower alkyl group which may have a phenyl lower alkyl group as a substituent, or pyrrolidinyl lower alkyl group which may have a lower alkyl group as a substituent.

Reaction of the compound (106) with the compound (8) can be carried out under the same condition as in the foregoing reaction of the compound (102) with the compound (4).

Reaction process formula-6

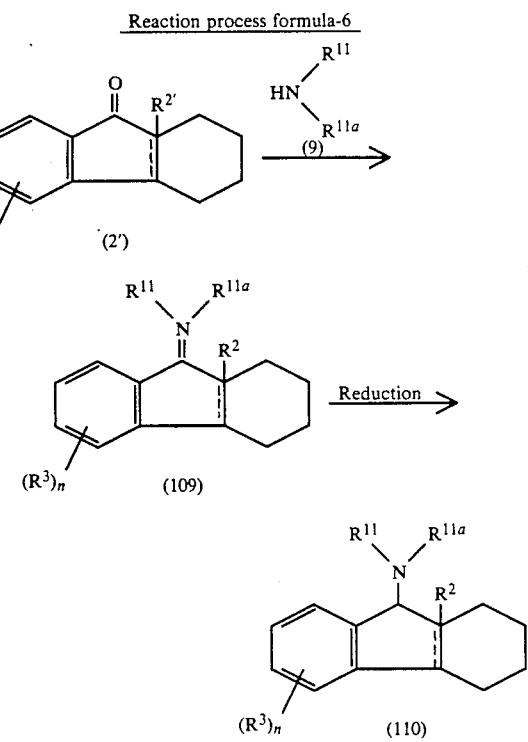

wherein $R^{2'}$ represents a halogen atom or $R^2$ described above; $R^2$, $R^3$ and n are the same as defined above; $R^{11}$ represents a cycloalkyl group, lower alkenyl group, lower alkynyl group, phenyl group, phenyl lower alkyl group, $C_1$-$C_8$ alkyl group which may have a hydroxyl group as a substituent, piperidinyl group which may have a phenyl lower alkyl group as a substituent, piperidinyl lower alkyl group which may have a phenyl lower alkyl group as a substituent or pyrrolidinyl lower alkyl group which may have a lower alkyl group as a substituent; and $R_2^{11}$ represents a hydrogen atom or $R^{11}$ described above, or $R^{11}$ and $R_a^{11}$, together with the nitrogen atom with which they have been bonded, may form a saturated 5- or 6-membered heterocyclic ring which may or may not contain a nitrogen or oxygen atom and may have an oxo group as a substituent.

Reaction of the compound of the general formula (2') with the compound of the general formula (9) is carried out without a solvent or in a suitable solvent in the presence or absence of a dehydrating agent. The solvent used here includes for example alcohols (e.g. methanol, ethanol, isopropanol), aromatic hydrocarbons (e.g. benzene, toluene, xylene), halogenated hydrocarbons (e.g. dichloromethane, dichloroethane, chloroform, carbon tetrachloride), aprotic polar solvents (e.g. dimethylformamide, dimethylacetamide, N-methylpyrrolidone) and mixtures thereof. The dehydrating agent includes for example dryers used to dehydrate the usual solvents (e.g. molecular sieve), mineral acids (e.g. hydrochloric acid, sulfuric acid, boron trifluoride), organic acids (e.g. p-toluenesulfonic acid), etc. Said reaction is carried out at a temperature of, generally, from room temperature to 250° C., preferably from about 50° to about 200° C., and generally, it comes to an end in from about 1 to about 120 hours. The amount of the compound of the general formula (9) is not particularly limited, but it is generally at least an equimolar amount, preferably from an equimolar amount to large excess based on the compound of the general formula (2′). The dehydrating agent is generally used in large excess when it is the dryer, and in a catalytic amount when it is the acid. The compound of the general formula (109) thus obtained may be used for the subsequent reduction without being separated. In the case of the compound of the general formula (109) wherein $R_a{}^{11}$ represents $R^{11}$, the compound is used for the subsequent reduction without being separated from the reaction system.

Various methods may be used for reduction of the compound of the general formula (109). For example, the foregoing condition for reducing the compound of the general formula (101) can be made use of, but preferably, a reduction method with a hydride reducing agent is used. The hydride reducing agent used includes for example lithium aluminum hydride, sodium borohydride, diborane, etc. The amount of the hydride reducing agent is generally at least an equimolar amount, preferably from an equimolar amount to 15 times by mole based on the compound (109). This reduction is generally carried out in a suitable solvent at a temperature of, generally, from about −60° to about 150° C., preferably from −30° to 100° C. for about 10 minutes to about 5 hours. The solvent includes for example water, lower alcohols (e.g. methanol, ethanol, isopropanol), ethers (e.g. tetrahydrofuran, diethyl ether, diisopropyl ether, diglyme) and mixtures thereof. When lithium aluminum hydride or diborane is used as the reducing agent, it is desirable to use a non-aqueous solvent such as diethyl ether, diisopropyl ether, tetrahydrofuran, diglyme, etc. In the reaction of the compound of the general formula (2′) with the compound of the general formula (9), when $R^{2'}$ represents a halogen atom and besides an alcohol is used as the solvent, a compound of the general formula (109) wherein $R^{2'}$ has been converted to a lower alkoxy group is sometimes obtained.

$(R^3a)$s represents a halogen atom, n′ represents an integer of from 0 to 2, and n″ represents an integer of from 1 to 3.

Halogenation of the compound of the general formula (111) is carried out in the presence of the usual halogenating agent. For the halogenating agent used in this reaction, the well-known ones can widely be used, and for example, there may be given halogenating agents such as hydrohalogenic acids (e.g. hydrobromic acid, hydrochloric acid), halogen atoms (e.g. bromine, chlorine), iodine monochloride, surfuryl chloride, N-halogenosuccinimides (e.g. N-bromosuccinimide, N-chlorosuccinimide), dioxane-bromine complex, etc. A desirable amount of the halogenating agent used is generally equimolar with the compound of the general formula (111). The solvent used in said reaction includes for example halogenated hydrocarbons (e.g. dichloromethane, dichloroethane, chloroform, carbon tetrachloride), acetic acid, propionic acid, water, etc. In said reaction, the reaction temperature is generally from 0° C. to the boiling point of the reaction solvent, preferably from 0° to 120° C., and generally, the reaction comes to an end in about 0.5 to about 10 hours.

Reaction process formula-8

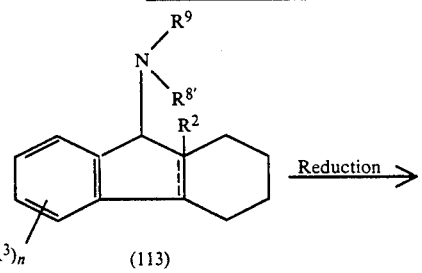

Reaction process formula-7

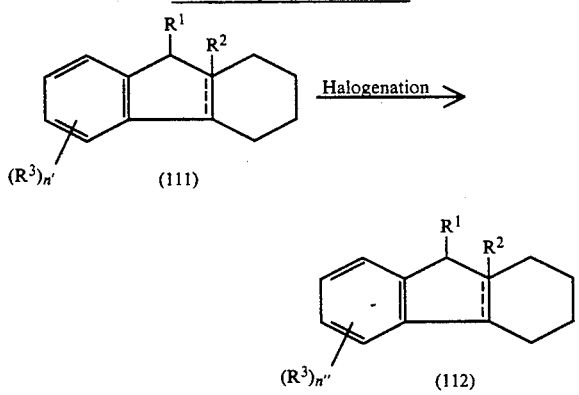

wherein $R^1$, $R^2$ and $R^3$ are the same as defined above, $R^3a$ is the same as $R^3$, provided that at least one of wherein $R^2$, $R^3$, $R^9$ and n are the same as defined above, $R^{8'}$ represents a lower alkanoyl group, and $R^{12}$ represents a lower alkyl group.

Reduction of the compound of the general formula (113) can be carried out under the same condition as in the foregoing reduction of the compound of the general formula (109).

Reaction process formula-9

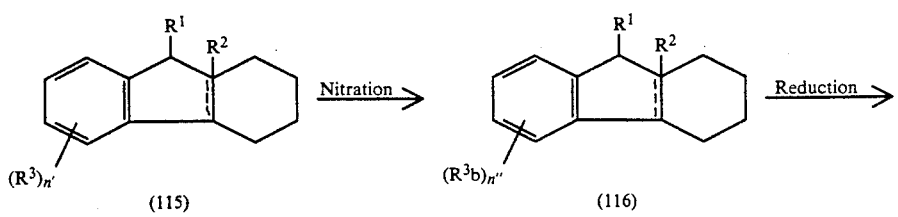

-continued
Reaction process formula-9

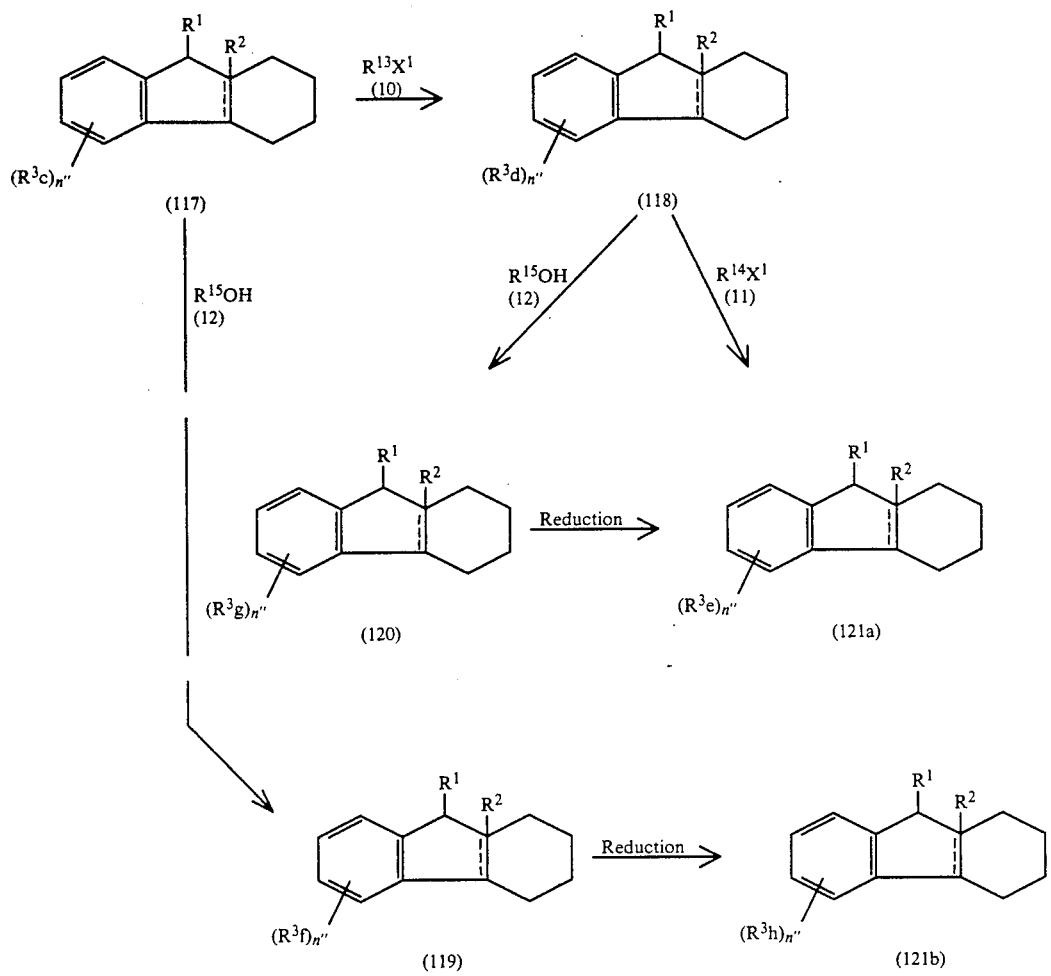

wherein $R^1$, $R^2$, $R^3$, n', n" and $X^1$ are the same as defined above; $R^{13}$ and $R^{14}$ each represents a lower alkyl group; $R^{15}$ represents a lower alkanoyl group; and each of $R^3b$, $R^3c$, $R^3d$, $R^3e$, $R^3f$, $R^3g$ and $R^3h$ represents $R^3$ described above, provided that at least one of ($R^3b$)s represents a nitro group, at least one of ($R^3c$)s represents an amino group, at least one of ($R^3d$)s represents a

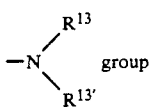

(wherein $R^{13'}$ represents a hydrogen atom or a lower alkyl group), at least one of ($R^3e$)s represents a

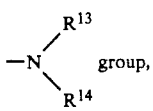

at least one of ($R^3f$)s represents a $-NHR^{15}$ group (wherein $R^{15}$ is the same as defined above), at least one of ($R^3g$)s represents a

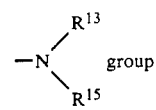

(wherein $R^{13}$ and $R^{15}$ are the same as defined above), and at least one of ($R^3h$)s represents a $-NHR^{16}$ group (wherein $R^{16}$ represents a lower alkyl group).

Nitration of the compound of the general formula (115) is carried out under a condition for nitrating the usual aromatic compounds, for example without a solvent or in a suitable inert solvent using a nitrating agent. The inert solvent includes for example acetic acid, acetic acid anhydride, conc. sulfuric acid, etc., and the nitrating agent includes for example fuming nitric acid, conc. nitric acid, mixed acids (e.g. combination of nitric acid with sulfuric acid, fuming sulfuric acid, phosphoric acid or acetic acid anhydride) and combination of sulfuric acid with an alkali metal nitrate (e.g. potassium nitrate, sodium nitrate). The amount of the nitrating agent is an equimolar amount or more based on the compound which is a raw material, but generally, excessive amounts are used. The reaction is advantageously carried out at from the vicinity of 0° C. to the vicinity of room temperature for from 1 to 4 hours.

Reduction of the compound of the general formula (116) can be carried out under the same condition as in the reduction of the compound of the general formula (101) shown in the foregoing Reaction process formula-1.

Reduction of the compound of the general formula (116) can also be carried out using a reducing agent described below. The reducing agent used includes for example combination of iron, zinc, tin or stannous chloride with an acid (e.g. acetic acid, hydrochloric acid, sulfuric acid), and combination of iron, ferrous sulfate, zinc or tin with an alkali metal hydroxide (e.g. sodium hydroxide), a sulfide (e.g. ammonium sulfide), aqueous ammonia or an ammonium salt (e.g. ammonium chloride). The inert solvent used here includes for example water, methanol, ethanol, dioxane, etc. The reduction condition is properly selected according to the kind of the reducing agent used, and for example, when combination of stannous chloride and hydrochloric acid is used as a reducing agent, it is advantageous to carry out the reduction at from the vicinity of 0° to the vicinity of room temperature for about 0.5 to about 10 hours. The amount of the reducing agent is at least an equimolar amount based on the compound which is a raw material, and generally, it is from an equimolar amount to 5 times by mole based on the same compound.

Reaction of the compound of the general formula (117) with the compound of the general formula (10) and that of the compound of the general formula (118) wherein $R^{13'}$ is a hydrogen atom with the compound of the general formula (11) can be carried out under the same condition as in the reaction of the compound of the general formula (106) with the compound of the general formula (8) shown in the foregoing Reaction process formula-5. In said reaction, when $R^1$ in the general formula (117) and in the general formula (118), represents a —$NHR^9$ group (wherein $R^9$ is the same as defined above), and $R^1$ in the general formula (118) represents a —B—$NHR^{29}$ group (wherein B is the same as defined above and $R^{29}$ is the same as defined Later),

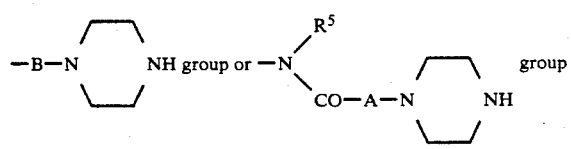

(wherein $R^5$ and A are the same as defined above), the compounds (117) and (118), by reaction with the compounds of the general formulae (10) and (11), respectively, sometimes produce the compound of the general formula (118) wherein $R^1$ represents a

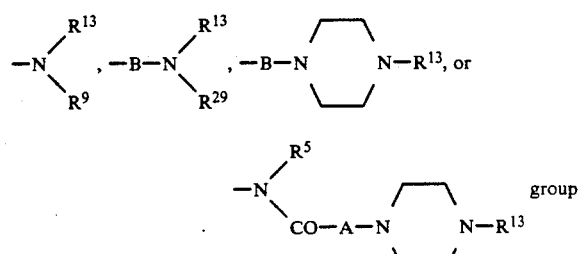

and the compound of the general formula (121a) wherein $R^1$ represents a

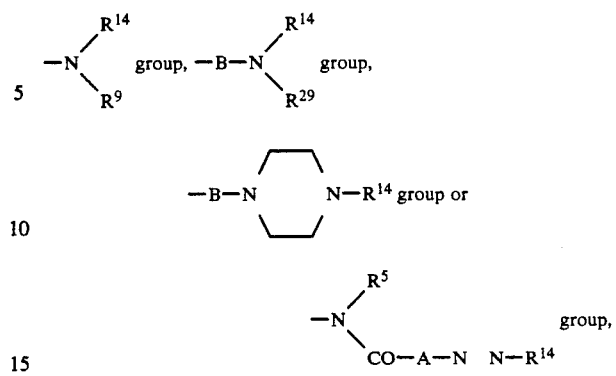

respectively. Separation of these compounds is however easily possible.

Reaction of the compound of the general formula (117) with the compound of the general formula (12) and that of the compound of the general formula (118) wherein $R^{13'}$ is a hydrogen atom with the compound of the general formula (12) can be carried out under the same condition as in the reaction of the compound of the general formula (106) with the compound of the general formula (7) shown in the foregoing Reaction process formula-4. In said reaction, when $R^1$ in the compounds of the general formulae (117) and (118) represents a —$NHR^9$ group (wherein $R^9$ is the same as defined above), the compounds (117) and (118), by reaction with the compound of the general formula (12), sometimes produce the compounds of the general formulae (119) and (120), respectively, wherein $R^1$ represents a

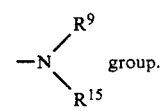

Separation of these compounds is however easily possible.

Reduction of the compounds of the general formulae (119) and (120) can be carried out under the same condition as in the reduction of the compound of the general formula (113) shown in the foregoing Reaction process formula-8. In said reaction, when $R^1$ in the compounds of the general formulae (119) and (120) represents a

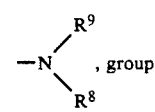

(wherein $R^9$ and $R^{8'}$ are the same as defined above), the compounds (119) and (120) are reduced to sometimes produce the compounds of the general formulae (121a) and (121b), respectively, wherein $R^1$ represents a

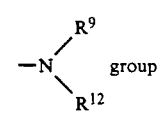

(wherein $R^9$ and $R^{12}$ are the same as defined above). Separation of these compounds is however easily possible.

In the foregoing Reaction process formula-1, the compound of the general formula (2) used as a starting compound includes a novel compound, and it is produced, for example, by the following method.

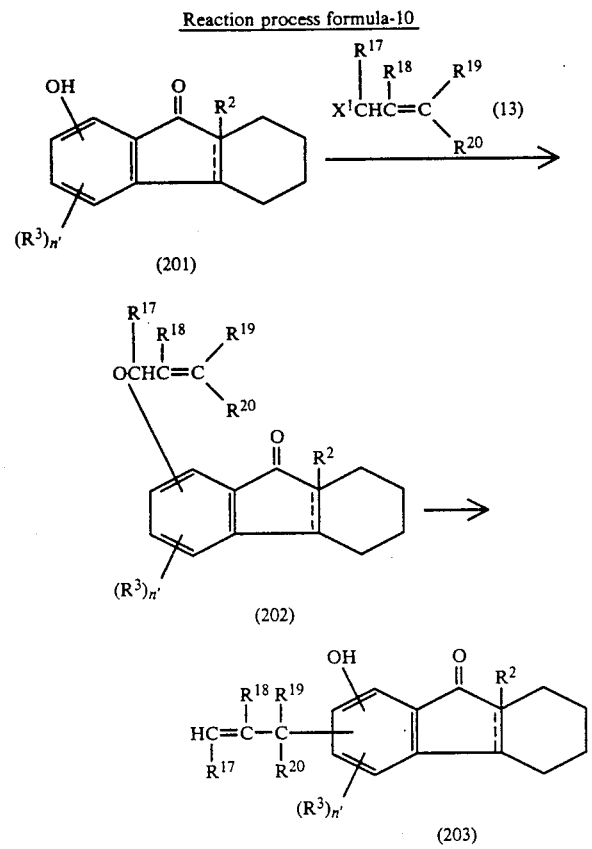

Reaction process formula-10 wherein $R^2$, $R^3$, n' and $X^1$ are the same as defined above, and $R^{17}$, $R^{18}$, $R^{19}$ and $R^{20}$ are each a hydrogen atom, a lower alkyl group or a phenyl group, and $R^{17}$ and $R^{20}$ may be bonded with each other to form a cycloalkenyl group.

Reaction of the compound of the general formula (201) with the compound of the general formula (13) is carried out in the presence of a basic compound. For the basic compound, the well-known ones can widely be used, and they include for example inorganic bases (e.g. sodium hydride, sodium hydroxide, potassium hydroxide, sodium carbonate, potassium carbonate, sodium hydrogencarbonate, potassium hydrogencarbonate, silver carbonate), alkali metals (e.g. sodium, potassium), alcoholates (e.g. sodium methylate, sodium ethylate) and organic bases (e.g. triethylamine, pyridine, N,N-dimethylaniline, N-methylmorpholine, 4-dimethylaminopyridine, DBN, DBU, DABCO). Said reaction is carried out with or without a solvent. For the solvent, all the inert solvents giving no adverse effect on the reaction can be used, and they include for example water, alcohols (e.g. methanol, ethanol, propanol, butanol, ethylene glycol), ethers (e.g. diethyl ether, tetrahydrofuran, dioxane, monoglyme, diglyme), ketones (e.g. acetone, methyl ethyl ketone), aromatic hydrocarbons (e.g. benzene, toluene, xylene), esters (e.g. methyl acetate, ethyl acetate), aprotic polar solvents (e.g. N,N-dimethylformamide, dimethyl sulfoxide, hexamethylphosphoric acid triamide) and mixtures thereof. Also, it is advantageous to carry out said reaction in the presence of a metal iodide such as sodium iodide, potassium iodide, etc. The ratio of the amounts of the compound of the general formula (201) and the compound of the general formula (13) in the above method is not particularly limited, but properly selected from a wide range. However, the amount of the latter is generally from an equimolar amount to 5 times by mole, preferably from an equimolar amount to 2 times by mole based on the former. The reaction temperature is not particularly limited, and it is generally from room temperature to 200° C., preferably from room temperature to 150° C. The reaction time is generally from 1 to 30 hours, preferably from 1 to 15 hours.

The reaction to obtain the compound of the general formula (203) from that of the general formula (202) is generally called Claisen reaction, and for example, the compound (202) can be converted to the compound (203) by heating in a suitable solvent. The solvent used includes high-boiling solvents such as dimethylformamide, tetralin, etc. The heating temperature is generally from 100° to 250° C., preferably from about 150° to about 250° C., and said reaction comes to an end in from about 1 to about 50 hours.

Reaction process formula-11

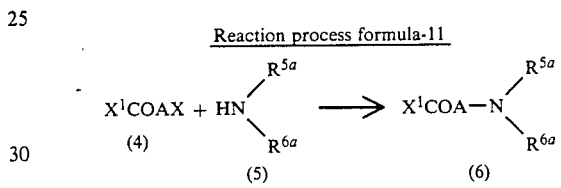

wherein X, $X^1$, $R^{5a}$, $R^{6a}$ and A are the same as defined above.

Reaction of the compound of the general formula (4) with the compound of the general formula (5) can be carried out under the same condition as in the reaction of the compound of the general formula (102) with the compound of the general formula (4) shown in the foregoing Reaction process formula-2.

Reaction process formula-12

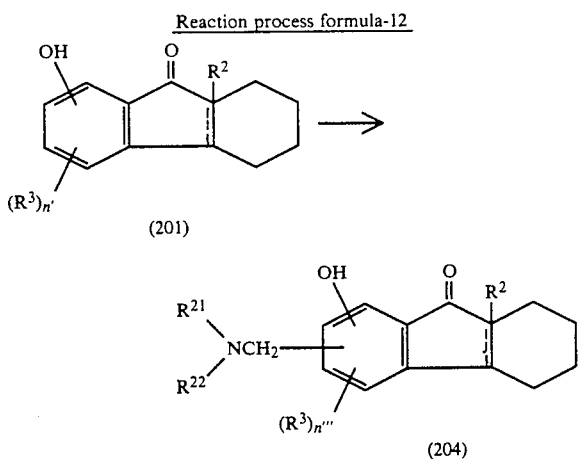

wherein $R^2$, $R^3$ and n' are the same as defined above, $R^{21}$ and $R^{22}$, which may be the same or different, represent a hydrogen atom or a lower alkyl group, and n''' represents 0 or 1.

A method to convert the compound of the general formula (201) to the compound of the general formula (204) can be attained: (1) by reacting the compound (201) with, for example,

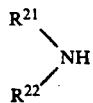 (14)

(wherein $R^{21}$ and $R^{22}$ are the same as defined above) and formaldehyde (Mannich reaction) or (2) by reacting the compound (201) with

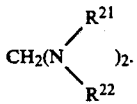 (15)

The method (1) is carried out by reacting the compound of the general formula (201), the compound of the general formula (14) and formaldehyde in a suitable solvent in the presence of an acid. The solvent used here may be any of those which are commonly used in Mannich reaction, and it includes for example water, alcohols (e.g. methanol, ethanol, isopropanol), alkanoic acids (e.g. acetic acid, propionic acid), acid anhydrides (e.g. acetic acid anhydride), polar solvents (e.g. acetone, dimethylformamide) and mixtures thereof. The acid used includes mineral acids (e.g. hydrochloric acid, hydrobromic acid), organic acids (e.g. acetic acid), etc. For formaldehyde, aqueous solutions containing 20 to 40 wt. % of formaldehyde, trimer, polymer (paraformaldehyde), etc. are usually used.

The amount of the compound of the general formula (14) used is generally at least an equimolar amount, preferably from an equimolar amount to 2 times by mole based on the compound of the general formula (201). The amount of formaldehyde used is at least equimolar with the compound of the general formula (201), but generally, the use of large excess is preferred. Said reaction proceeds at a temperature of, generally, from 0° to 200° C., preferably from the vicinity of room temperature to the vicinity of 150° C., and it comes to an end in from about 0.5 to about 10 hours.

The method (2) is carried out without a solvent or in a suitable solvent in the presence of an acid. The acid used here includes mineral acids (e.g. hydrochloric acid, hydrobromic acid, sulfuric acid), organic acids (e.g. acetic acid, acetic acid anhydride), etc., and among these, acetic acid anhydride is preferred. The solvent used here may be any of those which can be used in the foregoing method (1). The amount of the compound (15) used is generally at least an equimolar amount, preferably from an equimolar amount to 5 times by mole based on the compound of the general formula (201). Said reaction comes to an end at a temperature of, generally, from 0° to 150° C., preferably from the vicinity of room temperature to the vicinity of 100° C. in from about 0.5 to about 5 hours.

Reaction process formula-13

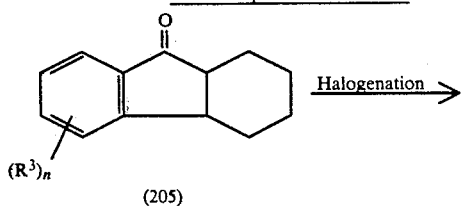

(205)

-continued
Reaction process formula-13

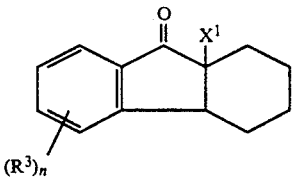

(206)

wherein $R^3$, n and $X^1$ are the same as defined above.

Halogenation of the compound of the general formula (205) can be carried out under the same condition as in the halogenation of the compound of the general formula (111) shown in the foregoing Reaction process formula-7. In this reaction, a compound of the general formula (206) wherein at least one of $(R^3)$s has been substituted with a halogen atom is sometimes obtained, but this compound can easily be separated.

Reaction process formula-14

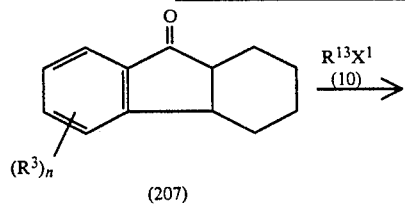

(207)

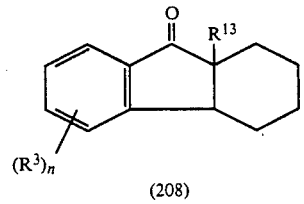

(208)

wherein $R^3$, $R^{13}$, n and $X^1$ are the same as defined above.

Reaction of the compound of the general formula (207) with the compound of the general formula (10) is carried out in a suitable solvent in the presence of a basic compound. For the solvent used here, any solvent not affecting the reaction may be used, and it includes for example water, alcohols (e.g. methanol, ethanol, isopropanol), aromatic hydrocarbons (e.g. benzene, toluene, xylene), ethers (e.g. diethyl ether, tetrahydrofuran, dioxane, diglyme, monoglyme), halogenated hydrocarbons (e.g. dichloromethane, chloroform, carbon tetrachloride), polar solvents (e.g. dimethylformamide, dimethyl sulfoxide, hexamethylphosphoric acid triamide), etc. The basic compound used includes for example inorganic bases (e.g. sodium hydroxide, potassium hydroxide, potassium carbonate, sodium carbonate, potassium hydrogencarbonate, sodium hydrogencarbonate, sodium hydride), metal alcoholates (e.g. sodium ethylate, sodium methylate), organic bases (e.g. 1,5-diazabicyclo[4,3,0]nonene-5, 1,8-diazabicyclo[5,4,0]undecene-7, 1,4-diazabicyclo[2,2,2]octane, triethylamine), etc. The amount of the compound of the general formula (10) used is generally at least an equimolar amount, preferably from an equimolar amount to 3 times by mole based on the compound of the general formula (207). The amount of the basic compound used is generally at least an equimolar amount, preferably from an equimolar amount to 5 times by mole based on the compound of the general formula (207). Said reaction proceeds at a temperature of, generally, from 0° to 150° C., preferably from the vicinity of room temperature to the vicinity of 100° C., and generally, it comes to an end in from about 0.5 to about 15 hours.

When at least one of ($R^3$)s in the compound of the general formula (207) is a hydroxyl group, the compound is alkylated under the reaction condition to sometimes produce a compound of the general formula (208) wherein at least one of ($R^3$)s is a lower alkoxy group. This compound can easily be separated.

Reaction process formula-15

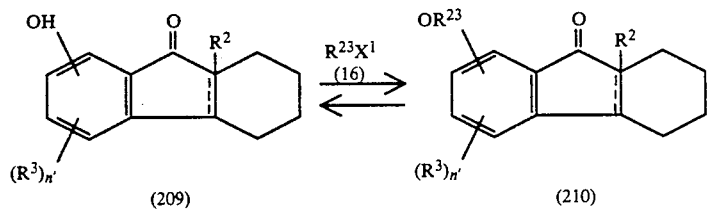

wherein $R^2$, $R^3$, $n'$ and $X^1$ are the same as defined above, and $R^{23}$ represents a lower alkyl group.

Reaction of the compound of the general formula (209) with the compound of the general formula (16) is carried out in a suitable solvent in the presence of a basic compound. For the basic compound used here, there are given for example sodium hydroxide, potassium hydroxide, sodium ethylate, sodium hydride, potassium hydride, sodium amide, potassium amide, etc. in place of the organic bases used in the reaction of the compound of the general formula (102) with the compound of the general formula (4) shown in the foregoing Reaction process formula-2. The solvent includes for example water, alcohols (e.g. methanol, ethanol, isopropanol), ethers (e.g. dioxane, diethylene glycol dimethyl ether), aromatic hydrocarbons (e.g. toluene, xylene), dimethylformamide, dimethyl sulfoxide, hexamethylphosphoric acid triamide, acetonitrile, etc. The amount of the compound of the general formula (16) used is not particularly limited, but properly selected from a wide range. However, the amount is generally at least an equimolar amount, preferably from an equimolar amount to 5 times by mole based on the compound of the general formula (209). Said reaction is carried out at a temperature of, generally, from about 0° to about 70° C., preferably from the vicinity of 0° C. to the vicinity of 50° C., and generally, it comes to an end in from about 0.5 to about 12 hours.

When $R^2$ in the compound of the general formula (209) is a hydrogen atom, the compound, under the reaction condition described above, sometimes produces a compound of the general formula (210) wherein $R^2$ has been substituted with a lower alkyl group, but this compound can easily be separated.

The reaction to convert the compound of the general formula (210) to the compound of the general formula (209) is attained by treating the compound (210) at a temperature of from the vicinity of 0° C. to the vicinity of 100° C. for from about 0.5 to about 3 hours under a hydrogen pressure of from 1 to 10 atm. in the presence of a catalyst for catalytic reduction (e.g. palladium-carbon, palladium black) in a suitable solvent which includes for example water, lower alcohols (e.g. methanol, ethanol, isopropanol), ethers (e.g. dioxane, tetrahydrofuran), acetic acid and mixtures thereof, or by heat-treating the compound (210) at a temperature of from 30° to 150° C., preferably from 50° to 120° C. in a mixed solvent of an acid (e.g. hydrobromic acid, hydrochloric acid) and a solvent (e.g. water, methanol, ethanol, isopropanol). Also, the compound of the general formula (209) can be obtained by hydrolysis of the compound of the general formula (210). This hydrolysis is carried out in a suitable solvent in the presence of an acid or basic compound. The solvent includes for example water, lower alcohols (e.g. methanol, ethanol, isopropanol), ethers (e.g. dioxane, tetrahydrofuran), polar solvents (e.g. acetonitrile) and mixtures thereof. The acid includes for example mineral acids (e.g. hydrochloric acid, sulfuric acid, hydrobromic acid), Lewis acids (e.g. aluminum chloride), iodides (e.g. sodium iodide, potassium iodide) and a mixture of the Lewis acid and iodide. The basic compound includes for example metal hydroxides (e.g. sodium hydroxide, potassium hydroxide, calcium hydroxide), etc. Said reaction proceeds at a temperature of, generally, from room temperature to 150° C., preferably from room temperature to 100° C., and generally, it comes to an end in from about 0.5 to about 15 hours.

Reaction process formula-16

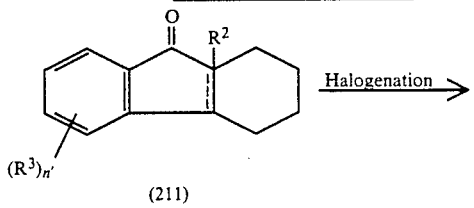

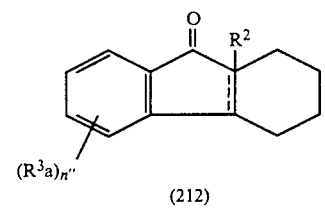

wherein $R^2$, $R^3$, $R^3a$, $n'$ and $n''$ are the same as defined above.

Halogenation of the compound of the general formula (211) can be carried out under the same condition as in the foregoing halogenation of the compound of the general formula (111).

In this reaction, when $R^2$ is the compound of the general formula (211) is a hydrogen atom, and the carbon-carbon bond between 4a- and 9a-positions in the hydrofluorene skeleton is a single bond, then the compound is halogenated to sometimes produce a compound of the general formula (212) wherein $R^2$ has been halogenated. This compound, however, can easily be separated.

Reaction process formula-17

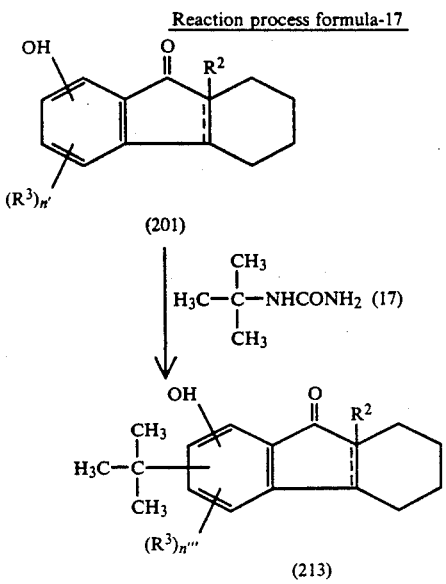

wherein $R^2$, $R^3$, $n'$ and $n'''$ are the same as defined above.

Reaction of the compound of the general formula (201) with N-tert-butylurea of the formula (17) can be carried out in a suitable solvent in the presence of an acid.

The acid used here includes mineral acids (e.g. sulfuric acid), and the solvent includes water, aromatic hydrocarbons (e.g. benzene, toluene, xylene), etc. The amount of N-tert-butylurea (17) used is generally from an equimolar amount to large excess based on the compound of the general formula (201), preferably from an equimolar amount to 10 times by mole based on the same compound (201). Said reaction comes to an end at a temperature of, generally, from room temperature to 200° C., preferably from the vicinity of room temperature to the vicinity of 150° C. in from about 5 to about 20 hours. The above reaction may also be carried out using tert-butanol and urea in place of N-tert-butylurea (17).

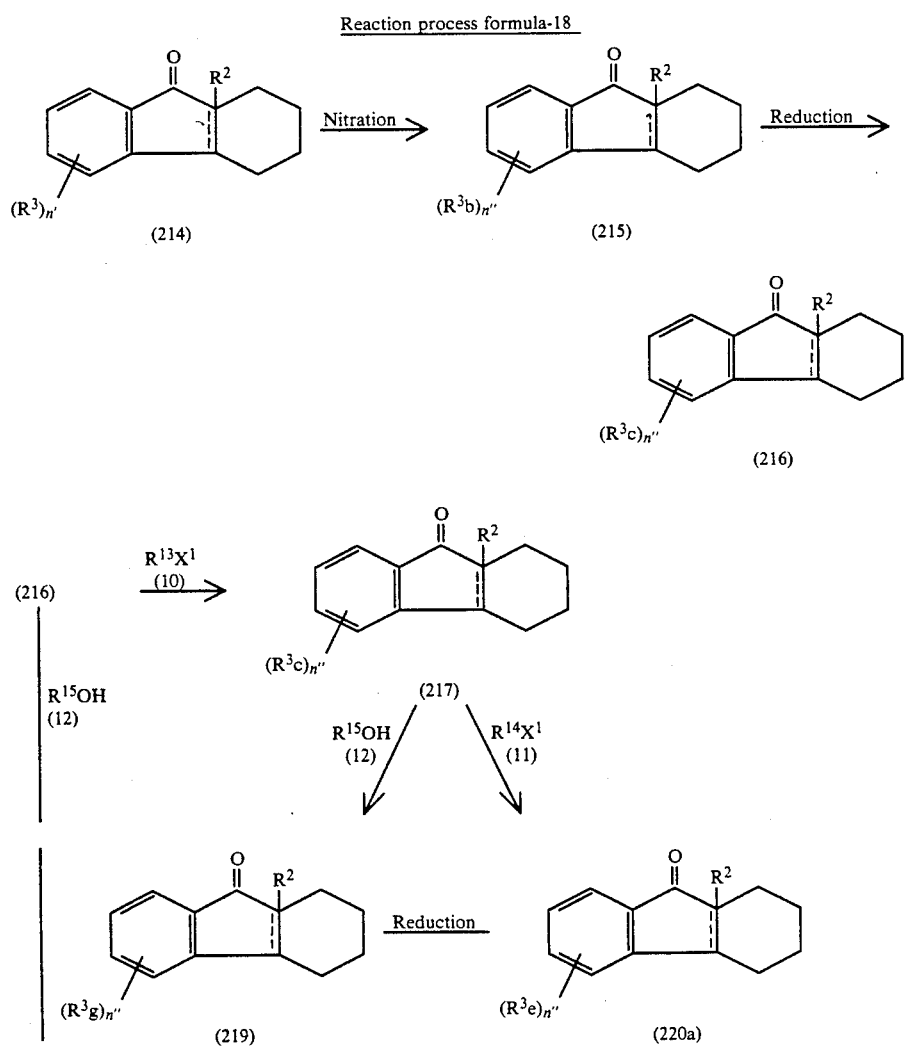

-continued
Reaction process formula-18

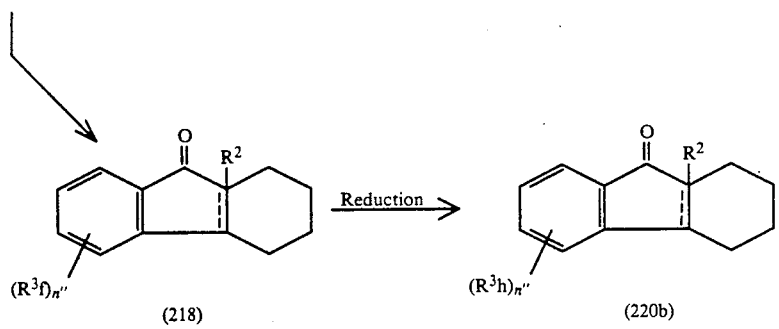

wherein $R^2$, $R^3$, n', n'', $R^{13}$, $X^1$, $R^{14}$, $R^{15}$, $R^3b$, $R^3c$, $R^3d$, $R^3e$, $R^3f$, $R^3g$ and $R^3h$ are the same as defined above.

Nitration of the compound of the general formula (214) can be carried out under the same condition as in the nitration of the compound of the general formula (115) shown in the foregoing Reaction process formula-9. Reduction of the compound of the general formula (215) can similarly be carried out under the same condition as in the foregoing reduction of the compound of the general formula (116).

Reaction of the compound of the general formula (216) with the compound of the general formula (10) and that of the compound of the general formula (217) wherein $R^{13'}$ is a hydrogen atom with the compound of the general formula (11) can be carried out under the same conditions as in the foregoing reaction of the compound of the general formula (117) with the compound of the general formula (10) and reaction of the compound of the general formula (118) wherein $R^{13'}$ is a hydrogen atom with the compound of the general formula (11), respectively.

Reaction of the compound of the general formula (216) with the compound of the general formula (12) and that of the compound of the general formula (217) wherein $R^{13'}$ is a hydrogen atom with the compound of the general formula (12) can be carried out under the same conditions as in the foregoing reaction of the compound of the general formula (117) with the compound of the general formula (12) and reaction of the compound of the general formula (118) wherein $R^{13'}$ is a hydrogen atom with the compound of the general formula (12), respectively.

Reduction of the compounds of the general formulae (218) and (219) can be carried out under the same condition as in the foregoing reduction of the compound of the general formula (120). In said reactions, the carbonyl group at the 9-position is sometimes reduced, but the resulting compounds can easily be separated.

Reaction process formula-19

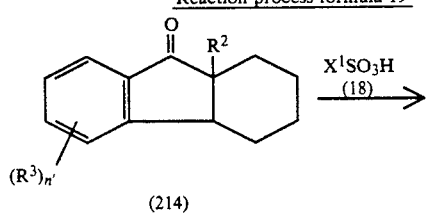

-continued
Reaction process formula-19

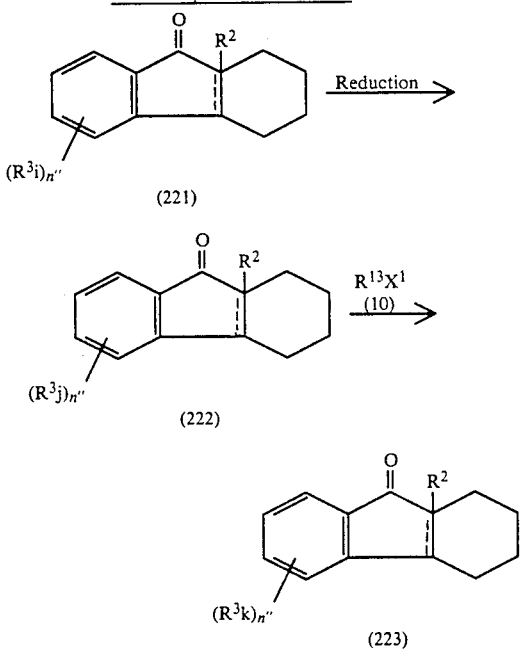

wherein $R^2$, $R^3$, n', n'', $X^1$ and $R^{13}$ are the same as defined above, at least one of ($R^3c$)s represents a —$SO_2X^1$ group, at least one of ($R^3j$)s represents a —SH group, and at least one of ($R^3k$)s represents a —$SR^{13}$ group (wherein $R^{13}$ is the same as defined above).

Reaction of the compound of the general formula (214) with the compound of the general formula (18) is carried out in the presence or absence of a solvent. For the solvent used here, any solvent not affecting the reaction may be used, and it includes for example halogenated hydrocarbons (e.g. chloroform, dichloromethane, carbon tetrachloride) and aromatic hydrocarbons (e.g. benzene, toluene, xylene, nitrobenzene, dichlorobenzene). The amount of the compound of the general formula (18) used is generally at least an equimolar amount, preferably from an equimolar amount to 1.5 times by mole based on the compound of the general formula (214). The reaction proceeds at a temperature of, generally, from −50° to 50° C., preferably from the vicinity of −10° C. to the vicinity of 10° C., and generally, it comes to an end in from about 15 minutes to about 10 hours.

Reduction of the compound of the general formula (221) can be carried out by a method (1) which uses a metal (e.g. iron, zinc, tin, stannous chloride) and an acid (e.g. acetic acid, hydrochloric acid, sulfuric acid) in combination, or a method (2) which uses a hydride reducing agent (e.g. lithium aluminum hydride, sodium borohydride, diborane). When the method (1) is used, it is preferred that the acid is used in large excess, and that the metal is used in an amount at least equimolar with the compound of the general formula (221), generally in large excess of the same compound (221). This reaction is carried out at a temperature of, generally, from −50° to 150° C., preferably from the vicinity of room temperature to the vicinity of 100° C., and generally, it comes to an end in from about 0.5 to about 10 hours. When the method (2) is used, there can be used the same condition as in the reduction of the compound of the general formula (109) shown in the foregoing Reaction process formula-6.

Reaction of the compound of the general formula (222) with the compound of the general formula (10) is carried out in a solvent in the presence of a dehydrohalogenating agent. For the solvent and dehydrohalogenating agent used here, there can be used those which are used in the reaction of the compound of the general formula (102) with the compound of the general formula (4) shown in the foregoing Reaction process formula-2. Said reaction is carried out at a temperature of, generally, from −50° to 100° C., preferably from about −50° to about 30° C., and generally, it comes to an end in from about 30 minutes to about 5 hours. The amount of the compound of the general formula (10) used is generally at least an equimolar amount, preferably from an equimolar amount to 1.2 times by mole based on the compound of the general formula (222).

The foregoing compounds of the general formulae (201) and (209) include a novel compound and can be produced, for example, by the following method.

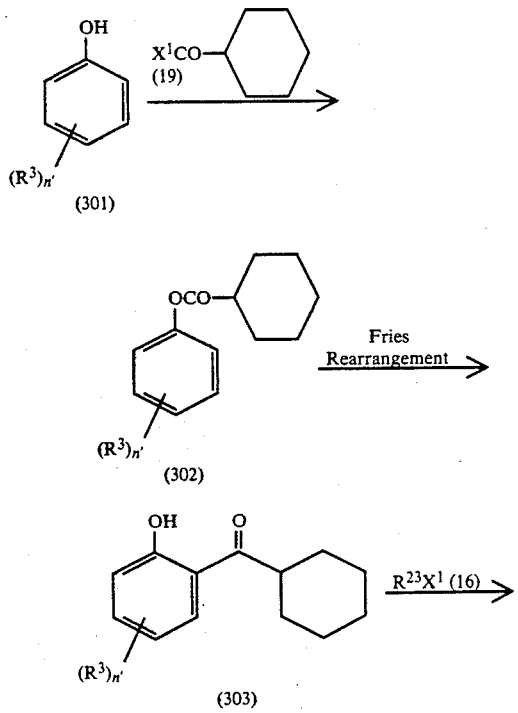

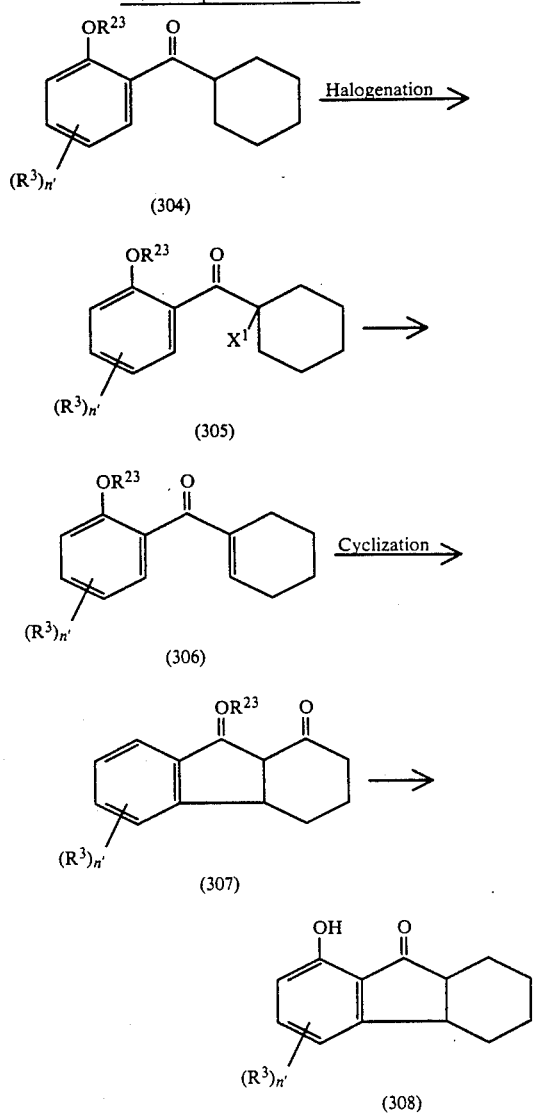

wherein $R^3$, $n'$, $R^{23}$ and $X^1$ are the same as defined above.

Reaction of the compound of the general formula (301) with the compound of the general formula (19) is carried out without a solvent or in a suitable solvent in the presence or absence of a basic compound. For the solvent and basic compound used here, there may be used any of those which are given in the foregoing Reaction process formula-2. The amount of the compound of the general formula (19) used is at least an equimolar amount, preferably from an equimolar amount to 1.5 times by mole based on the compound of the general formula (301).

Said reaction comes to an end at a temperature of, generally, from room temperature to 150° C., preferably from 50° to 130° C. in from about 1 to about 5 hours. The reaction to convert the compound of the general formula (302) to the compound of the general formula (303) is generally called Fries rearrangement, and any of the reaction conditions used in the Fries rearrangement may be used. For example, said reaction can be carried out without a solvent or in a suitable solvent in the presence of a suitable catalyst. The catalyst used here includes Lewis acids such as aluminum chloride, aluminum bromide, zinc chloride, ferric chloride, stannic chloride, boron trifluoride, etc. The solvent used includes for example carbon disulfide, halogenated hydrocarbons (e.g. dichloromethane, dichloroethane, trichloroethane, tetrachloroethane), aromatic hydrocarbons (e.g. nitrobenzene, chlorobenzene), ethers (e.g. dioxane, diethyl ether), etc.

The amount of the catalyst is generally from 2 to 10 times by mole, preferably from 3 to 6 times by mole based on the compound of the general formula (302). Said reaction comes to an end at a temperature of, generally, from room temperature to 150° C., preferably from the vicinity of 90° C. to the vicinity of 150° C. in from about 1 to about 5 hours.

Reaction of the compound of the general formula (303) with the compound of the general formula (16) can be carried out under the same condition as in the reaction of the compound of the general formula (209) with the compound of the general formula (16) shown in the foregoing Reaction process formula-15.

Halogenation of the compound of the general formula (304) can be carried out under the same condition as in the halogenation of the compound of the general formula (111) shown in the foregoing Reaction process formula-7. The reaction to convert the compound of the general formula (305) to the compound of the general formula (306) can be carried out in a suitable solvent in the presence of a dehydrohalogenating agent. The dehydrohalogenating agent used here includes for example lithium salts (e.g. lithium chloride, lithium carbonate), organic bases (e.g. triethylamine, DBU), etc. The solvent used includes esters (e.g. ethyl acetate), etc. in addition to the solvents given in the reaction of the compound of the general formula (102) with the compound of the general formula (4) in the foregoing Reaction process formula-2.

The amount of the dehydrohalogenating agent used is at least an equimolar amount, preferably from an equimolar amount to 5 times by mole based on the compound of the general formula (305).

Said reaction comes to an end at a temperature of, generally, from room temperature to 150° C., preferably from the vicinity of 50° C. to the vicinity of 100° C. in from about 1 to about 5 hours. Cyclization of the compound of the general formula (306) is carried out without a solvent or in a suitable solvent in the presence of an acid. The acid used here includes mineral acids (e.g. hydrochloric acid, sulfuric acid, hydrobromic acid), phosphoric acids (e.g. phosphoric acid, polyphosphoric acid), alkanic acids (e.g. acetic acid, trifluoroacetic acid), organic acids (e.g. p-toluenesulfonic acid), etc. The solvent used here includes for example alcohols (e.g. methanol, ethanol, isopropanol), aromatic hydrocarbons (e.g. benzene, toluene, xylene), halogenated hydrocarbons (e.g. dichloromethane, dichloroethane, chloroform, carbon tetrachloride), ethers (e.g. diethyl ether, tetrahydrofuran, dioxane, diaglyme, monoglyme), polar solvents (e.g. dimethylformamide, dimethyl sulfoxide, hexamethylphosphoric acid triamide), etc. Said reaction proceeds at a temperature of, generally, from 0° to 150° C., preferably from the vicinity of 0° C. to the vicinity of 120° C., and it comes to an end in from about 30 minutes to about 24 hours.

The amount of the acid used is generally large excess, preferably from 7 times by mole to large excess based on the compound of the general formula (306).

The reaction to convert the compound of the general formula (307) to the compound of the general formula (308) can be carried out under the same condition as in the reaction to convert the compound of the general formula (210) to the compound of the general formula (209) shown in the foregoing Reaction process formula -15.

The foregoing compounds of the general formulae (205) and (214) include a novel compound, and they can be produced, for example, by the following method.

Reaction process formula-21

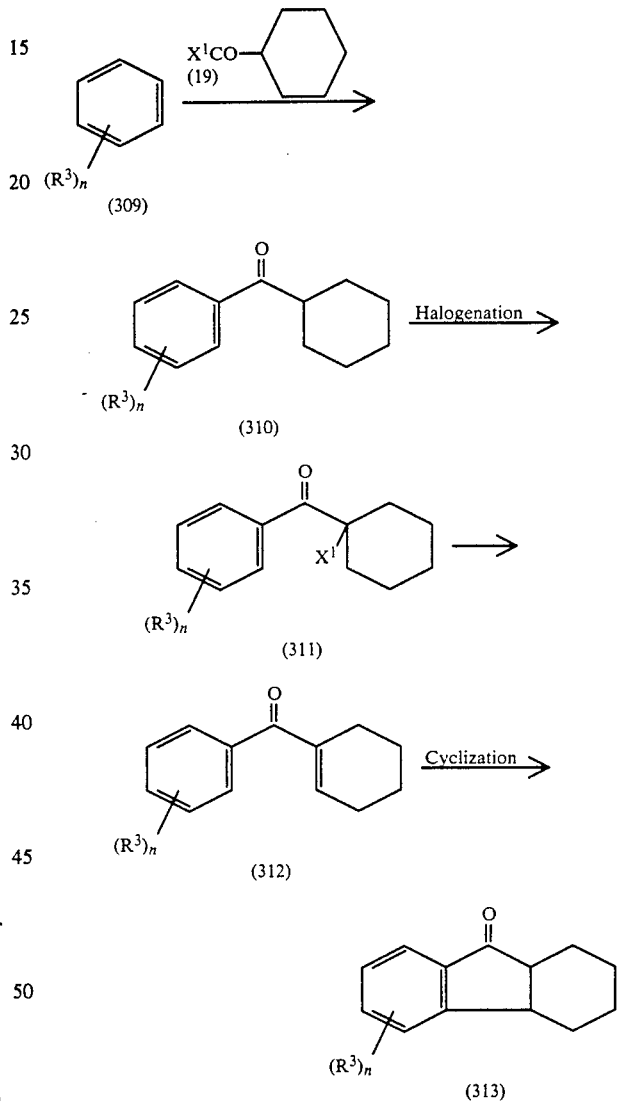

wherein $R^3$, n and $X^1$ are the same as defined above.

Reaction of the compound of the general formula (309) with the compound of the general formula (19) can be carried out without a solvent or in a suitable solvent in the presence of a catalyst. For the solvent and catalyst used here, there may be used any of those which are given in the foregoing reaction to convert the compound of the general formula (302) to the compound of the general formula (303).

The amount of the catalyst used is at least an equimolar amount, preferably from an equimolar amount to 5 times by mole based on the compound of the general formula (309). The amount of the compound of the general formula (19) used is at least an equimolar amount, preferably from an equimolar amount to 2 times by mole based on the compound of the general formula (309).

Said reaction comes to an end at a temperature of, generally, from −30° to 120° C., preferably from the vicinity of −10° C. to the vicinity of 70° C. in from about 0.5 to about 20 hours.

Halogenation of the compound of the general formula (310) can be carried out under the same condition as in the halogenation of the compound of the general formula (304) shown in the foregoing Reaction process formula-20. The reaction to convert the compound of the general formula (311) to the compound of the general formula (312) can be carried out, under the same condition as in the reaction to convert the compound of the general formula (305) to the compound of the general formula (306) shown in the foregoing Reaction process formula-20. Also, cyclization of the compound of the general formula (312) into the compound of the general formula (313) can be carried out under the same condition as in the cyclization of the compound of the general formula (306) into the compound of the general formula (307) shown in the foregoing Reaction process formula-20.

When $R^1$ in the compound of the general formula (122) represents a $-NHR^9$ group (wherein $R^9$ is the same as defined above), $-B-NHR^{29}$ group (wherein B is the same as defined above, and $R^{29}$ is the same as defined later),

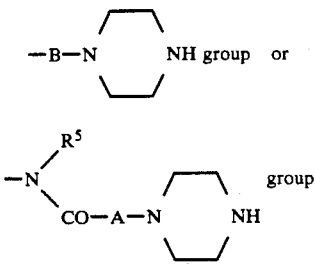

(wherein $R^5$ and A are the same as defined above), the compound of the general formula (122), by reaction with $R^{23}X^1$, sometimes produces a compound of the general formula (123) wherein $R^1$ is a

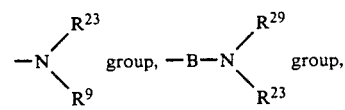

Reaction process formula-22

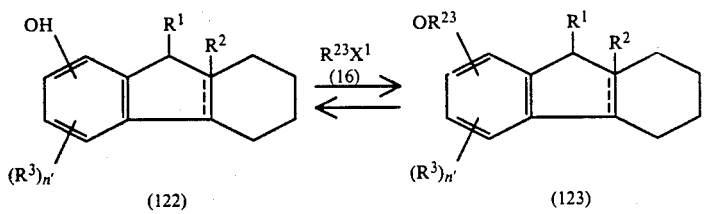

wherein $R^1$, $R^2$, $R^3$, $R^{23}$, $X^1$ and $n'$ are the same as wherein R , R defined above.

Reaction of the compound of the general formula (122) with the compound of the general formula (16) can be carried out under the same condition as in the reaction of the compound of the general formula (209) with the compound of the general formula (16) shown in the foregoing Reaction process formula-15. Also, the reaction to convert the compound of the general formula (123) to the compound of the general formula (122) can similarly be carried out under the same condition as in the reaction to convert the compound of the general formula (210) to the compound of the general formula (209).

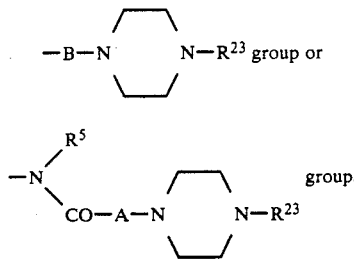

These compounds, however, can easily be separated.

Reaction process formula-23

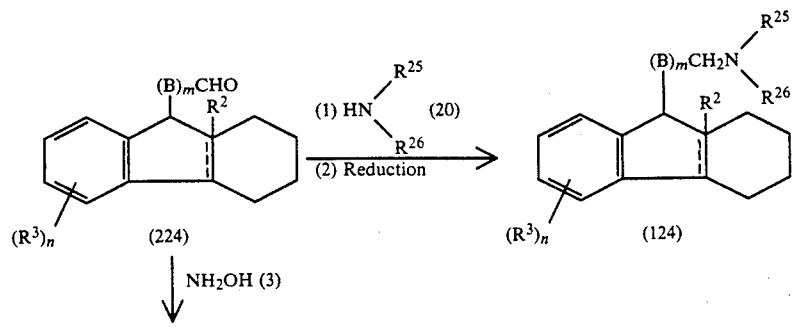

Reaction process formula-23 -continued

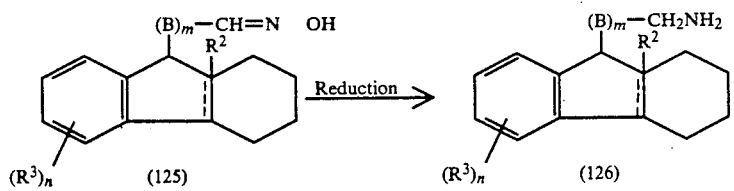

[wherein $R^2$, $R^3$, $R^{25}$, $R^{26}$, B, and n are the same defined above; m is an integer of 0 or 1; and the carbon-carbon bond between 4a- and 9a-positions in the hydrofluorene skeleton is a single or double bond; provides that when m is 1, then the number of carbon atoms in a group of the formula —$(B)_m$—$CH_2$— should not be over 6].

The reaction of a compound (224) with a compound (20) is carried out under conditions similar to those employed in the above-mentioned reaction of a compound (2') with a compound (9), except that the reaction temperature may be generally at 0 to 100° C., preferably at 0 to 80° C. In carrying out this reaction, a basic compound being used in the reaction of a compound (2) with hydroxylamine (3) can also be added. The reduction followed by the above-mentioned reaction can be carried out under conditions similar to those employed in the reduction of a compound (109). As to the amount of the hydrogenating reducing agent, generally 0.1 to 15 times the molar quantity, preferably 0.2 to 10 times the molar quantity of a compound (224) may be used.

The reaction of a compound (224) with hydroxylamine (3) can be carried out under conditions similar to those employed in the above-mentioned reaction of a compound (2) with hydroxylamine (3).

The reduction of a compound (125) can be carried out under conditions similar to those employed in the above-mentioned reduction of a compound (101).

Reaction process formula-24

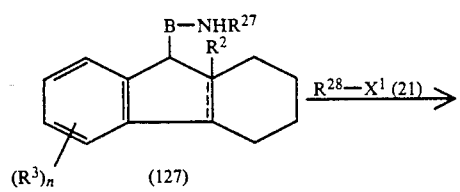

-continued
Reaction process formula-24

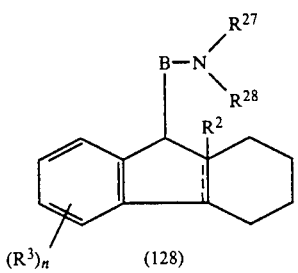

[wherein $R^2$, $R^3$, $X^1$, B, and n are the same as defined above; $R^{27}$ is a hydrogen atom, an unsubstituted lower alkyl group, a substituted lower alkyl group having a lower alkanoylamino group, a carboxy group, a carbamoyl group or a hydroxy group as substituents, a pyridyl-lower alkyl group, an unsubstituted pyrrolidinyl-lower alkyl group, a substituted pyrrolidinyl-lower alkyl group having a lower alkyl group as substituents, or a furyl-lower alkyl group; $R^{28}$ is the same as defined in $R^{27}$ above, excluding a hydrogen atom; and the carbon-carbon bond between 4a- and 9a-positions in the hydrofluorene skeleton is a single or double bond].

The reaction of a compound (127) with a compound (21) can be carried out under conditions similar to those employed in the above-mentioned reaction of a compound (106) with a compound (8).

A compound (224) used as the starting material in the above-mentioned reaction process formula-23 can be prepared by methods of the below mentioned reaction process formulas-25, -26 and -27.

Reaction process formula-25

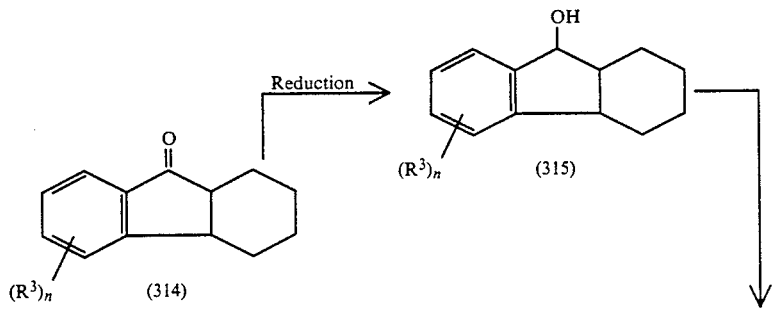

-continued

Reaction process formula-25

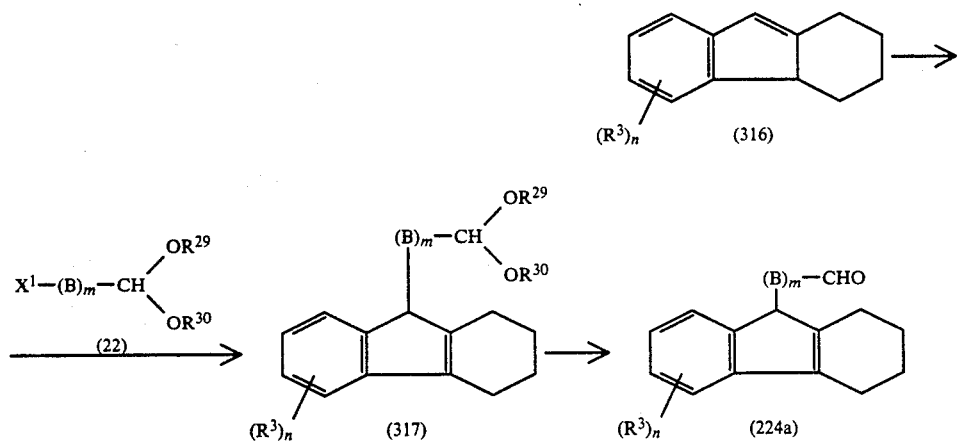

[wherein $R^3$, B, n, m and $X^1$ are the same as defined above; $R^{29}$ and $R^{30}$ are each a lower alkyl group].

The reduction of a compound (314) can be carried out under conditions similar to those employed in the method by using a hydrogenating reducing agent among the method of the above-mentioned reduction of a compound (109).

The reaction for converting a compound (315) to a compound (316) can be carried out in a suitable solvent in the presence of a catalyst for example a hydrohalic acid such as hydrochloric acid, hydrobromic acid or the like, phosphorus pentachloride, phosphorus pentabromide, phosphorus oxychloride, thionyl chloride, a halogenated sulfonic acid such as p-toluenesulfonyl chloride or the like.

As to the solvent used in this reaction, water, an ether such as dioxane, tetrahydrofuran, diethyl ether or the like, a halogenated hydrocarbon such as chloroform, methylene chloride, carbon tetrachloride or the like, or a mixed solvent of these solvent can be exemplified.

In the case of using a halogenated sulfonic acid as the catalyst, the reaction may be carried out in the presence of an inorganic basic compound such as sodium carbonate, potassium carbonate, sodium hydrogen carbonate, potassium hydrogen carbonate, sodium hydroxide, potassium hydroxide, a lithium salt, such as lithium chloride, lithium carbonate or the like; or an organic basic compound such as DBU, pyridine or triethylamine or the like.

The amount of the catalyst may be used at least an equimolar quantity, preferably an equimolar to 2 times the molar quantity to a compound (315). The reaction is carried out generally at 0° to 150° C., preferably at 0° to 80° C. for about 10 minutes to 6 hours.

The reaction of a compound (316) with a compound (22) can be carried out in a suitable solvent in the presence of a basic compound. As to the solvent used in this reaction, an aromatic hydrocarbon such as benzene, toluene, xylene or the like, an ether such as diethyl ether, tetrahydrofuran, dioxane, ethylene glycol dimethyl ether, diethylene glycol dimethyl ether or the like, an aliphatic hydrocarbon such as n-hexane, n-heptane, cyclohexane or the like, or a mixed solvent of these solvent can be exemplified. As to the basic compound used in this reaction, lithium compound such as n-butyl lithium, an alkali metal such as sodium metal or potassium metal, or an alkalimetal hydride such as sodium hydride or the like can be exemplified.

The amount of the basic compound and a compound (22) to a compound (316), at least an equimolar quantity, preferably an equimolar to 3 times the molar quantity each of the basic compound and a compound (22) may be used to a compound (316). The reaction is generally carried out at $-90°$ C. to room temperature, preferably at about $-70°$ C. to room temperature, and the reaction is completed about in 1 to 5 hours.

The reaction for converting a compound (317) to a compound (224a) can be carried out in the presence of an acid for example a hydrohalic acid such as hydrochloric acid, hydrobromic acid or the like, a mineral acid such as sulfuric acid, phosphoric acid or the like, a sulfonic acid such as p-toluenesulfonic acid or the like, in a suitable solvent, for example water, a mixed solvent of water with a lower alcohol such as methanol, ethanol, propanol or the like or a mixed solvent of water with an ether such as diethyl ether, tetrahydrofuran, dioxane or the like, at about room temperature to 150° C., preferably at about room temperature to 100° C., and the reaction is completed in about 1 to 24 hours.

Reaction process formula-26

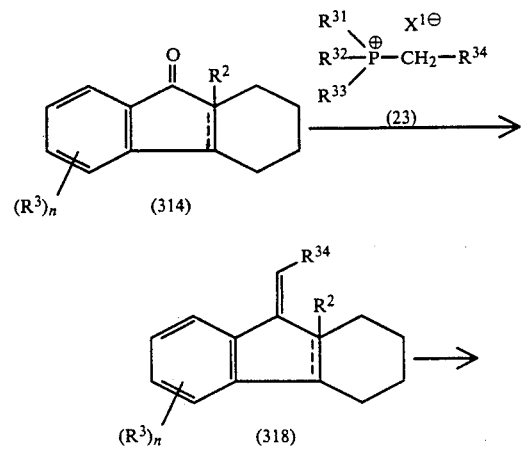

-continued
Reaction process formula-26

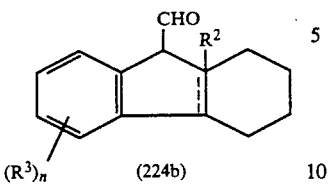

[wherein $R^2$, $R^3$, n and $X^1$ are the same as defined above; $R^{31}$, $R^{32}$ and $R^{33}$ are each a phenyl group or a lower alkyl group; and $R^{34}$ is a lower alkoxy group].

The reaction of a compound (314) with a compound (23) is so-called "Wittig Reaction" and is carried out in the presence of a basic compound in a suitable solvent.

As to the basic compound used in this reaction, an inorganic basic substance such as sodium metal, potassium metal, sodium hydride, sodium amide, sodium hydroxide, potassium hydroxide, sodium carbonate, potassium carbonate, sodium hydrogen carbonate or the like; metal alcoholate such as potassium t-butoxide, sodium methylate, sodium ethylate or the like, lithium salt such as methyl lithium, n-butyl lithium, phenyl lithium or the like, and an organic basic compound such as pyridine, piperidine, quinoline, triethylamine, N,N-dimethylaniline or the like can be exemplified.

As to the solvent used in this reaction, any inert solvent which does not give any adverse effect to the reaction can be used, for example an ether such as diethyl ether, dioxane, tetrahydrofuran, monoglyme (ethylene glycol dimethyl ether), diglyme (diethylene glycol dimethyl ether) or the like, an ormatic hydrocarbon such as benzene, toluene, xylene or the like, an aliphatic hydrocarbon such as n-hexane, pentane, heptane, cyclohexane or the like, an amine such as pyridine, N,N-dimethylaniline or the like, an aprotic polar solvent such as DMF (dimethylformamide), DMSO (dimethyl sulfoxide), HMPA (hexamethylphosphoric triamide) or the like can be exemplified.

The reaction can be carried out at a temperature of generally at −30 to 150° C., preferably at about −20° to 120° C., and the reaction is generally completed in about 5 to 15 hours.

The amount of a compound (23) to a compound (314) is generally at least an equimolar quantity, preferably an equimolar to 5 times the molar quantity of the former may be used to the latter.

The reaction for converting a compound (318) to a compound (224b) can be carried out under conditions similar to those employed in the reaction for converting a compound (317) to a compound (224).

Reaction process formula-27

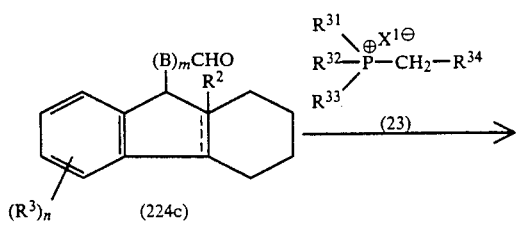

-continued
Reaction process formula-27

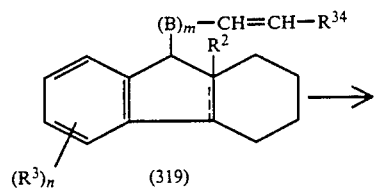

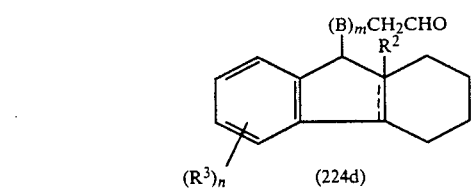

[wherein $R^2$, $R^3$, n, B, m, $R^{31}$, $R^{32}$, $R^{33}$, $R^{34}$ and $X^1$ are the same as defined above; provided that when m is 1, then the number of the carbon atoms in a group of the formula —(B)$_m$—CH2— should not over 6].

The reaction of a compound (224c) with a compound (23) can be carried out under conditions similar to those employed in the reaction of a compound (314) with a compound (23). The reaction for converting a compound (319) to a compound (224d) can be carried out under conditions similar to those employed in the reaction for converting a compound (318) to a compound (224b). The desired compound (224) used as the starting material used in the above-mentioned reaction process formula-23 can be obtained by conducting the reaction process formulas-25, 26 and 27 repeatedly.

Reaction process formula-28

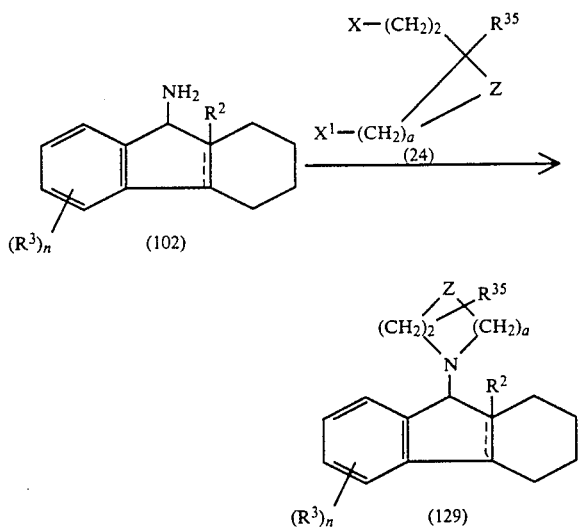

[wherein $R^2$, $R^3$, n, X, $X^1$ and the carbon-carbon bond between 4a- and 9a-positions in the hydrofluorene skeleton are the same as defined above; a is 1 or 2; Z is a methine group, a nitrogen atom or oxygen atom; and $R^{35}$ is a hydrogen atom or an oxy group].

The reaction of a compound of (102) with a compound (24) can be carried out under conditions similar to those employed in the reaction of a compound (102) with a compound (4) in the above-mentioned reaction process formula-2.

When $R^{34}$ in a compound (129) is an oxy group, such compound can be reduced under conditions similar to those employed in the reduction of a compound (109) in the above-mentioned reaction process formula-6 to obtain a compound (129) in which $R^{34}$ is a hydrogen atom.

The objective products thus obtained in each of these reaction processes can be separated and purified by usual separation means, for example solvent extraction, dilution, recrystallization, column chromatography, preparative thin-layer chromatography and the like.

Hydrofluoren derivatives represented by the general formula (1) according to the present invention including inevitably their stereo isomers and optical isomers.

Hydrofluorene derivatives represented by the general formula (1) according to the present invention can easily be converted into their acid-addition salts by reacting with pharmaceutically acceptable acids, and the present invention also including said acid-addition salts. As to the pharmaceutically acceptable acids, examples are inorganic acids such as hydrochloric acid, sulfuric acid, phosphoric acid, and hydrobromic acid, etc.; organic acids such as acetic acid, oxalic acid, succinic acid, maleic acid, fumaric acid, malic acid, tartaric acid, citric acid, malonic acid, methanesulfonic acid, benzoic acid, etc. are included.

Hydrofluoren derivatives according to the present invention can be used in any form of usual preparations of pharmaceutical compositions together with usual pharmaceutically acceptable carriers. Examples of pharmaceutically acceptable carriers which are selected depend on the desired form of pharmaceutical compositions, including diluents and excipients such as fillers, diluents, binders, wetting agents, disintegrating agents, surface active agents, lublicants, etc. No particular restriction is made to the administration unit forms and the pharmaceutical compositions can be selected from any desired unit form including tablets, pills, powders, liquors, suspensions, emulsions, granules, capsules, suppositories, injection preparations (including solutions, suspensions, etc.) ointments, etc.

For the purpose of to make in the form of tablets, carriers which are widely used in this field can be used, for example, excipients such as lactose, sucrose, sodium chloride, glucose, urea, starch, calcium carbonate, kaolin, crystalline cellulose, silicic acid, etc.; binding agents such as water, ethanol, propanol, simple sirup, glucose solution, starch solution, gelatin solution, carboxymethyl cellulose, shelac, methyl cellulose, potassium phosphate, polyvinylpyrrolidone, etc.; disintegrating agents such as dried starch, sodium alginate, agar-agar powder, laminalia powder, sodium hydrogen carbonate, calcium carbonate, esters of polyoxyethylene sorbitan fatty acids, sodium laurylsulfate, monoglyceride of stearic acid, starch lactose, etc.; disintegration inhibitors such as sucrose, stearin, coconut butter, hydrogenated vegetable oils, etc.; absorption accelarators such as quaternary ammonium bases, sodium laurylsulfonate, etc.; wetting agents such as glycerin, starch, etc.; adsorbing agents such as starch, lactose, kaolin, bentonite, colloidal silicic acid, etc.; and lubricants such as purified talc, stearic acid salts, boric acid powder, polyethylene glycols, etc. If necessary, the tablets can be further coated with usual coating materials to make them into coated tablets, for example tablets coated with sugar, tablets coated with gelatin film, tablets coated with enteric coating layers, tablets coated with films or double layer tablets as well as multiple layer tablets, etc.

For the purpose of to make in the form of pills, any carrier which is known and used widely in this field can be used, for example, excipients such as glucose, lactose, starch, coconut butter, hydrogenated vegetable oils, kaolin, talc, etc.; binders such as powdered gum arabic, powdered tragacanth gum, gelatin, ethanol, etc.; disintegrating agents such as laminaria, agar-agar, etc.

For the purpose of to make in the form of suppositories, carriers which are known and widely used in this field can also be used, for example, polyethylene glycols, coconut butter, higher alcohols, esters of higher alcohols, gelatin, semi-synthesized glycerides, etc.

For the purpose of to make in the form of injection preparations, solutions and supensions prepared are further sterilized and are preferably isotonic to the blood. In preparing injection preparations in the form of solutions, emulsions and suspensions, any carrier which is known and is widely used in this field can also be used, for example water, ethyl alcohol, propylene glycol, ethoxylated isostearyl alcohol, polyoxyated isostearyl alcoho, polyoxyethylene sorbitan fatty acid esters, etc. In these instances, adequate amounts of sodium chloride, glucose or glycerin may be added to make the desired injection preparations isotonic. Furthermore, usual dissolving agents, buffer solutions, analgesic agents may be added. Also coloring materials, preservatives, perfumes, seasoning agents, sweetening agents and other medicines may be added in the desired pharmaceutical preparations, if necessary.

For the purpose of to make the preparation in the form of pastes, creams and gels, diluents which are known and widely used in these fields can be also used, for example white petrolatum, paraffin, glycerin, cellulose derivatives, polyethylene glycols, silicones, bentonite, etc.

The amount of compound represented by the general formula (1) or salt thereof to be contained in the pharmaceutical composition according to the present invention is not specifically restricted, and can suitably be selected from a wide range, and generally 1 to 70% by weight of the compound or salt thereof may be contained in the pharmaceutical composition.

Methods for administering the above-mentioned pharmaceutical composition are not specifically restricted, thus, the compositions can be administered in various forms of pharmaceutical preparations depend on the age, the distinction of sex, the degree of symptoms and other conditions of the patient without any restriction. For example, tablets, pills, solutions, suspensions, emulsions, granules and capsules are administered orally; injection preparations are administered intravenously singly, or administered with usual injectable transfusions such as glucose solutions, amino acids solutions, etc.; if necessary, the injection preparations are administered singly intramuscularly, intracutaneously, subcutaneously or intraperitoneally; and the suppositories are administered into rectum.

The dosage of the above-mentioned pharmaceutical compositions can be selected suitably according to the methods for administrations, the age of the patient, the distinction of sex and other conditions as well as the degree of the symptoms, and generally 0.2 to 200 mg/kg/day of compound represented by the general formula (1) or salt thereof may be used.

REFERENCE EXAMPLE 1

A mixture of 194 g of 2,4-xylenol and 233 g of cyclohexylcarbonyl chloride was stirred at 110° C. for 1 hour and then thereto was gradually added 318 g of anhydrous aluminum chloride, followed by stirring for further 1 hour at 110° C. The reaction mixture was added to 2 liters of ice water and the organic layer was extracted with 2 liters of chloroform. The extract was washed successively with water and then with a saturated aqueous sodium chloride solution and thereafter dried with anhydrous magnesium sulfate. The chloroform was distilled off under reduced pressure and the resulting residue was purified by a silica gel column chromatography (eluent: n-hexane) to obtain 256.2 g of cyclohexyl 3,5-dimethyl-2-hydroxyphenyl ketone. Brown oily substance.

$^1$H-NMR (CDCl$_3$) δ: 0.88 (1H, m), 1.28–1.89 (9H, m), 2.22 (3H, s), 2.29 (3H, s), 3.29 (1H, m), 7.16 (1H, s), 7.39 (1H, s), 12.74 (1H, s).

The following compounds were prepared in the same manner as in Reference Example 1 using suitable starting materials.

Cyclohexyl 3-bromo-2-hydroxy-5-methylphenyl ketone

Melting point: 124°–125° C.

Light yellow needle-like crystal (recrystallized from n-hexane)

Cyclohexyl 2-hydroxy-3-methyl-5-chlorophenyl ketone

Dark yellow oily substance $^1$H-NMR (CDCl$_3$) δ: 0.68–1.94 (10H, m), 2.24 (3H, s), 3.14–3.29 (1H, m), 7.29 (1H, d, J=2.5Hz), 7.57 (1H, d, J=2.5Hz), 12.81 (1H, s).

REFERENCE EXAMPLE 2

53 Grams of 60% sodium hydride was gradually added to a solution prepared by dissolving 256.2 g of cyclohexyl 3,5-dimethyl-2-hydroxyphenyl ketone in 1 liter of dimethylformamide with stirring, generating the temperature of the reaction mixture was risen to 70° C. by generating the heat. After continuation of stirring for 30 minutes, the reaction mixture was cooled to room temperature and thereto was added dropwise 233 g of methyl iodide. The reaction mixture was further stirred at the same temperature for 2 hours and then added to 1 liter of ice water and stirred. The organic layer was extracted with 3 liters of ethyl acetate. The extract was washed with water and then with a saturated aqueous sodium chloride solution and then dried with anhydrous magnesium sulfate. The solvent was distilled off under reduced pressure to obtain 285.2 g of cyclohexyl 3,5-dimethyl-2-methoxyphenyl ketone.

Brown oily substance.

$^1$H-NMR (CDCl$_3$) δ: 1.10–2.10 (10H, m), 2.27 (6H, s), 3.36 (1H, m), 3.66 (3H, s), 6.97 (1H, s), 7.07 (1H, s).

Cyclohexyl 2-hydroxy-3-methyl-5-chlorophenyl ketone

Dark yellow oily substance $^1$H-NMR (CDCl$_3$) δ: 0.68–1.94 (10H, m), 2.24 (3H, s), 3.14–3.29 (1H, m), 7.29 (1H, d, J=2.5 Hz), 7.57 (1H, d, J=2.5 Hz), 12.81 (1H, s).

REFERENCE EXAMPLE 2

53 Grams of 60% sodium hydride was gradually added to a solution prepared by dissolving 256.2 g of cyclohexyl 3,5-dimethyl-2-hydroxyphenyl ketone in 1 liter of dimethylformamide with stirring, generating heat at 70° C. After continuation of stirring for 30 minutes, the reaction mixture was cooled to room temperature and thereto was added dropwise 233 g of methyl iodide. The reaction mixture was further stirred at the same temperature for 2 hours and then added to 1 liter of ice water and stirred. The organic layer was extracted with 3 liters of ethyl acetate. The extract was washed with water and then with a saturated aqueous sodium chloride solution and then dried with anhydrous magnesium sulfate. The solvent was distilled off under reduced pressure to obtain 285.2 g of cyclohexyl 3,5-dimethyl-2-methoxyphenyl ketone.

Brown oily substance.

$^1$H-NMR (CDCl$_3$) δ: 1.10–2.10 (10H, m), 2.27 (6H, s), 3.36 (1H, m), 3.66 (3H, s), 6.97 (1H, s), 7.07 (1H, s).

The following compounds were prepared in the same manner as in Reference Example 2 using suitable starting materials.

Cyclohexyl 3-bromo-2-methoxy-5-methylphenyl ketone.

Light yellow oily substance.

$^1$H-NMR (CDCl$_3$) δ: 1.17–1.53 (6H, m), 1.63–1.97 (4H, m), 2.31 (3H, s), 3.02 - 3.17 (1H, m), 3.80 (3H, s), 7.08 (1H, s), 7.45 (1H, s).

Cyclohexyl 2-methoxy-3-methyl-5-chlorophenyl ketone.

Dark yellow oily substance.

$^1$H-NMR (CDCl$_3$) δ: 1.18–1.97 (10H, m), 2.29 (3H, s), 3.01–3.16 (1H, m), 3.70 (3H, s), 7.15 (1H, d, J=2.5 Hz), 7.24 (1H, d, J=2.5 Hz).

REFERENCE EXAMPLE 3

230.0 Grams of freshly ground anhydrous aluminum chloride was suspended in 1 liter of dichloromethane. Into this suspension was added 175.0 g of p-anisole with cooling so as not to exceed 0° C. To this mixture kept at −5° C. to 0° C. was added dropwise 230.0 g of cyclohexylcarbonyl chloride over a period of about one hour. After completion of the addition, the reaction mixture was stirred at −5° C. to 0° C. for 2 hours and then was poured into 30 liters of ice water. Extraction was effected with 1.5 liters of dichloromethane and the organic layer was dried with anhydrous magnesium sulfate. Dichloromethane was concentrated to obtain 330 g of cyclohexyl 2-methoxy-5-methylphenyl ketone.

Light yellow oily substance.

$^1$H-NMR (CDCl$_3$) δ: 1.10–2.10 (10H, m), 2.27 (3H, s), 2.97–2.37 (1H, m), 3.83 (3H, m), 6.80 (1H, d, J=9 Hz), 7.18 (1H, dd, J=3 Hz, 9 Hz), 7.27 (1H, d, J=3 Hz).

REFERENCE EXAMPLE 4

285.2 Grams of cyclohexyl 3,5-dimethyl-2methoxyphenyl ketone was dissolved in 800 ml of acetic acid. To the solution was added 8 ml of 47% hydrobromic acid and then a solution prepared by dissolving 212 g of bromine in 100 ml of acetic acid was added thereto dropwise with ice-cooling and stirring. After stirring at room temperature for 2 hours, the reaction mixture was poured into ice water, followed by extraction with 2 liters of ethyl acetate. The extract was washed with water and then with a saturated aqueous sodium chloride solution and then dried with anhydrous magnesium sulfate and the solvent was distilled off under reduced pressure to obtain 363.6 g of 1-bromocyclohexyl 3,5-dimethyl-2-methoxyphenyl ketone.

Brown oily substance.

$^1$H-NMR (CDCl$_3$) δ: 1.20–2.33 (10H, m), 2.27 (3H, s), 2.30 (3H, s), 3.66 (3H, s), 7.03 (2H, s).

The following compounds were prepared in the same manner as in Reference Example 4 using suitable starting materials.

1-Bromocyclohexyl 2-methoxy-5-methylphenyl ketone.

Melting point: 65°-66° C.

Colorless flake-like crystal (recrystallized from ethyl acetate)

1-Bromocyclohexyl 2-methoxy-3-bromo-5-methylphenyl ketone.

Yellow oily substance.

$^1$H-NMR (CDCl$_3$) δ: 1.22-1.39 (1H, m), 1.57-2.00 (7H, m), 2.09-2.23 (2H, m), 2.33 (3H, s), 3.79 (3H, s), 7.42 (2H, s).

1-Bromocyclohexyl 2-methoxy-3-methyl-5-chlorophenyl ketone.

Melting point: 69°-70° C.

Colorless prism-like crystal (recrystallized from n-hexane).

REFERENCE EXAMPLE 5

363.5 Grams of 1-bromocyclohexyl 3,5-dimethyl-2-methoxyphenyl ketone was dissolved in 1 liter of dimethylformamide. To the solution was added 140 g of lithium chloride, followed by stirring at 90° C. for 1 hour. The reaction mixture was poured into 1 liter of ice water with stirring and the organic layer was extracted with 3 liters of methylene chloride. The extract was washed with water and saturated aqueous sodium chloride solution in this order and then dried with anhydrous magnesium sulfate and methylene chloride was distilled off under reduced pressure. The residue was purified by a silica gel column chromatography (eluent: ethyl acetate:n-hexane=96:4) to obtain 197.0 g of 1-cyclohexenyl 3,5-dimethyl-2-methoxyphenyl ketone.

Brown oily substance.

$^1$H-NMR (CDCl$_3$) δ: 1.56-2.50 (8H, m), 2.23 (6H, s), 3.63 (3H, s), 6.47 (1H, s), 6.77 (1H, s), 6.97 (1H, s).

The following compounds were prepared in the same manner as in Reference Example 5 using suitable starting materials.

1-Cyclohexenyl 2-methoxy-5-methylphenyl ketone.

Light yellow oily substance.

$^1$H-NMR (CDCl$_3$) δ: 1.50-1.85 (4H, m), 2.07-2.58 (4H, m), 2.27 (3H, s), 3.72 (3H, s), 6.42-6.61 (1H, m), 6.78 (1H, d, J=9 Hz), 6.92 (1H, d, J=3 Hz), 7.12 (1H, dd, J=3 Hz, 9 Hz).

1-Cyclohexenyl 2-methoxy-3-bromo-5-methylphenyl ketone.

Light yellow oily substance.

$^1$H-NMR (CDCl$_3$) δ: 1.58-1.80 (4H, m), 2.18-2.28 (2H, m), 2.23 (3H, s), 2.35-2.47 (2H, m), 3.76 (3H, s), 6.52-6.58 (1H, m), 6.92 (1H, s), 7.42 (1H, s).

1-Cyclohexenyl 2-methoxy-3-methyl-5-chlorophenyl ketone.

Light yellow oily substance.

$^1$H-NMR (CDCl$_3$) δ: 1.60-1.80 (4H, m), 2.22-2.30 (2H, m), 2.24 (3H, s), 2.37-2.46 (2H, m), 3.68 (3H, s), 6.54-6.61 (1H, m), 6.99 (1H, d, J=2.5 Hz), 7.20 (1H, d, J=2.5 Hz).

REFERENCE EXAMPLE 6

197.0 Grams of 1-cyclohexenyl 3,5-dimethyl-2-methoxyphenyl ketone was gradually added to polyphosphoric acid prepared from 900 g of phosphorus pentoxide and 900 g of phosphoric acid at 100° C. with stirring and the mixture was stirred at 100° C. for 3 hours. The reaction mixture was poured into 3 liters of ice water and extraction was carried out with 3 liters of methylene chloride. The extract was washed with water and then saturated aqueous sodium chloride solution and then dried with anhydrous magnesium sulfate. Methylene chloride was distilled off under reduced pressure. The residue was purified by a silica gel column chromatography (eluent: ethyl acetate:n-hexane =99:1) and then recrystallized from n-hexane to obtain 46.0 g of 5,7-dimethyl-8-methoxy-1,2,3,4,4a,9a-hexahydro-9-fluorenone.

Melting point: 72°-74° C.

Colorless needle-like crystal.

The following compounds were prepared in the same manner as in Reference Example 6 using suitable starting materials.

5-Methyl-7-bromo-8-methoxy-1,2,3,4,4a,9a-hexahydro-9-fluorenone.

Melting point: 81°-82° C.

Colorless prism-like crystal (recrystallized from ethanol).

5-Methyl-8-methoxy-1,2,3,4,4a,9a-hexahydro-9-fluorenone.

Melting point: 126°-127° C.

Colorless needle-like crystal (recrystallized from ethanol).

5-Chloro-8-methoxy-7-methyl-1,2,3,4,4a,9a-hexahydro-9-fluorenone.

Melting point: 87.5°-88.5° C.

Colorless needle-like crystal (recrystallized from ethanol).

REFERENCE EXAMPLE 7

10 Grams of 5,7-dimethyl-8-methoxy-1,2,3,4,4a,9a-hexahydro-9-fluorenone was dissolved in 45 ml of acetonitrile and to the solution were gradually added 12.14 g of sodium iodide and 10.79 g of freshly ground aluminum chloride. After stirring at room temperature for 1.5 hour, the reaction mixture was poured into water and extracted with dichloromethane. The organic layer was dried with magnesium sulfate and then the solvent was distilled off. The residue was purified by a silica gel column chromatography (eluent: ethyl acetate:n-hexane=1:20) and thereafter recrystallized from ethanol to obtain 9.34 g of 5,7-dimethyl-8-hydroxy-1,2,3,4,4a,9a-hexahydro-9-fluorenone Melting point: 64°-65° C.

Colorless granular crystal.

The following compounds were prepared in the same manner as in Reference Example 7 using suitable starting materials.

8-Hydroxy-5-methyl-1,2,3,4,4a,9a-hexahydro-9-fluorenone.

Melting point: 55.5°-56° C.

Colorless needle-like crystal (recrystallized from petroleum ether).

5-Methyl-7-bromo-8-hydroxy-1,2,3,4,4a,9a-hexahydro-9-fluorenone.

Melting point: 58°-59° C.

Colorless prism-like crystal (recrystallized from n-hexane).

8-Hydroxy-5,7,9a-trimethyl-1,2,3,4,4a,9a-hexahydro-9-fluorenone.

Brown oily substance.

$^1$H-NMR (CDCl$_3$) δ: 1.04-1.77 (6H, m), 1.16 (3H, s), 1.87-2.40 (2H, m), 2.22 (3H, s), 2.26 (3H, s), 2.94 (1H, brt, J=7.5 Hz), 7.10 (1H, s), 9.03 (1H, s).

5-Chloro-8-hydroxy-7-methyl-1,2,3,4,4a,9a-hexahydro-9-fluorenone.

Melting point: 66°-68° C.

Colorless prism-like crystal (recrystallized from ethanol).

REFERENCE EXAMPLE 8

3.42 Grams of 60% sodium hydride was gradually added to a solution prepared by dissolving 17.7 g of 5,7-dimethyl-8-methoxy-1,2,3,4,4a,9a-hexahydro-9-fluorenone in 100 ml of dimethylformamide under ice-cooling, followed by stirring at room temperature for 30 minutes. Then, 5.4 ml of methyl iodide was added thereto under ice-cooling, followed by stirring at room temperature for 1 hour. The reaction mixture was poured into 3 liters of water and extracted with chloroform. The organic layer was dried with magnesium sulfate and then the solvent was distilled off. The residue was purified by a silica gel column chromatography (eluent: ethyl acetate:n-hexane=1:20) to obtain 9.6 g of 5,7,9a-trimethyl-8-methoxy-1,2,3,4,4a,9a-hexahydro-9fluorenone. fluorenone.

Brown oily substance.

$^1$H-NMR (CDCl$_3$) δ: 0.77–1.77 (6H, m), 1.08 (3H, s), 2.07–2.40 (2H, m), 2.24 (3H, s), 2.29 (3H, s), 2.77–3.02 (1H, m), 3.91 (3H, s), 7.15 (1H, s).

REFERENCE EXAMPLE 9

4.50 Grams of 8-hydroxy-5-methyl-1,2,3,4,4a,9a-hexahydro-9-fluorenone was dissolved in 50 ml of acetic acid and to the solution were gradually added dropwise 0.2 ml of hydrobromic acid and 1.3 ml of bromine, followed by refluxing under heating for 1 hour. The reaction mixture was poured into ice water and extracted with chloroform. The organic layer was washed with saturated aqueous sodium bicarbonate solution and saturated aqueous sodium chloride solution in this order and then dried with magnesium sulfate. The solvent was distilled off and the residue was purified by a silica gel column chromatography (eluent: ethyl acetate:n-hexane=1:10) and then recyrstallized from ethanol to obtain 3.86 g of 7,9a-dibromo-8-hydroxy-5-methyl-1,2,3,4,4a,9a-hexahydro-9-fluorenone.

Melting point: 102°–104° C.

Light yellow prism-like crystal.

REFERENCE EXAMPLE 10

20.0 Grams of 8-hydroxy-5-methyl-1,2,3,4,4a,9a-hexahydro-9-fluorenone, 10.4 g of potassium hydroxide and 200 ml of methanol were refluxed under heating until a homogeneous solution was produced. The solution was left to stand and thereto was added 16.0 ml of allyl bromide. The mixture was again refluxed under heating for 3 hours. The reaction mixture was poured into ice water and the separated crystal was collected by filtration and washed with water and then with n-hexane. The thus obtained crystal was once dissolved in chloroform and dried with magnesium sulfate and thereafter the solvent was distilled off. The crystal was recrystallized from ethanol to obtain 14.6 g of 8-allyloxy-5-methyl-1,2,3,4,4a,9a-hexahydro-9-fluorenone.

Melting point: 106°–107° C.

Colorless needle-like crystal.

REFERENCE EXAMPLES 11–12

The following compounds were prepared in the same manner as in Reference Example 10 using suitable starting materials. The results are shown in Table 1.

TABLE 1

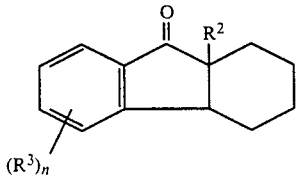

| Reference Example | R$^2$ | R$^3$ | n | Crystal form (Solvent for recrystallization) | Melting point (°C.) |
|---|---|---|---|---|---|
| 11 | H | 5-CH$_3$<br>8-OCH$_2$CH=CH—C$_6$H$_5$ | 2 | Light yellow needle-like crystal (Ethanol) | 151–152 |
| 12 | H | 5-CH$_3$<br>8-OCH$_2$CH=CHCH$_3$ | 2 | Light yellow needle-like crystal (Methanol) | 124–125 |

REFERENCE EXAMPLE 13

A solution prepared by dissolving 16.7 g of 8-allyloxy-5-methyl-1,2,3,4,4a,9a-hexahydro-9-fluorenone in 70 ml of tetralin was refluxed under heating for 10 hours. Tetralin was distilled off under reduced pressure and then the residue was purified by a silica gel column chromatography (eluent: ethyl acetate:n-hexane=1:10) to obtain 12.63 g of 7-allyl-8-hydroxy-5-methyl-1,2,3,4,4a,9a-hexahydro-9-fluorenone.

Light yellow oily substance.

$^1$H-NMR (CDCl$_3$) δ: 0.77–1.97 (6H, m), 2.07–2.45 (2H, m), 2.27 (3H, s), 2.60–2.90 (1H, m), 3.17–3.50 (3H, m), 4.87–5.20 (2H, m), 5.74–6.22 (1H, m), 7.10 (1H, s), 8.98 (1H, s).

REFERENCE EXAMPLES 14–15

The following compounds were prepared in the same manner as in Reference Example 13 using suitable starting materials. The results are shown in Table 2.

TABLE 2

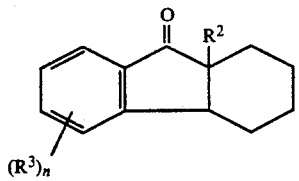

| Reference Example No. | $R^2$ | $R^3$ | n | Properties | $^1$H-NMR (CDCl$_3$) δ |
|---|---|---|---|---|---|
| 14 | H | 5-CH$_3$, 8-OH, 7-CH(CH=CH$_2$)(C$_6$H$_5$) | 3 | Yellowish brown oily substance | 0.87–1.77 (6H, m), 2.05–2.38 (2H, m), 2.23 (3H, s), 2.63–2.90 (1H, m), 3.17–3.53 (1H, m), 4.83–5.28 (3H, m) 6.07–6.50 (1H, m), 6.93–7.30 (6H, m), 9.03 (1H, brs) |
| 15 | H | 5-CH$_3$, 8-OH, 7-CH(CH$_3$)(CH=CH$_2$) | 3 | Yellow oily substance | 0.89–1.07 (1H, m), 1.13–1.90 (5H, m), 1.40 (d, J=7.0Hz) ⎫ total 3H; 1.42 (d, J=7.0Hz) ⎭; 2.42–2.47 (2H, m), 2.34 (3H, s), 2.87 (1H, dt, J=11Hz, 3Hz), 3.41 (1H, dt, J=11Hz, 6Hz), 3.94 (1H, dq, J=7Hz, 7Hz), 5.08–5.23 (2H, m), 6.02–6.20 (1H, m), 7.19 (1H, s), 9.14 (1H, s) |

REFERENCE EXAMPLE 16

A mixture of 25 g of 5-methyl-8-hydroxy-1,2,3,4,4a,9a-hexahydro-9-fluorenone, 62.5 ml of acetic anhydride and 18.88 ml of bisdimethylaminomethane was stirred with heating at 90° C. for 2 hours. The reaction mixture was left to stand for cooling and then to the reaction mixture was added saturated aqueous sodium chloride solution, followed by extraction with dichloromethane. The organic layer was dried with magnesium sulfate and then the solvent was distilled off. The residue was purified by a silica gel column chromatography (eluent: ethyl acetate:n-hexane=1:10) to obtain 14.37 g of 7-dimethylaminomethyl-8-hydroxy-5-methyl-1,2,3,4,4a,9a-hexahydro-9-fluorenone.

Yellow oily substance.

$^1$H-NMR (CDCl$_3$) δ: 0.78–0.97 (1H, m), 1.08–1.47 (2H, m), 1.60–1.80 (4H, m), 2.13 (3H, s), 2.28–2.53 (2H, m), 2.46 (3H, s), 2.47 (3H, s), 2.78–2.86 (1H, m), 3.43 (1H, dt, J=11 Hz, 6 Hz), 5.15 (2H, s), 7.50 (1H, s).

REFERENCE EXAMPLE 17

To 20 g of 8-hydroxy-5-methyl-1,2,3,4,4a,9a-hexahydro-9-fluorenone were added 200 ml of water and 200 ml of concentrated sulfuric acid and the mixture was stirred with heating at 90° C. At the same temperature, thereto was gradually added 53.71 g of N-tert-butylurea, followed by stirring with heating for 14 hours. Then, 10 g of N-tert-butylurea was further added, followed by further stirring at 90° C. for 5 hours. The reaction mixture was poured into 2 liters of water and extracted with chloroform. The chloroform layer was washed with saturated aqueous sodium chloride solution and then dried with magnesium sulfate. The solvent was distilled off and the residue was purified by a silica gel column chromatography (eluent: ethyl acetate:n-hexane=1:10) and thereafter recrystallized from n-hexane to obtain 19.67 g of 7-tert-butyl-8-hydroxy-5-methyl-1,2,3,4,4a,9a-hexahydro-9-fluorenone.

Melting point: 77°–78° C.
Colorless granular crystal.

REFERENCE EXAMPLE 18

6.0 Grams of sodium borohydride was added to a solution prepared by dissolving 15.0 g of 5,7-dimethyl-8-methoxy-1,2,3,4,4a,9a-hexahydro-9-fluorenone in 300 ml of methanol and 50 ml of water and reaction was effected under ice-cooling for 4 hours. The solvent was distilled off and the residue was extracted with dichloromethane and then the extract was washed twice with saturated sodium chloride solution. Then, this was dried with magnesium sulfate and the solvent was distilled off to obtain 16.1 g of 5,7-dimethyl-8-methoxy-9-hydroxy-1,2,3,4,4a,9a-hexahydrofluorene.

REFERENCE EXAMPLE 19

5.5 Milliliters of thionyl chloride was added dropwise to a chloroform solution containing 16.1 g of 5,7-dimethyl-8-methoxy-9-hydroxy-1,2,3,4,4a,9a-hexahydrofluorene under ice-cooling. After completion of the addition, reaction was effected at the same temperature for 2 hours. The reaction mixture was washed successively with water twice, saturated aqueous sodium chloride solution and saturated sodium bicarbonate solution and dried with magnesium sulfate. Then, the solvent was distilled off and the residue was purified by a silica gel column chromatography (eluent: ethyl acetate:n-hexane=1:20) to obtain 13.26 g of 5,7-dimethyl-8-methoxy-2,3,4,4a-tetrahydro-1H-fluorene.

Colorless oily substance.

$^1$H-NMR (CDCl$_3$) δ: 0.95 (1H, ddd, J=3.5 Hz, 12.5 Hz, 25.0 Hz), 1.36 (1H, m), 1.55–1.74 (2H, m), 2.37 (3H, s), 2.42 (3H, s), 2.37–2.52 (1H, m), 2.83 (2H, m), 3.13 (1H, dd, J=5.5 Hz, 12.0 Hz), 3.96 (3H, s), 6.60 (1H, s), 6.81 (1H, s).

REFERENCE EXAMPLE 20

19 Milliliters of a 15% n-butyl lithium n-hexane solution was added dropwise to a tetrahydrofuran solution containing 5.0 g of 5,7-dimethyl-8-methoxy-2,3,4,4a-tetrahydro-1H-fluorene in 50 ml of tetrahydrofuran at −50° C. After stirring at the same temperature for 40 minutes, thereto was added dropwise 6 ml of bromoacetoaldehyde diethyl acetal at the same temperature, followed by stirring at the same temperature for 1.5 hour. To the reaction mixture was added a saturated aqueous ammonium chloride solution and this was diluted with diethyl ether, washed with water twice and then with a saturated aqueous sodium chloride solution and then dried with magnesium sulfate. The solvent was distilled off and the residue was purified by a silica gel column chromatography (eluent: ethyl acetate:n-hexane=1:30) to obtain 5.68 g of 5,7-dimethyl-8-methoxy-9-(2,2-diethoxyethyl)-1,2,3,4-tetrahydro-9H-fluorene.

Light yellow oily substance.

$^1$H-NMR (CDCl$_3$) δ: 0.90 (3H, t, J=7.0 Hz), 1.02 (3H, t, J=7.0 Hz), 1.59-1.80 (4H, m), 2.24 (3H, s), 2.16-2.60 (4H, m), 2.43 (3H, s), 2.65 (2H, m), 3.23-3.62 (5H, m), 3.78 (3H, s), 4.25 (1H, t, J=4.0 Hz), 6.78 (1H, s).

REFERENCE EXAMPLE 21

A tetrahydrofuran solution containing 1.45 g of 5,7-dimethyl-8-methoxy-9-(2,2-diethoxyethyl)-1,2,3,4-tetrahydro-9H-fluorene in 10 ml of tetrahydrofuran and 10 ml of 15% hydrochloric acid were stirred at room temperature for 3 hours. The reaction mixture was extracted with dichloromethane and the extract was washed with saturated aqueous sodium chloride solution and saturated sodium bicarbonate solution and then dried with magnesium sulfate. The solvent was distilled off to obtain 1.20 g of 5,7-dimethyl-8-methoxy-9-formylmethyl-1,2,3,4-tetrahydro-9H-fluorene.

Light yellow oily substance.

$^1$H-NMR (CDCl$_3$) δ: 1.6-2.0 (4H, m), 2.33 (3H, s), 2.3-2.4 (2H, m), 2.74 (2H, m), 2.95 (2H, m), 3.83 (3H, s), 3.8 (1H, m), 6.91 (1H, s), 9.54 (1H, m).

REFERENCE EXAMPLE 22

The following compounds were prepared in the same manner as in Reference Example 3 using suitable starting materials.

Cyclohexyl 2,5-dimethoxyphenyl ketone.

Yellowish brown oily substance.

$^1$H-NMR (CDCl$_3$) δ: 1.13-2.03 (9H, m), 3.21 (1H, m), 3.46 (3H, s), 3.82 (3H, s), 6.77-7.03 (2H, m), 7.07 (1H, d, J=2.5 Hz)

Cyclohexyl 5-fluoro-2-methoxyphenyl ketone.

Light yellow oily substance.

$^1$H-NMR (CDCl$_3$) δ: 1.13-1.77 (10H, m), 3.18 (1H, m), 3 86 (3H, s), 6.89 (1H, dd, J=4 Hz, 10 Hz), 7.10 (1H, ddd, J=4 Hz, 10 Hz, 11Hz), 7.22 (1H, dd, J=4 Hz, 11 Hz).

REFERENCE EXAMPLE 23

The following compounds were prepared in the same manner as in Reference Example 4 using suitable starting materials.

1-Bromocyclohexyl 2,5-dimethoxyphenyl ketone.

Yellowish brown oily substance.

$^1$H-NMR (CDCl$_3$) δ: 1.18-1.43 (2H, m), 1.60-2.07 (6H, m), 2.15-2.30 (2H, m), 3.76 (3H, s), 3.78 (3H, s), 6.88 (2H, ABq, d, J=10 Hz, 12.5 Hz, 2.5 Hz), 7.19 (1H, d, J=2.5 Hz).

1-Bromocyclohexyl 5-fluoro-2-methoxyphenyl ketone.

Light yellow oily substance.

$^1$H-NMR (CDCl$_3$) δ: 1.22 (1H, m), 1.57-2.03 (7H, m), 2.13-2.27 (2H, m), 3.78 (3H, s), 6.86 (1H, dd, J=3 Hz, 9 Hz), 7.06 (1H, ddd, J=3 Hz, 8 Hz, 9 Hz), 7.36 (1H, dd, J=3 Hz, 8 Hz).

REFERENCE EXAMPLE 24

The following compounds were prepared in the same manner as in Reference Example 5 using suitable starting materials.

1-Cyclohexenyl 2,5-dimethoxyphenyl ketone.

Reddish yellow oily substance.

$^1$H-NMR (CDCl$_3$) δ: 1.60-1.83 (4H, m), 2.18-2.30 (2H, m), 2.37-2.48 (2H, m), 3.74 (3H, s), 3.77 (3H, s), 6.53-6.63 (1H, m), 6.72 (1H, d, J=2.5 Hz), 6.83-6.97 (2H, m).

1-Cyclohexenyl 5-fluoro-2-methoxyphenyl ketone.

Light yellow oily substance.

$^1$H-NMR (CDCl$_3$) δ: 0.83-0.93 and 1.23-1.33 (1H, m), 1.58-1.80 (3H, m), 2.18-2.30 (2H, m), 2.35-2.47 (2H, m), 3.76 (3H, s), 6.57 (1H, m), 6.83-6.95 (2H, m), 7.04 (1H, ddd, J=3 Hz, 8 Hz, 9 Hz).

REFERENCE EXAMPLE 25

The following compounds were prepared in the same manner as in Reference Example 6 using suitable starting materials.

5,8-Dimethoxy-1,2,3,4,4a,9a-hexahydro-9-fluorenone.

Melting point: 139°-141° C.

Colorless prism-like crystal (recrystallized from ethanol).

5-Fluoro-8-methoxy-1,2,3,4,4a,9a-hexahydro-9-fluorenone.

Melting point: 131°-132° C.

Colorless needle-like crystal (recrystallized from ethanol).

REFERENCE EXAMPLE 26

The following compounds were prepared in the same manner as in Reference Example 7 using suitable starting materials.

8-Hydroxy-5-methoxy-1,2,3,4,4a,9a-hexahydro-9-fluorenone.

Yellow oily substance.

$^1$H-NMR (CDCl$_3$) δ: 0.97-1.48 (3H, m), 1.53-1.85 (3H, m), 2.20-2.40 (2H, m), 2.77 (1H, dt, J=4 Hz, 6 Hz), 3.47 (1H, dt, J=6 Hz, 10 Hz), 3.83 (3H, s), 6.72 (1H, d, J=8.5 Hz), 6.99 (1H, d, J=8.5 Hz), 8.42 (1H, s).

8-Hydroxy-5,9a-dimethyl-1,2,3,4,4a,9a-hexahydro-9-fluorenone.

Brown oily substance.

$^1$H-NMR (CDCl$_3$) δ: 1.10-1.70 (6H, m), 1.16 (3H, s), 2.05-2.19 (2H, m), 2.28 (3H, s), 2.98 (1H, dd, J=9.0 Hz, 6 Hz), 6.69 (1H, d, J=8.0 Hz), 7.24 (1H, d, J=8.0 Hz), 8.84 (1H, s).

8-Hydroxy-5-fluoro-1,2,3,4,4a,9a-hexahydro-9-fluorenone.

Melting point: 75°-76° C.

Colorless prism-like crystal (recrystallized from ethanol).

REFERENCE EXAMPLE 27

The following compounds were prepared in the same manner as in Reference Example 10 using suitable starting materials.

8-trans-Crotyloxy-5-methoxy-1,2,3,4,4a,9a-hexahydro-9-fluorenone.

Melting point: 108°–109° C.

Colorless granular crystal (recrystallized from ethanol).

8-(2-cyclohexenyloxy)-5-methyl-1,2,3,4,4a,9a-hexahydro-9-fluorenone.

Light yellow oily substance.

$^1$H-NMR (CDCl$_3$) δ: 0.78 (1H, m), 1.02–1.40 (2H, m), 1.50–1.75 (4H, m), 1.87–2.33 [9H, m, (including 2.31 (3H, s)], 2.45 (1H, m), 2.67 (1H, m), 3.29 (1H, dt, J=6 Hz, 11 Hz), 4.85 (1H, m), 5.87–6.07 (2H, m), 6.75 (1H, d, J=8 Hz), 7.23 (1H, d, J=8 Hz).

8-trans-Crotyloxy-5-fluoro-1,2,3,4,4a,9a-hexahydro-9-fluorenone.

Melting point: 135°–137° C.

Colorless prism-like crystal (recrystallized from ethanol).

8-Crotyloxy-5,9a-dimethyl-1,2,3,4,4a,9a-hexahydro-9-fluorenone.

Light yellow oily substance.

$^1$H-NMR (CDCl$_3$) δ: 0.85–1.75 (6H, m), 1.08 (3H, s), 1.72–1.77 (3H, m), 2.10–2.36 (2H, m), 2.30 (3H, s), 2.91 (1H, dd, J=9 Hz, 6.0 Hz), 4.50–4.60 (2H, m), 5.65–6.00 (2H, m), 6.70 (1H, d, J=8.5 Hz), 7.24 (1H, d, J=8.5 Hz).

REFERENCE EXAMPLE 28

The following compounds were prepared in the same manner as in Reference Example 13 using suitable starting materials.

8-Hydroxy-5-methoxy-7-(1-methyl-2-propenyl)-1,2,3,4,4a,9a-hexahydro-9-fluorenone.

Reddish yellow oily substance.

$^1$H-NMR (CDCl$_3$) δ: 0.97–1.48 [5H, m, including totally 3H of 1.33 (d, J=4 Hz) and 1.36 (d, J=4 Hz)], 1.52–1.68 (4H, m), 2.15–2.40 (2H, m), 2.76 (1H, dt, J=4 Hz, 7.5 Hz), 3.43 (1H, m), 3.81 (3H, s), 3.91 (1H, m), 5.10–5.27 (2H, m), 6.05 (1H, m), 7.04 (1H, s), 8.73 (1H, s).

7-(2-Cyclohexenyl)-8-hydroxy-5-methyl-1,2,3,4,4a,9a-hexahydro-9-fluorenone.

Melting point: 93°–96° C.

Colorless powdery crystal (recrystallized from ethanol).

5-Fluoro-8-hydroxy-7-(1-methyl-2-propenyl)-1,2,3,4,4a,9a-hexahydro-9-fluorenone.

Dark yellow oily substance.

$^1$H-NMR (CDCl$_3$) δ: 1.13–1.73 [9H, m, including totally 3H of 1.32 (d, J=7 Hz) and 1.34 (d, J=7 Hz)], 2.10–2.35 (2H, m), 2.80 (1H, dt, J=4.5 Hz, 7 Hz), 3.51 (1H, m), 3.89 (1H, m), 5.07–5.27 (2H, m), 6.01 (1H, m), 7.05 (1H, d, J=10 Hz), 8.95 (1H, s).

7-(1-Methyl-2-propenyl)-8-hydroxy-5,9a-dimethyl-1,2,3,4,4a,9a-hexahydro-9-fluorenone.

Light brown oily substance.

$^1$H-NMR (CDCl$_3$) δ: 1.05–1.70 (6H, m), 1.15 and 1.53 (3H, s), 1.33 and 1.34 (3H, d, J=7.0 Hz), 2.00–2.20 (2H, m), 2.26 (3H, s), 2.94 (1H, dd, J=9.0 Hz, 6.0 Hz), 3.75–3.95 (1H, m), 5.00–5.15 (2H, m), 5.95–6.20 (1H, m), 7.12 (1H, s), 9.14 and 9.15 (1H, s).

REFERENCE EXAMPLE 29

50.00 Grams of methoxymethyltriphenylphosphnium chloride was suspended in 400 ml of dioxane and 16.37 g of t-BuOK was added thereto under ice-cooling and nitrogen atmosphere, followed by stirring at room temperature for 2 hours. To this dark red solution was added 6.72 g of 8-methoxy-5-methyl-1,2,3,4,4a,9a-hexahydro-9-fluorenone, followed by further stirring at room temperature for 2 hours. Then, the reaction mixture was refluxed for 3 hours and left to stand for cooling. Thereafter, 400 ml of water was added and extraction was effected with diethyl ether. The organic layer was dried with magnesium sulfate, filtered and concentrated. The residue was purified by a silica gel column chromatography (eluent:n-hexane) to obtain 4.54 g of 8-methoxy-9-methoxymethylene-5-methyl-1,2,3,4,4a,9a-hexahydrofluorene which was a yellow oily substance.

$^1$H-NMR (CDCl$_3$) δ: 1.18–1.63 (m, 5H), 1.67–1.93 (m, 2H), 2.20 (m, 1H), 2.23 (s, 3H), 3.00–3.18 (m, 2H), 3.68 (s, 3H), 3.85 (s, 3H), 6.59 (d, J=7.5 Hz, 1H), 6.81 (d, J=7.5 Hz, 1H), 7.15 (d, J=2.5 Hz, 1H).

The following compound was prepared in the same manner as in Reference Example 29 using suitable starting material.

5,7-Dimethyl-8-methoxy-9-methoxymethylene-1,2,3,4,4a,9a-hexahydrofluorene.

Yellow oily substance.

$^1$H-NMR (CDCl$_3$) δ: 1.20–1.97 (m, 7H), 2.10–2.40 (m, 1H), 2.25 (s, 3H), 2.27 (s, 3H), 3.00–3.23 (m, 2H), 3.73 (s, 3H), 3.74 (s, 3H), 6.74 (s, 1H), 7.15 (d, J=2.5 Hz, 1H).

REFERENCE EXAMPLE 30

4.54 Grams of 8-methoxy-9-methoxymethylene-5-methyl-1,2,3,4,4a,9a-hexahydrofluorene was dissolved in 200 ml of 1,4-dioxane and 50 ml of water. To the solution was added 0.90 g of p-toluenesulfonic acid monohydrate and this was refluxed for 18 hours. To the reaction mixture was added 200 ml of water and extraction was carried out with diethyl ether. The organic layer was dried with magnesium sulfate, filtered and concentrated and the residue was purified by a silica gel column chromatography (eluent: ethyl acetate:n-hexane=1:10) and recrystallized from ethanol to obtain 3.94 g of 9-formyl-8-methoxy-5-methyl-1,2,3,4,4a,9a-hexahydrofluorene having a melting point of 92°–93° C. and of colorless needle-like crystal.

The following compound was prepared in the same manner as in Reference Example 30 using a suitable starting material.

5,7-Dimethyl-9-formyl-8-methoxy-1,2,3,4,4a,9a-hexahydrofluorene.

Melting point: 98°–100° C.

Colorless prism-like crystal (recrystallized from ethanol).

REFERENCE EXAMPLE 31

A mixture of 15 ml of acetic anhydride and 50 ml of acetic acid was ice-cooled and thereto was added dropwise 10 ml of nitric acid (d=1.38). After stirring for 1 hour, thereto was added dropwise an acetic acid solution containing 10 g of 8-hydroxy-5-methyl-1,2,3,4,4a,9a-hexahydro-9-fluorenone in 100 ml of acetic acid. After stirring for 30 minutes, the ice bath was removed and the solution was warmed to an inner temperature of 15° C. To this solution was added 150 ml of diethyl ether, followed by stirring under ice-cooling. The resulting precipitate was collected by filtration to obtain 8 g of 8-hydroxy-5-methyl-7-nitro-1,2,3,4,4a,9a-hexahydro-9-fluorenone of yellowish green powdery crystal.

REFERENCE EXAMPLE 32

To 200 ml of ethanol were added 5.0 g of 8-hydroxy-5-methyl-7-nitro-1,2,3,4,4a,9a-hexahydro-9-fluorenone and 1 g of 5% palladium carbon and catalytic reduction was carried out at room temperature and under normal pressure. The catalyst was removed by filtration and the filtrate was concentrated to obtain 3.5 g of 7-amino-8-hydroxy-5-methyl-1,2,3,4,4a,9a-hexahydro-9-fluorenone (yellow crystal).

$^1$H-NMR (CDCl$_2$) δ: 0.80-1.75 (6H, m), 2.10-2.40 (2H, m), 2.22 (3H, s), 2.78 (1H, dt, J=3.0, 7.0 Hz), 3.29 (1H, dt, J=11.0, 6.5 Hz), 3.6 (2H, br), 6.73 (1H, s), 8.62 (1H, br, s).

REFERENCE EXAMPLE 33

1.0 Gram of 7-amino-8-hydroxy-5-methyl-1,2,3,4,4a,-9a-hexahydro-9-fluorenone was dissolved in 30 ml of ethanol and 0.5 ml of acetic anhydride was added. The solution was stirred at room temperature for 1 hour. After disappearance of the color formed by ninhydrin was confirmed on a thin-layer chromatography, the reaction mixture was concentrated. To the residue was added diisopropyl ether and the resulting precipitate was collected by filtration to obtain 0.8 g of 7-acetylamino-8-hydroxy-5-methyl-1,2,3,4,4a,9a-hexahydro-9-fluorenone (light brown crystal).

$^1$H-NMR (CDCl$_3$) δ: 0.80-1.75 (6H, m), 2.20-2.40 (2H, m), 2.21 (3H, s), 2.30 (3H, s), 2.80 (1H, dt, J=3.0, 7.0 Hz), 3.36 (1H, dt, J=11.0, 6.5 Hz), 7.47 (1H, br, s), 8.30 (1H, s), 8.87 (1H, s).

REFERENCE EXAMPLE 34

The following compound was prepared in the same manner as in Reference Example 8 using a suitable starting material.

8-Methoxy-5,9a-dimethyl-1,2,3,4,4a,9a-hexahydro-9-fluorenone.

Colorless powdery crystal (recrystallized from ethanol).

$^1$H-NMR (CDCl$_3$) δ: 0.9-1.68 (6H, m), 1.09 (3H, s), 2.10-2.45 (2H, m), 2.31 (3H, s), 2.92 (1H, dd, J=9.0 Hz, 6.0 Hz), 3.91 (3H, s), 6.70 (1H, d, J=8.5 Hz), 7.29 (1H, d, J=8.5 Hz).

REFERENCE EXAMPLE 35

The following compound was prepared in the same manner as in Reference Example 17 using a suitable starting material.

7-tert-Butyl-8-hydroxy-5,9a-dimethyl-1,2,3,4,4a,9a-hexahydro-9-fluorenone.

Light brown oily substance.

$^1$H-NMR (CDCl$_3$) δ: 1.10-1.70 (6H, m), 1.16 (3H, s), 1.40 (9H, s), 2.03-2.20 (2H, m), 2.27 (3H, s), 2.93 (1H, dd, J=8.5 Hz, 6.0 Hz), 7.23 (1H, s), 9.67 (1H, s).

EXAMPLE 1

7.99 Grams of hydroxylamine hydrochloride was added to a solution prepared by dissolving 17.22 g of 5,7-dimethyl-8-hydroxy-1,2,3,4,4a,9a-hexahydro-9-fluorenone in 100 ml of pyridine and the mixture was refluxed under heating for 2 hours. Pyridine was distilled off under reduced pressure and the resulting residue was extracted with 300 ml of chloroform. The extract was washed with water 1% hydrochloric acid and then with saturated aqueous sodium chloride solution and then dried with anhydrous magnesium sulfate. After the solvent was distilled off, the product was recrystallized from ethanol to obtain 11.56 g of 5,7-dimethyl-8-hydroxy-1,2,3,4,4a,9a-hexahydro-9-fluorenone oxime as a mixture of syn-isomer and anti-isomer.

Melting point: 137°-139° C.

Light yellow powdery crystal.

1.83 Gram of the product was purified by a silica gel column chromatography (eluent: methylene chloride) to obtain 810 mg of isomer (A) and 400 mg of isomer (B).

Isomer (A):

Melting point: 155°-156° C.

Yellow powdery crystal (recrystallized from ethanol).

$^1$H-NMR (CDCl$_3$) δ: 1.37-1.69 (8H, m), 2.20 (3H, s), 2.22,(3H, s), 3.33 (2H, m), 6.71 (1H, s), 6.88 (1H, s), 8.67 (1H, s).

Isomer (B):

Melting point: 143°-144° C.

Yellow needle-like crystal (recrystallized from ethanol).

$^1$H-NMR (CDCl$_3$) δ: 0.90 (1H, m), 1.06-2.35 (7H), 2.20 (3H, s), 2.22 (3H, s), 3.07 (2H, m), 7.02 (1H, s), 9.70 (2H, brs).

EXAMPLES 2-7

The following compounds were prepared in the same manner as in Example 1 using suitable starting materials.

TABLE 3

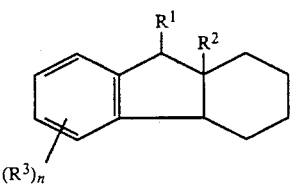

| Example No. | R$^1$ | R$^2$ | R$^3$ | n | Crystal form (Solvent for recrystallization) | Melting point (°C.) |
| --- | --- | --- | --- | --- | --- | --- |
| 2 | =N—OH | CH$_3$ | 5-CH$_3$<br>7-CH$_3$<br>8-OH | 3 | Light purple powder (Ethanol) | 132-133 |
| 3 | =N—OH | H | 5-CH$_3$ | 3 | Light yellow | 148-149 |

TABLE 3-continued

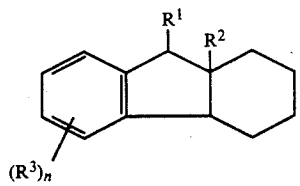

| Example No. | R¹ | R² | R³ | n | Crystal form (Solvent for recrystallization) | Melting point (°C.) |
|---|---|---|---|---|---|---|
| 4 | =N—OH | H | 7-C(CH₃)₃<br>8-OH<br>5-CH₃ | 3 | granule (n-hexane)<br>Isomer A; Dark yellow oily substance<br>Isomer B; Reddish orange oily substance | |
| 5 | =N—OH | H | 7-CH(CH=CH₂)(C₆H₅)<br>8-OH<br>5-CH₃<br>7-CH(CH=CH₂)(CH₃)<br>8-OH | 3 | Colorless neddle-like crystal (n-hexane) | 120–121.5 |
| 6 | =N—OH | H | 5-CH₃<br>7-CH₂CH=CH₂<br>8-OH | 3 | Light yellow powdery crystal (n-hexane) | 90–91 |
| 7 | =N—OH | H | 5-CH₃<br>8-OH | 2 | Light yellow granular crystal (Ethanol) | 164–166 |

NMR data of the compound of Example 4 in Table 3 are shown below.

¹H-NMR (CDCl₃) δ:
Isomer (A); 1.19–2.27 (8H, m), 2.21 (3H, s), 3.17–3.40 (2H, m), 3.45–3.55 (1H, m), 4.88–5.27 (2H, m), 6.23–6.46 (1H, m), 6.80–7.39 (7H, m), 8.88–9.06 (1H, br).
Isomer (B); 0.98–1.23 (1H, m), 1.37–2.02 (5H, m), 2 20–2.59 (2H, m), 2.40, 2.42, 2.44 (3H, s), 3 19–3.40 (2H, m), 5.12–5.25 (1H, m), 5.29–5.47 (2H, m), 6.44–6.69 (1H, m), 7.09–7.63 (7H, m), 9.29–10.31 (1H, br).

EXAMPLE 8

1.69 Gram of platinum oxide was added to an acetic acid solution containing 16.91 g of 5,7-dimethyl-8-hydroxy-1,2,3,4,4a,9a-hexahydro-9-fluorenone-oxime in 400 ml of acetic acid and then the solution was subjected to catalytic reduction at room temperature under an initial pressure of 3 atm. for 5 hours. After the catalyst was removed by filtration, the filtrate was concentrated to dryness under reduced pressure. The residue was dissolved in 300 ml of chloroform and the chloroform solution was washed with saturated aqueous sodium bicarbonate solution, water and saturated aqueous sodium chloride solution in this order and dried with anhydrous magnesium sulfate. Thereafter, chloroform was distilled off under reduced pressure. The resulting residue was dissolved in 100 ml of ethanol and pH was adjusted to about 2–3 with addition of hydrochloric acid gas saturated ethanol. The solvent was concentrated to dryness under reduced pressure and the residue was recrystallized from ethanol to obtain 12.86 g of 9-amino-5,7-dimethyl-8-hydroxy-1,2,3,4,4a,9a-hexahydrofluorene hydrochloride.

10 Melting point: 196°–198° C.
Colorless needle-like crystal.

EXAMPLES 9–14

The following compounds were prepared in the same manner as in Example 8 using suitable starting materials. The results are shown in Table 4.

TABLE 4

[Structure: fluorene-based skeleton with R¹, R² at 9-position, R⁴a, and (R³)ₙ substituents]

| Example No. | R¹ | R² | R³ | n | Crystal form (Recrystallization solvent) | Melting point (°C.) | Salt form |
|---|---|---|---|---|---|---|---|
| 9 | $NH_2$ | H | 5-$CH_3$<br>7-C(CH₃)₃<br>8-OH | 3 | Colorless powdery crystal (Ethanol) | 198–201 (dec.) | HCl |
| 10 | $NH_2$ | H | 5-$CH_3$<br>8-OH | 2 | Colorless needle-like crystal (Ethanol) | 191–201 (dec.) | HCl |
| 11 | $NH_2$ | H | 5-$CH_3$<br>7-CH(CH₃)(CH₂CH₃)<br>8-OH | 3 | Colorless flaky crystal (Ethanol) | 159.5–161 | HCl |
| 12 | $NH_2$ | H | 5-$CH_3$<br>7-$CH_2CH_2CH_3$<br>8-OH | 3 | Colorless powdery crystal (Ethanol) | 166–168 (dec.) | HCl |
| 13 | $NH_2$ | H | 5-$CH_3$<br>7-CH(CH₂CH₃)(cyclohexyl)<br>8-OH | 3 | Colorless powdery crystal (Methanol-diethyl ether) | 169–172 (dec.) | HCl |
| 14 | $NH_2$ | H | 5-$CH_3$<br>7-CH(CH₂CH₃)(phenyl)<br>8-OH | 3 | Colorless powdery crystal (Ethanol) | 133–134 | HCl |

EXAMPLE 15

To a methanol solution containing 2 g of 8-hydroxy-5-methyl-1,2,3,4,4a,9a-hexahydro-9-fluorenone in 20 ml of methanol was added 7.18 ml of methanol solution of 40% methylamine and the mixture was refluxed under heating for 5 hours. After left to stand for cooling, the solvent was removed by concentration and the residue was recrystallized from ethanol to obtain 0.35 g of 8-hydroxy-5-methyl-9-methylimino-1,2,3,4,4a,9a-hexahydrofluorene.

Melting point: 227°–230° C. (dec.)
Yellow powdery crystal.

EXAMPLES 16–19

The following compounds were prepared in the same manner as in Example 15 using suitable starting materials. The results are shown in Table 5.

TABLE 5

[Structure: fluorene-based skeleton with R¹, R² and (R³)ₙ]

| Example No. | R¹ | R² | R³ | n | Crystal form (Recrystallization solvent) | Melting point (°C.) | Salt form |
|---|---|---|---|---|---|---|---|
| 16 | =N—$CH_3$ | H | 5-$CH_3$<br>7-$CH_3$<br>8-OH | 8 | Yellow-powdery crystal (Ethanol) | 113–114 | — |
| 17 | =N—$CH_3$ | H | 5-$CH_3$ | 3 | Yellow prism-like | 125–126 | — |

TABLE 5-continued

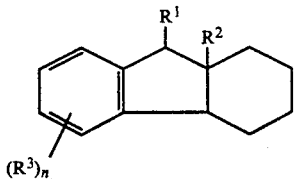

| Example No. | R¹ | R² | R³ | n | Crystal form (Recrystallization solvent) | Melting point (°C.) | Salt form |
|---|---|---|---|---|---|---|---|
| 18 | =N—C₂H₅ | H | 7-C(CH₃)₃<br>8-OH<br>5-CH₃ | 3 | crystal (Methanol)<br>Colorless powdery crystal (Methanol-diethyl ether) | 127–131 (dec.) | HCl |
| 19 | =N—CH₃ | H | 7-C(CH₃)₃<br>8-OH<br>5-CH₃<br>7-Br<br>8-OH | 3 | Yellow needle-like crystal (Methanol) | 183–186 | — |

EXAMPLE 20

3.4 Milliliters of a methanol solution of 40% methylamine was added to a methanol solution containing 2 g of 5,7-dimethyl-8-hydroxy-1,2,3,4,4a,9a-hexahydro-9-fluorenone in 20 ml of methanol and the mixture was refluxed under heating for 4 hours. Then, thereto were further added 10 ml of methanol and 3.4 ml of a methanol solution of 40% methyl amine, followed by refluxing for 6 hours. After left to stand for cooling, 3.66 g of sodium borohydride was gradually added thereto with stirring at room temperature, followed by stirring for 1 hour at the same temperature. Then, water was added to the reaction mixture and extraction was effected with chloroform. The organic layer was dried with magnesium sulfate and then the solvent was distilled off. The residue was purified by a silica gel column chromatography (eluent: ethyl acetate:n-hexane=1:1) and then recrystallized from ethanol to obtain 0.70 g of 5,7-dimethyl-8-hydroxy-9-methylamino-1,2,3,4,4a,9a-hexahydrofluorene.

Melting point: 110°–111° C.
Colorless powdery crystal.

EXAMPLE 21

2.0 Grams of 5,7-dimethyl-8-hydroxy-1,2,3,4,4a,9a-hexahydro-9-fluorenone, 6 ml of 2-aminomethyl-1-ethylpyrrolidine and 20 ml of benzene were refluxed with heating for 5 days using a water separator. Benzene was distilled off under reduced pressure and the residue was dissolved in 50 ml of methanol. To the solution was added gradually 4.0 g of sodium borohydride at room temperature and the mixture was refluxed with heating for 4 hours. The solvent was distilled off under reduced pressure and to the residue was added 100 ml of water and extraction was effected with 200 ml of ethyl acetate. The extract was washed with water and dried and then the solvent was removed by concentration under reduced pressure. The residue was purified by a silica gel column chromatography (eluent: ethyl acetate:n-hexane=1:1) to obtain 0.3 g of isomer (A) and 0.31 g of isomer (B) of 5,7-dimethyl-8-hydroxy-9-(1-ethyl-2-pyrrolidonyl)methylamino-1,2,3,4,4a,9a-hexahydrofluorene and 1.10 g of a mixture of (A) and (B).

Isomer (A):
 Melting point: 75°–76° C.
 Colorless needle-like crystal (recrystallized from methanol).
 ¹H-NMR (CDCl₃) δ: 1.06 (3H, t, J=7.2 Hz), 1.00–2.24 (m), 2.16 (3H, s), 2.24 (3H, s), 2.50–2.86 (6H, m), 3.15 (2H, m), 4.16 (1H, dd, J=12.4 Hz, 5.6 Hz), 6.70 (1H, s).

Isomer (B):
 Melting point: 113°–114° C.
 Colorless needle-like crystal (recrystallized from ethanol).
 ¹H-NMR (CDCl₃) δ: 1.10 (3H, t), 1.05–2.33 (m), 2.44–2.56 (4H, m), 2.76–2.92 (2H, m), 3.12–3.19 (2H, m), 4.16 (1H, dd, J=9.0 Hz, 5.2 Hz), 6.70 (1H, s).

EXAMPLES 22-52

The following compounds were prepared in the same manner as in Examples 20 and 21 using suitable starting materials. The results are shown in Table 6.

TABLE 6

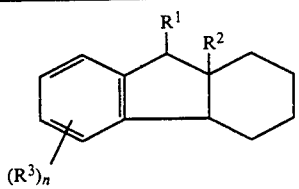

| Example No. | R¹ | R² | R³ | n | Crystal form (Recrystallization solvent) | Melting point (°C.) | Salt form |
|---|---|---|---|---|---|---|---|
| 22 | —NHCH$_3$ | H | 5-CH$_3$<br>8-OH | 2 | Colorless prism-like<br>(Ethanol) | 120–121 | — |
| 23 | —NH—cyclohexyl | H | 5-CH$_3$<br>8-OH | 2 | Colorless powdery substance<br>(Ethanol) | 169–170 | HCl |
| 24 | —NHCH$_2$—phenyl | H | 5-CH$_3$<br>8-OH | 2 | Colorless prism-like<br>(Ethanol) | 143–144 | HCl |
| 25 | —NHCH$_2$CH$_3$ | H | 5-CH$_3$<br>7-CH$_3$<br>8-OH | 3 | Colorless needle-like crystal<br>(Ethanol) | 91–92 | — |
| 26 | —NHCH$_2$CH$_2$CH$_3$ | H | 5-CH$_3$<br>7-CH$_3$<br>8-OH | 3 | Colorless powdery crystal<br>(Ethanol-acetone) | 162–163 | HCl |
| 27 | —NHCH$_2$(CH$_2$)$_4$CH$_3$ | H | 5-CH$_3$<br>7-CH$_3$<br>8-OH | 2 | Colorless powdery crystal<br>(Ethanol-acetone) | 139–140 | HCl |
| 28 | —NHCH$_2$(CH$_2$)$_6$CH$_3$ | H | 5-CH$_3$<br>7-CH$_3$<br>8-OH | 3 | Colorless needle-like crystal<br>(Ethanol) | 139–141 | HCl |
| 29 | —NHCH$_2$CH=CH$_2$ | H | 5-CH$_3$<br>7-CH$_3$<br>8-OH | 3 | Colorless powdery crystal<br>(Ethanol-diethyl ether) | 156–158 | HCl |
| 30 | —NHCH(CH$_3$)$_2$ | H | 5-CH$_3$<br>7-CH$_3$<br>8-OH | 3 | Colorless needle-like crystal<br>(Ethanol) | 96–97 | — |
| 31 | —NH—cyclopropyl | H | 5-CH$_3$<br>7-CH$_3$<br>8-OH | 3 | Colorless needle-like crystal<br>(Ethanol) | 107–108 | — |
| 32 | —NHCH$_2$—phenyl | H | 5-CH$_3$<br>7-CH$_3$<br>8-OH | 3 | Colorless needle-like crystal<br>(Ethanol) | 131–132 | — |
| 33 | —NH—phenyl | H | 5-CH$_3$<br>7-CH$_3$<br>8-OH | 3 | Colorless needle-like crystal<br>(Ethanol) | 130–131 | — |
| 34 | —NH—cyclopentyl | H | 5-CH$_3$<br>7-CH$_3$<br>8-OH | 3 | Colorless needle-like crystal<br>(Ethanol) | 101–103 | — |
| 35 | —NHCH$_3$ | H | 5-CH$_3$<br>7-CHCH=CH$_2$ (CH$_3$)<br>8-OH | 3 | Colorless powdery crystal<br>(Ethanol) | 184.5–186 | HCl |

TABLE 6-continued

| Example No. | R¹ | R² | R³ | n | Crystal form (Recrystallization solvent) | Melting point (°C.) | Salt form |
|---|---|---|---|---|---|---|---|
| 36 | —NHCH$_2$CH$_3$ | H | 5-CH$_3$<br>7-CHCH=CH$_2$ (with CH$_3$ branch)<br>8-OH | 3 | Colorless needle-like crystal (Ethanol) | 169–171 (dec.) | HCl |
| 37 | —NHCH$_3$ | H | 5-CH$_3$<br>7-CHCH=CH$_2$ (with CH$_3$ branch)<br>8-OCH$_3$ | 3 | Colorless needle-like crystal (Ethanol) | 263–264 (dec.) | HCl |
| 38 | —NHCH$_2$CH$_3$ | H | 5-CH$_3$<br>7-CH$_2$CH=CH$_2$<br>8-OH | 3 | Colorless powdery crystal (Ethanol) | 171–172.5 (dec.) | HCl |
| 39 | —NHCH$_2$CH$_2$OH | H | 5-CH$_3$<br>7-CH$_2$CH=CH$_2$<br>8-OH | 3 | Colorless powdery crystal (Ethanol) | 147–148.5 (dec.) | HCl |
| 40 | —NHCH$_3$ | H | 5-CH$_3$<br>7-CH$_2$CH=CH$_2$<br>8-OH | 3 | Colorless needle-like crystal (Ethanol) | 169 (dec.) | HCl |
| 41 | —NHCH$_3$ | H | 5-CH$_3$<br>7-CH(Ph)CH=CH$_2$<br>8-OH | 3 | Colorless powdery crystal (Ethanol-water) | 166–168 | HCl |
| 42 | —NHCH$_3$ | H | 5-CH$_3$<br>7-C(CH$_3$)$_3$<br>8-OH | 3 | Colorless needle-like crystal (Ethanol) | 198–199 | HCl |
| 43 | —NHCH$_3$ | H | 5-CH$_3$<br>7-CH$_2$N(CH$_3$)$_2$<br>8-OH | 3 | Colorless powdery crystal (Ethanol) | 212–213 (dec.) | 2HCl |
| 44 | —NHCH$_2$CH$_3$ | H | 5-CH$_3$<br>7-C(CH$_3$)$_3$<br>8-OH | 3 | Colorless prism-like crystal (Ethanol) | 135–137 | — |
| 45 | —NH—(piperidin-4-yl)-N—CH$_2$—Ph | H | 5-CH$_3$<br>7-CH$_3$<br>8-OH | 3 | Colorless needle-like crystal (Methanol) | 126–127 | — |
| 46 | —NH—(piperidin-4-yl)-N—CH$_2$—Ph | H | 5-CH$_3$<br>7-CH$_3$<br>8-OH | 3 | Colorless powdery crystal (Methanol) | 119–120 | — |
| 47 | —NHCH$_3$ | OCH$_3$ | 5-CH$_3$ | 3 | Colorless granular | 170–171 | — |

TABLE 6-continued

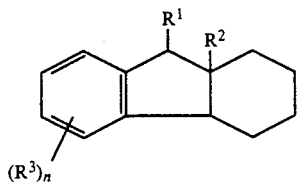

| Example No. | R¹ | R² | R³ | n | Crystal form (Recrystallization solvent) | Melting point (°C.) | Salt form |
|---|---|---|---|---|---|---|---|
| 48 | —NHCH₃ | OCH₃ | 7-Br<br>8-OH<br>5-CH₃<br>7-Br<br>8-OH | 3 | crystal<br>(Ethanol)<br>Colorless flaky crystal<br>(Ethanol) | 158–160 | — |
| 49 | —N(CH₃)₂ | H | 5-CH₃<br>7-CH(CH₃)CH=CH₂<br>8-OCH₃ | 3 | Colorless powdery crystal<br>(Ethanol diethyl ether-n-hexane) | 186–189 | HCl |
| 50 | —NHCH₃ | H | 5-CH₃<br>7-CH₃<br>8-OCH₃ | 3 | Colorless columnar crystal<br>(Ethanol) | 230–232 (dec.) | HCl |
| 51 | —N(CH₃)(C₂H₅) | H | 5-CH₃<br>7-CH(CH₃)CH=CH₂<br>8-OH | 3 | Colorless powdery crystal<br>(Ethanol) | 134–136 | HCl |
| 52 | —N(CH₃)₂ | H | 5-CH₃<br>7-CH(CH₃)CH=CH₂<br>8-OH | 3 | Colorless needle-like crystal<br>(Ethanol) | 164–166 (dec.) | HCl |

NMR data of the compound of Example 45 in Table 6 are as follows:

¹H-NMR (CDCl₃) δ: 0.92–1.90 (m), 1.97–2.28 (m), 2.15 (3H, s), 2.23 (3H, s), 2.41–2.74 (3H, m), 2.83 (2H, m), 3.14 (1H, brs), 3.15 (2H, s), 4.33 (1H, dd, J=13.0 Hz, 5.8 Hz), 6.69 (1H, s), 7.27 (5H, m).

NMR data of the compound of Example 46 in Table 6 are as follows:

¹H-NMR (CDCl₃) δ: 0.93 (1H; m), 1.18–1.82 (m), 1.83–2.40 (m), 2.13 (3H, s), 2.16 (3H, s), 2.78–2.93 (4H, m), 3.50 (2H, s), 4.49 (1H, t, J=9.6 Hz), 6.74 (1H, s), 7.27 (5H, m).

EXAMPLE 53

2.5 Milliliters of a methanol solution of 40% methylamine was added to a methanol solution containing 2 g of 7,9a-dibromo-8-hydroxy-5-methyl-1,2,3,4,4a,9a-hexahydro-9-fluorenone in 20 ml of methanol and the mixture was refluxed with heating for 8 hours. The reaction mixture was left to stand for cooling and then thereto was added gradually 2.90 g of sodium borohydride, followed by stirring at room temperature for 1 hour. Water was added to the reaction mixture and the mixture was rendered alkaline with 10% aqueous sodium hydroxide solution and then was extracted with chloroform. The organic layer was dried with magnesium sulfate and then the solvent was distilled off. The residue was purified by a silica gel column chromatography (eluent: ethyl acetate:n-hexane=1:5) to obtain 0.40 g of isomer (A) and 0.13 g of isomer (B) of 7-bromo-8-hydroxy-9a-methoxy-5-methyl-9-methylamino-1,2,3,4,4a,9a-hexahydrofluorene.

Isomer (A):

Melting point: 170°–171° C.

Colorless granular crystal (recrystallized from ethanol).

¹H-NMR (CDCl₃) δ: 0.93–1.83 (8H, m), 2.23 (3H, s), 2.67 (3H, s), 3.27–3.47 (1H, m), 3.39 (3H, m), 4.36 (1H, s), 7.06 (1H, s).

Isomer (B):

Melting point: 158°–160° C.

Colorless flaky crystal (recrystallized from ethanol).

¹H-NMR (CDCl₃) δ: 0.82–2.07 (8H, m), 2.15 (3H, s), 2.68 (3H, s), 2.99 (1H, t, J=6 Hz), 4.38 (1H, s), 7.08 (1H, s).

EXAMPLE 54

3.7 Grams of 60% sodium hydride was added to a dimethylformamide solution containing 8.82 g of 7-(1-methyl-2-propenyl)-8-hydroxy-5-methyl-9-methylamino-1,2,3,4,4a,9a-hexahydrofluorene in 80 ml of dimethylformamide and the mixture was stirred at room temperature for 1 hour. Then, the reaction mixture was ice-cooled and thereto was added 5.8 ml of methyl iodide with stirring, followed by stirring at room temperature for 3 hours. The reaction mixture was extracted with chloroform-water and dried with magnesium sulfate and then the solvent was removed by concentration. The residue was purified by a silica gel column chromatography (eluent: n-hexane→ethyl acetate:n-hexane=1:4) and then dissolved in ethanol and thereto was added a saturated hydrochloric acid gas-ethanol solution to obtain a hydrochloride. This hydrochloride was recrystallized from ethanol-diethyl ether-n-hexane to obtain 8.63 g of 9-dimethylamino-8-methoxy-7-(1-methyl-2-propenyl)-5-methyl-1,2,3,4,4a,-9a-hexahydrofluorene hydrochloride.

Melting point: 186°-189° C.

Colorless powdery crystal.

Compounds of said Examples 20-32, 34-48 and 50-52 and Examples 119-134, 139-141, 144-145C., 168-173, and 175-178 given hereinafter were prepared in the same manner as in Example 54 using suitable starting materials.

EXAMPLE 55

0.16 Gram of 60% sodium hydride was added to a dimethylformamide solution containing 0.42 g of 5,7-dimethyl-8-hydroxy-9-methylamino-1,2,3,4,4a,9a-hexahydrofluorene in 5 ml of dimethylformamide, followed by stirring at room temperature for 30 minutes. Then, to the mixture was added 0.13 ml of methyl iodide, followed by stirring at the same temperature for 30 minutes. Water was added to the reaction mixture and extraction was carried out with chloroform. The chloroform layer was dried with magnesium sulfate and then the solvent was removed by concentration. The residue was purified by a silica gel column chromatography (eluent: ethyl acetate:n-hexane=1:4), then was dissolved in ethanol and converted to a hydrochloride with saturated hydrochloric acid gas-ethanol solution, which was recrystallized from ethanol to obtain 0.1 g of 5,7-dimethyl-8-methoxy-9-methylamino-1,2,3,4,4a,9a-hexahydrofluorene hydrochloride.

Melting point: 230°-232° C. (dec.).

Colorless columnas crystal.

Compounds of said Examples 37 and 49 and Examples 75, 121, 122, 125, 126, 131, 145, 145A, 168-176 and 178 given hereinafter were prepared in the same manner as in Example 55 using suitable starting materials.

EXAMPLE 56

2.0 Milliliters of acetic anhydride and 1.0 ml of 98% formic acid were mixed and the mixture was stirred under heating for 2 hours and left to stand of cooling. To the resulting solution were added 3.0 g of 8-hydroxy-5-methyl-9-methylamino-7-(1-methyl-2-propenyl)-1,2,3,4,4a,9a-hexahydrofluorene hydrochloride and 10 ml of acetic anhydride and reaction was carried out at 60° C. for 2 hours and at room temperature for 15 hours. To the reaction mixture was added water and the separated solid was collected by filtration, washed with water and once dissolved in chloroform and the solution was dried with magnesium sulfate. The solvent was distilled off and the residue was recrystallized from ethanol to obtain 1.42 g of 8-hydroxy-5-methyl-9-(N-methyl-N-formylamino)-7-(1-methyl-2-propenyl)-1,2,3,4,4a,9a-hexahydrofluorene.

Melting point: 158°-159° C.

Colorless powdery crystal.

EXAMPLE 57

5.4 Milliliters of triethylamine and then 1.43 ml of acetyl chloride were added dropwise to a solution of a chloroform solution containing 5.0 g of 8-hydroxy-5-methyl-9-methylamino-7-(1-methyl-2-propenyl)-1,2,3,4,4a,9a-hexahydrofluorene hydrochloride with stirring under ice-cooling, followed by stirring at room temperature for 1 hour. Water was added to the reaction mixture and extraction was effected with chloroform. The extract was dried with magnesium sulfate and the solvent was distilled off. The residue was purified by a silica gel column chromatography (eluent: ethyl acetate:n-hexane=1:4) and then recrystallized from ethanol to obtain 4.36 g of 8-hydroxy-5-methyl-9-(N-methyl-N-acetylamino)-7-(1-methyl-2-propenyl)-1,2,3,4,4a,9a-hexahydrofluorene.

Melting point: 166°-168° C.

Colorless granular crystal (recrystallized from ethanol).

EXAMPLES 58-62

The following compounds were prepared in the same manner as in Examples 56 and 57 using suitable starting materials. The results are shown in Table 7.

TABLE 7

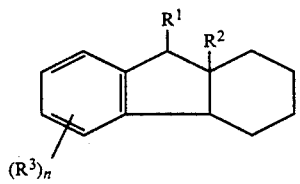

| Example No. | $R^1$ | $R^2$ | $R^3$ | n | Crystal form (Recrystallization solvent) | Melting point (°C.) | Salt form |
|---|---|---|---|---|---|---|---|
| 58 | —NHCOCH$_3$ | H | 5-CH$_3$ 7-CH$_3$ 8-OH | 3 | Colorless powdery crystal (Ethanol) | 166-167 | — |
| 59 | —NHCOCH$_2$Cl | H | 5-CH$_3$ 7-CH$_3$ 8-OH | 3 | Light yellow oily substance | — | — |

TABLE 7-continued

[Structure: fluorene core with R¹, R² at 9-position and (R³)ₙ substituents]

| Example No. | R¹ | R² | R³ | n | Crystal form (Recrystallization solvent) | Melting point (°C.) | Salt form |
|---|---|---|---|---|---|---|---|
| 60 | CH₃<br>\|<br>—N—COCH₂Cl | H | 5-CH₃<br>7-CH(CH₃)(CH=CH₂)<br>8-OH | 3 | Colorless needle-like crystal (Methanol) | 101–102 (dec.) | — |
| 61 | —NHCOCH₂Cl | H | 5-CH₃<br>7-C(CH₃)₂CH₃<br>8-OH | 3 | Colorless prism-like crystals (Ethanol) | 200–201 | — |
| 62 | —NHCOCH₂Cl | H | 5-CH₃<br>8-OH | 2 | Yellow oily substance | — | — |

NMR data of the compound of Example 59 in Table 7 are as follows:

¹H-NMR (CDCl₃) δ: 0.93 (1H, m), 1.22–1.45 (4H, m), 1.57–2.39 (5H, m), 2.19 (3H, s), 2.20 (3H, s), 2.72 (1H, m), 2.98 (1H, m), 4.09 (2H, d, J=6 Hz), 5.16 (1H, t, J=7.8 Hz), 6.85 (1H, s), 7.52 (1H, d, J=9.4 Hz), 8.48 (1H, brs).

NMR data of the compound of Example 62 in Table 7 are as follows:

¹H-NMR (CDCl₃) δ: 0.77–2.03 (8H, m), 2.21 (3H, s), 2.47–3.14 (2H, m), 4.05 (2H, s), 5.14 (1H, dd, J=7.5 Hz, 7.5 Hz), 6.60 (1H, d, J=7.5 Hz), 6.90 (1H, d, J=7.5 Hz), 7.43 (1H, d, J=7.5 Hz), 8.40 (1H, s).

EXAMPLE 63

0.97 Gram of 9-chloroacetyl-5,7-dimethyl-8-hydroxy-1,2,3,4,4a,9a-hexahydrofluorene, 20 ml of acetonitrile, 0.6 ml of triethylamine and 0.73 g of 4-(3-methoxyphenyl)piperazine were mixed and refluxed with heating for 4 hours. The solvent was distilled off and the residue was extracted with water-dichloromethane. The dichloromethane layer was dried with magnesium sulfate and then the solvent was distilled off. The residue was purified by a silica gel column chromatography (eluent: ethyl acetate:n-hexane=1.5), then converted to a hydrochloride with ethanol-hydrochloric acid and recrystallized from ethanol to obtain 1.21 g of 5,7-dimethyl-8-hydroxy-9-[4-(3-methoxyphenyl)-1-piperazinyl]acetylamino-1,2,3,4,4a,9a-hexahydrofluorene hydrochloride.

Melting point: 189°–192° C.

Colorless powdery crystal.

EXAMPLES 64–71

The following compounds were prepared in the same manner as in Example 63 using suitable starting materials. The results are shown in Table 8.

TABLE 8

[Structure: fluorene core with R¹, R² at 9-position and (R³)ₙ substituents]

| Example No. | R¹ | R² | R³ | n | Crystal form (Recrystallization solvent) | Melting point (°C.) | Salt form |
|---|---|---|---|---|---|---|---|
| 64 | —NHCOCH₂N(CH₂CH₂)₂N—CH₃ | H | 5-CH₃<br>7-CH₃<br>8-OH | 3 | Colorless powdery crystals (Ethanol) | 158–159 | — |

TABLE 8-continued

Structure: fluorene-type core with R¹, R² at position 9/9a, (R³)ₙ substituents on aromatic ring

| Example No. | R¹ | R² | R³ | n | Crystal form (Recrystallization solvent) | Melting point (°C.) | Salt form |
|---|---|---|---|---|---|---|---|
| 65 | —NHCOCH₂N(piperazinyl)—C₆H₄—Cl (3-Cl) | H | 5-CH₃, 7-CH₃, 8-OH | 3 | Colorless powdery crystals (Ethanol) | 144–146 | HCl |
| 66 | —NHCOCH₂N(piperazinyl)N—CH₂C≡CH | H | 5-CH₃, 7-CH₃, 8-OH | 3 | Colorless powdery crystals (Ethanol) | 157–159 | 2HCl |
| 67 | —NHCOCH₂N(piperazinyl)N—CH₂CH=CH₂ | H | 5-CH₃, 7-CH₃, 8-OH | 3 | Colorless powdery crystals (Acetone) | 192–194 | 2HCl |
| 68 | —NHCOCH₂N(piperazinyl)N—CH₃ | H | 5-CH₃, 7-CH₃, 8-OH | 3 | Colorless powdery crystals (Ethanol) | 247 (dec.) | 2HCl |
| 69 | —NHCOCH₂N(piperazinyl)—C₆H₄—OCH₃ (3-OCH₃) | H | 5-CH₃, 8-OH | 2 | Colorless powdery crystals (Ethanol) | 192–194 | HCl |
| 70 | —NHCOCH₂N(piperazinyl)—C₆H₄—OCH₃ | H | 5-CH₃, 7-CH(CH₃)CH=CH₂, 8-OH | 3 | Colorless powdery crystals (Ethanol) | 169–170.5 | HCl |
| 71 | —NHCOCH₂N(piperazinyl)N—CH₃ | H | 5-CH₃, 7-CH(CH₃)CH=CH₂, 8-OH | 3 | Colorless powdery crystals (Ethanol) | 221 (dec.) | 2HCl |

EXAMPLE 72

3.26 Grams of lithium aluminum hydride was suspended in 30 ml of diisopropyl ether and to the suspension was gradually added dropwise a diisopropyl ether solution containing 2.81 g of 9-(N-acetyl-N-methylamino)-8-hydroxy-5-methyl-7-(1-methyl-2-propenyl)-1,2,3,4,4a,9a-hexahydrofluorene in 30 ml of diisopropyl ether with stirring at room temperature. After completion of the addition, the mixture was refluxed with heating for 4.5 hours. After the reaction mixture was left to stand for cooling, thereto were added ice water and then ethyl acetate and the mixture was filtered using Celite. The filtrate was extracted with water-ethyl acetate and the organic layer was dried with magnesium sulfate. The solvent was removed by concentration and the residue was dissolved in ethanol. Thereto was added a saturated hydrochloric acid gas-ethanol solution and then the solution was rendered acidic and again concentrated. The resulting residue was recrystallized from ethanol to obtain 0.93 g of 9-(N-methyl-N-ethyl)amino-8-hydroxy-7-(1-methyl-2-propenyl)-5-methyl-1,2,3,4,4a,9a-hexahydrofluorene hydrochloride.

Melting point: 134°–136° C.

Colorless powdery crystal.

The compounds of said Examples 22, 25-28, 35-38, 40-44, 47-50 and 52 and Examples 119-131, 145B, 145C., 176, 177 and 178 given hereinafter were prepared in the same manner as in Example 72 using suitable starting materials.

EXAMPLES 73-82

The following compounds were prepared in the same manner as in Examples 20, 21, 54 and 72 using suitable starting materials. The results are shown in Table 9.

(0.77H, dd, J=2.5 Hz, 16.72 Hz), 3.97 (0.33H, dd, J=2.5 Hz, 16.6 Hz), 4.26 (0.77H, dd, J=2.5 Hz, 16.7 Hz), 4.35 (0.33H, dd, J=2.5 Hz, 16.7 Hz), 4.93 (1H, d, J=6.7 Hz), 6.80 (1H, s).

TABLE 9

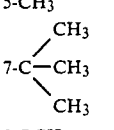

| Example No. | $R^1$ | $R^2$ | $R^3$ | n | Crystal form (Recrystallization solvent) | Melting point (°C.) | Salt form |
|---|---|---|---|---|---|---|---|
| 73 | —NHCH₃ | H | 5-CH₃<br>7-Br<br>8-OH | 3 | Colorless prism-like crystal (Ethanol) | 132-134 | — |
| 74 | —NHCH₃ | H | 5-Cl<br>7-CH₃<br>8-OH | 3 | Colorless needle-like crystal (Ethanol) | 134-135.5 | — |
| 75 | —N(CH₃)₂ | H | 5-CH₃<br>7-C(CH₃)₃<br>8-OCH₃ | 3 | Colorless powdery crystal (Acetonitrile) | 197-198 | HCl |
| 76 | —NHCH₂C≡CH | H | 5-CH₃<br>7-CH₃<br>8-OH | 3 | Colorless oily substance | — | HCl |
| 77 | —NHCH₃ | H | 5-CH₃<br>7-CH(CH₃)(C₂H₅)<br>8-OH | 3 | Colorless flaky crystals (Ethanol) | 188-189 | HCl |
| 78 | —N(CH₃)₂ | H | 5-CH₃<br>7-Br<br>8-OCH₃ | 3 | Colorless prism-like crystals (Ethanol) | 216-219 (dec.) | HCl |
| 79 | —NHCH₃ | H | 5-CH₃<br>7-CH(C₆H₅)(CH₂CH₃)<br>8-OH | 3 | Colorless powdery crystals (n-Hexone-diethyl ether) | 135-138 (dec.) | HCl |
| 80 | —N(CH₃)₂ | H | 5-CH₃<br>7-CH₃<br>8-OH | 3 | Colorless needle-like crystal (Ethanol) | 80-82 | — |
| 81 | —N(CH₃)₂ | H | 5-CH₃<br>7-CH₃<br>8-OH | 3 | Colorless powdery crystal (Acetone) | 184-186 | HCl |
| 82 | —NHCH₂CH₃ | H | 5-CH₃<br>7-CH(CH₃)(CH=CH₂)<br>8-OH | 3 | Colorless needle-like crystal (Ethanol) | 169-171 (dec.) | HCl |

NMR data of the compound (a mixture of stereoisomers A:B=2:1) of Example 76 in Table 9 are as follows:
¹H-NMR (CDCl₃) δ: 1.07-1.94 (m), 2.13-2.61 (m), 2.24 (6H, s), 3.06 (0.33H, brs), 3.17 (0.77H, m), 3.87

EXAMPLES 83-92

The following compounds were prepared in the same manner as in Examples 56 and 57 using suitable starting materials. The results are shown in Table 10.

TABLE 10

[Structure: fluorene-type tricyclic with R¹, R² at 9-position, R² at 9a-position, (R³)ₙ on aromatic ring]

| Example No. | R¹ | R² | R³ | n | Crystal form (Recrystallization solvent) | Melting point (°C.) | Salt form |
|---|---|---|---|---|---|---|---|
| 83 | −N(CH₃)(COCH₂CH₃) | H | 5-CH₃, 7-CH(CH₃)CH=CH₂, 8-OH | 3 | Colorless powdery crystals (Ethanol) | 163–165 | — |
| 84 | −N(CH₃)(COCH₃) | H | 5-CH₃, 7-CH₂CH=CH₂, 8-OH | 3 | Colorless powdery crystals (Ethanol) | 144–146 | — |
| 85 | −N(CH₃)(COCH₃) | H | 5-CH₃, 7-C(CH₃)₃, 8-OH | 3 | Colorless powdery crystals (Ethanol-n-hexane) | 200–201 | — |
| 86 | −N(CH₃)(COCH₃) | H | 5-CH₃, 7-Br, 8-OH | 3 | Colorless prism-like crystals (Ethanol) | 211–213 (dec.) | — |
| 87 | −N(CH₃)(COH) | H | 5-CH₃, 7-CH₃, 8-OH | 3 | Colorless prism-like crystals (Ethanol) | 185–188 | — |
| 88 | −N(CH₃)(COH) | H | 5-CH₃, 7-CH₃, 8-OCH₃ | 3 | Light yellow oily substance | — | — |
| 89 | −N(CH₃)(COCH₃) | H | 5-CH₃, 7-CH₃, 8-OH | 3 | Colorless prism-like crystals (Ethanol) | 200–202 | — |
| 90 | −N(CH₃)(COCH₃) | H | 5-CH₃, 7-CH(CH₃)CH=CH₂, 8-OCH₃ | 3 | Light yellow oily substance | — | — |
| 91 | −N(CH₃)(COCH₃) | H | 5-CH₃, 7-CH(C₆H₅)CH=CH₂, 8-OH | 3 | Colorless powdery crystals (n-Hexane-diethyl ether) | 153–155 | — |
| 92 | −N(CH₃)(COCH₃) | H | 5-CH₃, 7-CH(CH₃)CH₂CH₃, 8-OH | 3 | Colorless powdery crystal (Ethanol) | 171–172 | — |

NMR data of the compound (mixture of stereoisomers) of Example 88 in Table 10 are as follows:

¹H-NMR (CDCl₃) δ: 1.00–3.17 (m), 2.09 (s), 2.15 (s), 2.17 (3H, s), 2.57 (1.5H, s), 2.67 (1.5H, s), 3.60 (1.5H, s), 3.61 (1.5H, s), 4.91 (0.5H, d, J=1.5 Hz), 5.00 (0.5H, d, J=1.5 Hz), 6.85 (1H, s), 8.13 (0.5H, s), 8.22 (0.5H, s).

NMR data of the compound (mixture of stereoisomers) of Example 90 in Table 10 are as follows:

¹H-NMR (CDCl₃) δ:

1.12–1.80 (10H, m), 1.98–2.20 (1H, m),
2.19 (3H, s),
2.28 (s)  }  totally 3H,
2.34 (s)
2.61 (s)  }  totally 3H,
2.66 (s)
2.70–2.97 (1H, m), 2.98–3.19 (1H, m),
3.67 (s)
3.68 (s)  }  totally 3H,
3.71 (s)
3.80–3.97 (1H, m),
4.94–5.16 (2H, m),
5.44–5.57 (m)
5.93–6.18 (m)  }  totally 2H,
6.21–6.37 (m)
6.90 (s)  }  totally 1H.
6.93 (s)

EXAMPLE 93

50 Milliliters of acetic acid and 0.20 g of platinum oxide were added to 2.00 g of 8-hydroxy-5-methyl-9-methylamino-7-(1-methyl-2-propenyl)-1,2,3,4,4a,9a-hexahydrofluorene and catalytic reduction was effected at room temperature under a hydrogen pressure of 4 atm. After completion of the reaction, the catalyst was removed by filtration and the filtrate was concentrated and then neutralized and extracted with saturated aqueous sodium bicarbonate solution-chloroform. The organic layer was dried with magnesium sulfate and then the solvent was distilled off. The resulting residue was purified by a silica gel column chromatography (eluent: ethyl acetate:n-hexane=1:10) and then converted to a hydrochloride with hydrochloric acid-ethanol, which was recrystallized from ethanol to obtain 0.88 g of 8-hydroxy-5-methyl-9-methylamino-7-(1-methylpropyl)-1,2,3,4,4a,9a-hexahydrofluorene hydrochloride.

Melting point: 188°–190° C.

Colorless flaky crystal.

The compounds of said Examples 11–14 and 79 and Examples 120, 126, 127, 148, 149 and 177 given hereinafter were prepared in the same manner as in Example 93 using suitable starting materials.

EXAMPLES 94–117

The following compounds were prepared in the same manner as in Examples 20 and 21 using suitable starting materials. The results are shown in Table 11.

TABLE 11

| Example No. | R¹ | R² | R³ | n |
|---|---|---|---|---|
| 94 | —NHCH₂CH=CH₂ | H | 5-CH₃<br>7-CH(CH₃)CH=CH₂<br>8-OH | 3 |
| 95 |  | H | 5-CH₃<br>7-CH(CH₃)CH=CH₂<br>8-OH | 3 |
| 96* | 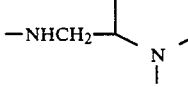 | H | 5-CH₃<br>7-CH(CH₃)CH=CH₂<br>8-OH | 3 |
| 97* | 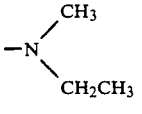 | H | 5-CH₃<br>7-CH(CH₃)CH=CH₂<br>8-OH | 3 |
| 98 | —NHCH₂CH=CH₂ | H | 5-CH₃<br>7-CH₂CH=CH₂<br>8-OH | 3 |
| 99 |  | H | 5-CH₃<br>7-CH₂CH=CH₂<br>8-OH | 3 |

TABLE 11-continued

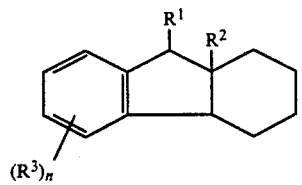

| Example No. | R¹ | R² | R³ | n |
|---|---|---|---|---|
| 100 | −NHCH₂−[2-(1-ethyl)pyrrolidinyl] | H | 5-CH₃<br>7-CH₂CH=CH₂<br>8-OH | 3 |
| 101 | −N(CH₃)₂ | H | 5-CH₃<br>7-CH₂CH=CH₂<br>8-OH | 3 |
| 102 | −NHCH₂CH=CH₂ | H | 5-CH₃<br>7-CH₂CH=CH₂<br>8-OCH₃ | 3 |
| 103 | −NHCH₂CH=CH₂ | H | 5-CH₃<br>7-C(CH₃)₃<br>8-OH | 3 |
| 104 | −NHCH₂−[4-(1-benzyl)piperidinyl] | H | 5-CH₃<br>7-C(CH₃)₃<br>8-OH | 3 |
| 105 | −NHCH₂−[2-(1-ethyl)pyrrolidinyl] | H | 5-CH₃<br>7-C(CH₃)₃<br>8-OH | 3 |
| 106* | −NHCH₃ | H | 5-CH₃<br>7-NO₂<br>8-OH | 3 |
| 107 | −NHCH₃ | H | 5-CH₃<br>7-N(CH₃)₂<br>8-OH | 3 |
| 108 | −NHCH₃ | H | 5-CH₃<br>7-NHCOCH₃<br>8-OH | 3 |
| 109 | −NHCH₃ | H | 5-CH₃<br>7-SCH₃<br>8-OH | 3 |
| 110 | −NHCH₃ | H | 5-CH₃<br>7-CH₂SCH₃<br>8-OH | 3 |
| 111 | −NHCH₃ | H | 5-CH₃<br>7-CN<br>8-OH | 3 |
| 112 | −NHCH₃ | H | 5-CH₃<br>7-CO₂H<br>8-OH | 3 |
| 113 | −NHCH₃ | H | 5-CH₃<br>7-CHO<br>8-OH | 3 |
| 114 | −NHCH₃ | H | 5-F | 3 |

TABLE 11-continued

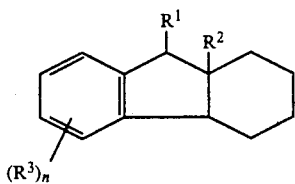

| Example No. | R¹ | R² | R³ | n |
|---|---|---|---|---|
| | | | 7-F | |
| | | | 8-OH | |
| 115 | —NHCH₃ | H | 5-F | 3 |
| | | | $\quad$ CH₃ | |
| | | | $\quad$ | | |
| | | | 7-CHCH=CH₂ | |
| | | | 8-OH | |
| 116 | —NHCH₃ | H | 5-CH₃ | 3 |
| | | | 7-OCH₃ | |
| | | | 8-OH | |
| 117 | —NHCH₃ | H | 5-CH₃ | 3 |
| | | | 7-NH₂ | |
| | | | 8-OH | |

*Example 96:
Isomer A: ¹H-NMR (CDCl₃) δ:
1.08 (3H, t, J=7.2Hz), 1.32 (3H, t, J=7.4Hz), 2.19 (3H, s), 0.95-2.30 (13H, m), 2.38 (0.5H, m), 2.50-2.85 (6H, m), 3.14 (2H, m), 3.35 (0.5H, m), 3.81 (1H, m), 4.15 (1H, m), 5.03 (1H, m), 6.10 (1H, m), 6.67 (1H, s).
Isomer B: ¹H-NMR (CDCl₃) δ:
1.12 (3H, t, J=7.2Hz), 1.32 (3H, t, J=6.9Hz), 2.24 (3H, s), 1.0-2.4 (14H, m), 2.54 (4H, m), 2.86 (2H, m), 3.14 (2H, m), 3.81 (1H, m), 4.16 (1H, d, J=5.6Hz), 5.02 (2H, m), 6.09 (1H, m), 6.68 (1H, s).
*Example 97:
Hydrochloride
Colorless powdery substance (from ethonol-n-hexane)
Melting point: 134-136° C.
*Example 106:
Isomer A Hydrochloride
Redish needle-like crystals
Melting point: 179-181° C.
¹H-NMR (CDCl₃) δ:
0.93-1.13 (m, 0.5H), 1.20-1.72 (m, 6.5H), 2.02-2.37 [1m, 6H, contains 2.23 (5.3H)], 2.91 (d, t, J=6Hz, 12Hz, 1H), 3.38 (s, 3H), 5.37 (dd, J=6Hz, 6Hz, 1H), 7.97 (1H, s), 8.54 (br, s, 1H).
Isomer Hydrochloride
Redish needle-like crystals
Melting point: 132-136° C.
¹H-NMR (CDCl₃) δ:
0.82-1.00 (m, 0.5H), 1.20-1.83 (m, 5.5H), 1.93-2.33 [m, 6H, contains 2.22 (s, 3H)], 2.42 (d, J=7.5Hz, 1H), 3.01 (d, t, J=6Hz, 12Hz, 1H), 3.10 (s, 3H), 5.27 (dd, J=7.5Hz, 7.5Hz, 1H), 7.34 (brs, H), 7.85 (s, 1H).

The following compound was prepared in the same manner as in Examples 56 and 57 using suitable starting materials. The result is shown in Table 12.

TABLE 12

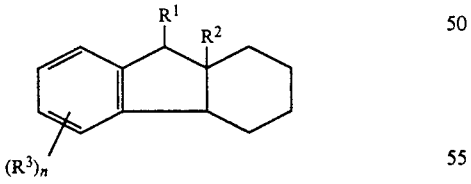

| Example No. | R¹ | R² | R³ | n |
|---|---|---|---|---|
| 118* | CH₂CH₃ | H | 5-CH₃ | 3 |
| | —N | | $\quad$ CH₃ | |
| | $\quad$ COCH₃ | | $\quad$ | | |
| | | | 7-CHCH=CH₂ | |
| | | | 8-OH | |

*Example 118
Colorless granular crystals (from ethanol) Melting point: 170-172° C.

EXAMPLES 119-157

The following compounds were prepared in the same manner as in Example 57 using suitable starting materials. The results are shown in Table 13.

TABLE 13

| Example No. | R³ | n | R¹ | R² | Bonding between 4a and 9a-positions | Crystal form (Recrystallization solvent) | Melting point (°C.) (Salt) |
|---|---|---|---|---|---|---|---|
| 119 | 5-CH₃<br>7-NHCOCH₃<br>8-OH | 3 | —NHCH₃ | H | Single bond | Light brown powdery crystal (Ethyl acetate-n-hexane) | 133-135 (—) |
| 120 | 5-OCH₃<br>7-CH(CH₃)(C₂H₅)<br>8-OH | 3 | —NHCH₃ | H | Single bond | White powdery substance (Acetonitrile) | 179-183 (dec.) (HCl) |
| 121 | 5-OCH₃<br>7-CH(CH₃)(CH=CH₂)<br>8-OCH₃ | 3 | —N(CH₃)₂ | H | Single bond | White powdery substance (Ethanol-diethyl ether) | 179-182 (dec.) (HCl) |
| 122 | 5-CH₃<br>7-(cyclohexenyl)<br>8-OCH₃ | 3 | —N(CH₃)₂ | H | Single bond | White powdery crystal (Ethanol-diethyl ether) | 190-193 (dec.) (HCl) |
| 123 | 5-OCH₃<br>7-CH(CH₃)(CH=CH₂)<br>8-OH | 3 | —NHCH₃ | H | Single bond | White powdery crystal (Ethanol) | 183-185 (dec.) (HCl) |
| 124 | 5-CH₃<br>7-C(CH₃)₃<br>8-OH | 3 | —NHCH₃ | CH₃ | Single bond | White powdery crystal (Ethanol) | 237-239 (dec.) (HCl) |
| 125 | 5-CH₃<br>7-CH(CH₃)(CH=CH₂)<br>8-OH | 3 | —NHCH₃ | CH₃ | Single bond | White powdery crystal (Diisopropyl ether) | 155-160 (dec.) (HCl) |
| 126 | 5-CH₃<br>7-(cyclohexyl)<br>8-OCH₃ | 3 | —N(CH₃)₂ | H | Single bond | Colorless granular crystal (Acetonitrile) | 218-223 (dec.) (HCl) |
| 127 | 5-CH₃<br>7-(cyclohexyl)<br>8-OH | 3 | —NHCH₃ | H | Single bond | Colorless plate-like crystals (Ethanol) | 108-109 (—) |
| 128 | 5-CH₃<br>7-(cyclohexenyl)<br>8-OH | 3 | —NHCH₃ | H | Single bond | Colorless needle-like crystal (Ethanol) | 193-197 (dec.) (HCl) |

TABLE 13-continued

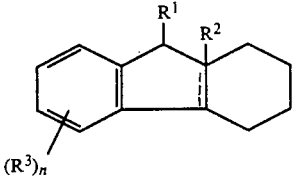

| No. | (R³)ₙ | n | R¹ | R² | Bond | Appearance (Solvent) | m.p. (°C) |
|---|---|---|---|---|---|---|---|
| 129 | 5,7-diCH₃<br>8-OH | 3 | —NHCH₂CH₂CH₃ | CH₃ | Single bond | Colorless prism-like crystals (Ethanol) | 196–198 (dec.) (HCl) |
| 130 | 5-F<br>7-CH(CH₃)CH=CH₂<br>8-OH | 3 | —NHCH₃ | H | Single bond | Colorless granular crystal (Ethanol) | 190–193 (dec.) (HCl) |
| 131 | 5-CH₃<br>8-OCH₃ | 2 | —N(CH₃)₂ | H | Single bond | White powdery crystal (Acetonitrile) | 180–181 (HCl) |
| 132 | 5,7-diCH₃<br>8-OCH₃ | 3 | —(CH₂)₂—NH₂ | — | Double bond | Light green powdery crystal (Ethanol)* | 227–229 (dec.) (HCl) |
| 133 | 5,7-diCH₃<br>8-OCH₃ | " | —(CH₂)₂—NHCH₃ | — | Double bond | Light green powdery crystal (Ethanol)* | 218–220 (dec.) (HCl) |
| 134 | 5,7-diCH₃<br>8-OCH₃ | " | —(CH₂)₂—N(CH₃)₂ | — | Double bond | Light yellow powdery crystal (Diethyl-ether-diisopropyl ether)* | 193–195 (dec.) (HCl) |
| 135 | 5,7-diCH₃<br>8-OCH₃ | 3 | —(CH₂)₂—N(piperazinyl)-C₆H₄-3-CH₃ 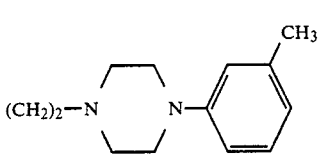 | — | Double bond | White powdery crystal (Ethanol-diisopropyl ether)* | 164–166 (dec.) (2HCl) |
| 136 | 5,7-diCH₃<br>8-OCH₃ | " | —(CH₂)₂—N(piperazinyl)-C₆H₄-3-OCH₃ 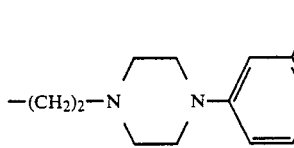 | — | Double bond | White powdery crystal (Ethanol-diisopropyl ether)* | 149–152 (dec.) (2HCl) |
| 137 | 5,7-diCH₃<br>8-OCH₃ | " | —(CH₂)₂—N(piperazinyl)-C₆H₄-Cl 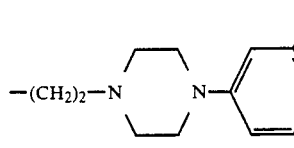 | — | Double bond | White powdery crystal (Ethanol-diisopropyl ether)* | 155–158 (dec.) (2HCl) |
| 138 | 5,7-diCH₃<br>8-OCH₃ | " | —(CH₂)₂—N(piperazinyl)-N—CH₃ 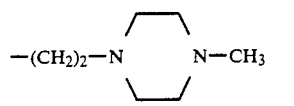 | — | Double bond | Light yellow powdery crystal (Ethanol)* | 202–204 (dec.) (2HCl) |
| 139 | 5,7-diCH₃<br>8-OCH₃ | " | —(CH₂)₂NHCH₂COOH | — | Double bond | White powdery crystal (Ethanol)* | 184 (dec.) (—) |
| 140 | 5,7-diCH₃<br>8-OCH₃ | 3 | —(CH₂)₂NHCH₂CONH₂ | — | Double bond | Light brown powdery crystal (Ethanol-diisopropyl ether)* | 212 (dec.) (HCl) |
| 141 | 5,7-diCH₃<br>8-OCH₃ | " | —(CH₂)₂NH(CH₂)₂OH | — | Double bond | Light yellow powdery crystal (Ethanol-diisopropyl ether)* | 178–180 (dec.) (HCl) |

TABLE 13-continued

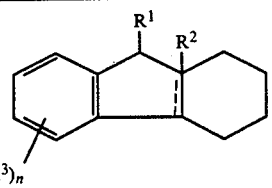

| No. | (R³)ₙ | n | R¹ (or substituent) | R² | Bond | Crystal form (solvent) | mp (°C) (salt) |
|---|---|---|---|---|---|---|---|
| 142 | 5,7-diCH₃<br>8-OCH₃ | " | −(CH₂)₂−N⟨ ⟩N(CH₃)₂ (piperazine) | — | Double bond | White powdery crystal (Ethanol)* | 262 (dec.) (2HCl) |
| 143 | 5,7-diCH₃<br>8-OCH₃ | " | −(CH₂)₂N⟨ ⟩ (pyrrolidine) | — | Double bond | White powdery crystal (Ethanol-diisopropyl ether)* | 194−196 (dec.) (HCl) |
| 144 | 5,7-diCH₃<br>8-OCH₃ | 3 | −(CH₂)₂NHCH₂-(4-pyridyl) | — | Double bond | White powdery crystal (Ethanol-diisopropyl ether)* | 195 (dec.) (2HCl) |
| 145 | 5-CH₃<br>8-OCH₃ | 2 | −CH₂NHCH₃ | H | Single bond | Colorless needle-like crystal (Ethanol) | 259−260 (HCl) |
| 145A | 5,7-diCH₃<br>8-OCH₃ | 3 | −CH₂NHCH₃ | H | Single bond | Colorless prism-like crystals (Ethanol-diethyl ether) | 245−246 (—) |
| 145B | 5-CH₃<br>7-NH₂<br>8-OH | 3 | −NHCH₃ | H | Single bond | Pale brown powdery substance (Ethanol-diethyl ether) | 197−200 (dec.) (HCl) |
| 146 | 5-CH₃<br>7-CH(CH₃)CH=CH₂<br>8-OH | 3 | −N(CH₃)COCH₂N(CH₃)₂ | H | Single bond | White powdery crystal (Ethanol-diethyl ether) | 244−247 (dec.) (HCl) |
| 147 | 5-CH₃<br>7-NHCOCH₃<br>8-OH | 3 | −N(CH₃)COCH₃ | H | Single bond | White powdery crystal (Ethanol) | 229−231 (dec.) (—) |
| 148 | 5-CH₃<br>7-cyclohexyl<br>8-OH | 3 | −N(CH₃)COCH₃ | H | Single bond | White powdery crystal (Ethanol) | 226−228 (—) |
| 149 | 5-F<br>7-CH(CH₃)C₂H₅<br>8-OH | 3 | −N(CH₃)COCH₃ | H | Single bond | Colorless prism-like crystal (Ethanol) | 179−182 (—) |
| 150 | 5-OCH₃<br>7-CH(CH₃)CH=CH₂<br>8-OH | 3 | −N(CH₃)COCH₃ | H | Single bond | Colorless prism-like crystal (Ethanol) | 194−196 |
| 151 | 5-CH₃<br>7-cyclohexenyl<br>8-OH | 3 | −N(CH₃)COCH₃ | H | Single bond | White powdery crystal (Ethanol-chloroform) | 240−244 (dec.) (—) |

TABLE 13-continued

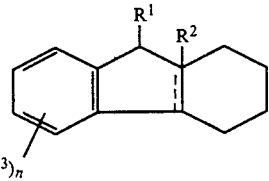

| | | | | | | | |
|---|---|---|---|---|---|---|---|
| 152 | 5-CH₃<br>7-C(CH₃)₃<br>8-OH | 3 | −N(COCH₃)(CH₃) | CH₃ | Single bond | White powdery crystal (Ethanol) | 222–224 (dec.) (—) |
| 153 | 5-CH₃<br>7-CH(CH₃)(CH=CH₂)<br>8-OH | 3 | −N(CH₃)(COCH₃) | CH₃ | Single bond | White powdery crystal (Ethanol) | 183–184 (—) |
| 154 | 5-CH₃<br>8-OH | 2 | −N(CH₃)(COCH₃) | H | Single bond | Colorless needle-like crystals (Ethanol) | 223–226 (—) |
| 155 | 5-CH₃<br>7-CH(CH₃)(CH=CH₂)<br>8-OH | 3 | −N(CH₃)(COCH₃) | H | Single bond | Colorless powdery crystals (Ethanol) | 143–145 (—) |
| 156 | 5-F<br>7-CH(CH₃)(CH=CH₂)<br>8-OH | 3 | −N(CH₃)(COCH₃) | H | Single bond | Colorless prism-like crystal (Ethanol) | 150–152 (—) |
| 157 | 5-OCH₃<br>7-CH(CH₃)(CH₂CH₃)<br>8-OH | 3 | −N(CH₃)(COCH₃) | H | Single bond | Colorless prism-like crystals (Ethanol) | 211–214 (dec.) (—) |

Example 132 ¹H-NMR (250 MHz) CDCl₃ δ:
1.6–1.9 (4H, m), 2.23 (3H, s), 2.26 (3H, s), 2.1–2.6 (6H, m), 2.69 (2H, m), 3.50 (1H, m), 3.79 (3H, s), 6.82 (1H, s), 8.09 (3H, br).

Example 133 ¹H-NMR (250 MHz) CDCl₃ δ:
1.6–1.8 (4H, m), 2.23 (3H, s), 2.41 (3H, s), 2.2–2.7 (8H, m), 3.51 (1H, m), 3.78 (3H, s), 6.81 (1H, s), 9.2 (1H, br), 9.4 (1H, br).

Example 134 ¹H-NMR (250 MHz) CDCl₃ δ:
1.80 (4H, m), 2.27 (3H, s), 2.59 (3H, s), 2.64 (3H, d), 2.71 (3H, d), 2.10–3.00 (4H, m), 3.59 (1H, m), 3.81 (3H, s), 6.87 (1H, s), 12.40 (1H, br).

Example 135 ¹H-NMR (250 MHz) CDCl₃ δ:
1.65–1.75 (4H, m), 2.25 (3H, s), 2.41 (3H, s), 2.44 (3H, s), 2.2–2.7 (7H, m), 2.92 (1H, m), 3.37 (1H, m), 3.58 (4H, m), 3.78 (3H, s), 4.0–4.3 (2H, m), 4.70 (2H, m), 6.85 (1H, s), 7.28 (1H, m), 7.40 (1H, t, J=7.5), 7.67 (2H, m).

Example 136 ¹H-NMR (250 MHz) CDCl₃ δ:
1.65–1.75 (4H, m), 2.25 (3H, s), 2.44 (3H, s), 2.20–2.70 (7H, m), 2.92 (1H, m), 3.38 (1H, m), 3.59 (4H, m), 3.78 (3H, s), 3.85 (3H, s), 4.06 (2H, m), 4.71 (2H, m), 6.85 (1H, s), 6.99 (1H, m), 7.40 (2H, m), 7.50 (1H, m).

Example 137 ¹H-NMR (250 MHz) CDCl₃ δ:
1.6–1.9 (4H, m), 2.25 (3H, s), 2.44 (3H, s), 2.2–2.8 (7H, m), 2.91 (1H, m), 3.78 (3H, s), 3.2–4.1 (7H, m), 4.59 (2H, m), 6.85 (1H, s), 7.43 (2H, m), 7.67 (1H, m), 7.81 (1H, m).

Example 138 ¹H-NMR (250 MHz) CDCl₃ δ:
1.6–1.9 (4H, m), 2.24 (3H, s), 2.43 (3H, s), 2.88 (3H, s), 2.1–2.8 (8H, m), 3.76 (3H, s), 3.25–3.9 (7H, m), 4.06 (2H, s), 6.84 (1H, s).

Example 139 ¹H-NMR (250 MHz) CDCl₃-DMSO-d₆:
1.5–1.8 (6H, m), 2.21 (3H, s), 2.40 (3H, s), 2.1–2.4 (6H, m), 2.4–2.9 (6H, m), 3.49 (1H, s), 3.76 (3H, s), 6.78 (1H, s).

Example 140 ¹H-NMR (250 MHz) DMSO-d₆:
1.6–1.8 (4H, m), 2.20 (3H, s), 2.38 (3H, s), 2.1–2.6 (6H, m), 2.62 (2H, m), 3.59 (3H, m), 3.74 (3H, s), 6.82 (1H, s), 7.50 (1H, br), 7.79 (1H, br), 8.78 (2H, br).

Example 141 ¹H-NMR (250 MHz) CDCl₃ δ:
2.22 (3H, s), 2.42 (3H, s), 1.6–3.2 (14H, m), 3.52 (1H, m), 3.78 (3H, s), 3.87 (2H, m), 4.60 (1H, br), 6.81 (1H, s), 8.7 (1H, br), 9.0 (1H, br).

Example 142 ¹H-NMR (250 MHz) DHSO-d₆ δ:
2.20 (3H, s), 2.39 (3H, s), 2.70 (6H, s), 3.76 (3H, s), 6.83 (1H, s)
(Free - ¹H-NMR (250 MHz) CDCl₃ δ:

TABLE 13-continued

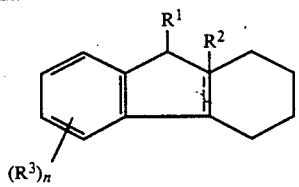

| | |
|---|---|
| | 2.28 (3H, s), 2.29 (3H, s), 2.69 (6H, s), 2.89 (2H, m), 3.50 (1H, m), 3.81 (3H, s), 3.8 (1H, m), 6.8 (1H, s). |
| Example 143 | $^1$H-NMR (250 MHz) CDCl$_3$ δ: |
| | 1.65–2.4 (10H, m), 2.24 (3H, s), 2.42 (3H, s), 2.4–2.7 (8H, m), 3.53 (1H, m), 3.77 (3H, s), 3.5–3.8 (2H, m), 6.82 (1H, s). |
| Example 144 | $^1$H-NMR (250 MHz) CDCl$_3$-DMSO-d$_6$: |
| | 1.6–1.8 (4H, m), 2.23 (3H, s), 2.41 (3H, s), 2.2–2.8 (8H, m), 3.54 (1H, m), 3.78 (3H, s), 4.22 (2H, m), 6.81 (1H, s), 8.38 (2H, br), 8.8 (2H, br), 10.5 (1H, br), 10.98 (1H, br). |

EXAMPLE 158

A methanol solution containing 1.0 g of 5,7-dimethyl-8-methoxy-9-formylmethyl-1,2,3,4-tetrahydro-9H-fluorene in 10 ml of methanol was added dropwise to a methanol solution containing 3.0 g of dimethylamine hydrochloride and 5.2 ml of triethylamine in 30 ml of methanol at 0° C. After stirring at the same temperature for 3 hours, 100 mg of sodium borohydride was added, followed by further stirring at the same temperature for 2 hours. The reaction mixture was diluted with chloroform, washed successively with water and saturated aqueous sodium chloride solution and then dried with magnesium sulfate. The solvent was distilled off under reduced pressure and the residue was purified by a silica gel column chromatography (eluent: methanol:chloroform=1:1) to obtain 700 mg of 5,7-dimethyl-8-methoxy-9-(2-dimethylaminoethyl)-1,2,3,4-tetrahydro-9H-fluorene. This was dissolved in ethanol and to the solution were added ethanol·hydrochloric acid. The solvent was distilled off and the residue was recrystallized from diethyl ether-diisopropyl ether to obtain 220 mg of 5,7-dimethyl-8-methoxy-9-(2-dimethylaminoethyl)-1,2,3,4-tetrahydro-9H-fluorene hydrochloride.

Melting point: 193°–195° C. (decomposed).
Light yellow powdery crystal.
$^1$H-NMR CDCl$_3$) δ: 1.80 (4H, m), 2.27 (3H, s), 2.59 (3H, s), 2.64 (3H, d), 2.71 (3H, d), 2.10–3.00 (4H, m), 3.59 (1H, m), 3.81 (3H, s), 6.87 (1H, s), 12.40 (1H, br).

EXAMPLE 159

1.1 Milliliter of N-methylpiperazine was added to methanol solution containing 900 mg of 5,7-dimethyl-8-methoxy-9-formylmethyl-1,2,3,4-tetrahydro-9H-fluorene in 30 ml of methanol at 0° C. After stirring at the same temperature for 2 hours, 50 mg of sodium borohydride was added, followed by stirring at the same temperature for 1 hour. The solvent was distilled off and the residue was diluted with chloroform, washed with water and then dried with magnesium sulfate. The solvent was distilled off and the residue was purified by a silica gel column chromatography (eluent: methanol:chloroform=3:17) and then converted to a hydrochloride with saturated hydrochloric acid-ethanol solution. The product was recrystallized from ethanol to obtain 600 mg of 5,7-dimethyl-8-methoxy-9-[2-(4-methyl-1-piperazinyl)ethyl]-1,2,3,4-tetrahydro-9H-fluorene dihydrochloride.

Melting point: 202°–204° C. (decomposed).
White powdery crystal.

$^1$H-NMR (CDCl$_3$) δ: 1.6–1.9 (4H, m), 2.24 (3H, s), 2.43 (3H, s), 2.88 (3H, s), 2.1–2.8 (8H, m), 3.76 (3H, s), 3.25–3.9 (7H, m), 4.06 (2H, s), 6.84 (1H, s).

The compounds of said Examples 133, 135–137 and 139–145 were prepared in the same manner as in Examples 158 and 159 using suitable starting materials.

EXAMPLE 160

500 Milligrams of hydroxylamine hydrochloride was added to an ethanol-chloroform (5:1) solution containing 910 mg of 5,7-dimethyl-8-methoxy-9-formylmethyl-1,2,3,4-tetrahydro-9H-fluorene in 18 ml of ethanol-chloroform and the mixture was refluxed with heating for 2 hours. The reaction mixture was diluted with chloroform and then washed with saturated aqueous sodium chloride solution and subsequently the solvent was distilled off. The residue was purified by a silica gel column chromatography (eluent: ethyl acetate:n-hexane=1:10) to obtain 670 mg of 5,7-dimethyl-8-methoxy-9-hydroxyiminomethyl-1,2,3,4-tetrahydro-9H-fluorene.

Light yellow oily substance (A 1:1 mixture of syn- and anti-isomers).

$^1$H-NMR (CDCl$_3$) δ: 1.6–1.8 (4H, m), 2.25 (3H, s), 2.42 (1.5H, s), 2.43 (1.5H, s), 2.1–2.3 (6H, m), 3.50 (1H, m), 3.77 (1.5H, s), 3.78 (1.5H, s), 5.99 (0.5H, t, J=5.0 Hz), 6.81 (1.5H, m).

EXAMPLE 161

70 Milligrams of platinum oxide was added to an acetic acid solution containing 670 mg of 5,7-dimethyl-8-methoxy-9-hydroxyiminomethyl-1,2,3,4-tetrahydro-9H-fluorene in 50 ml of acetic acid and thereto was added hydrogen at room temperature under 4 atm. After the catalyst was removed by Celite filtration, the solvent was distilled off and residue was diluted with chloroform, washed with water and saturated aqueous sodium chloride solution in this order and then dried with magnesium sulfate. Then, solvent was distilled off and the residue was purified by a silica gel column chromatography (eluent: methanol:chloroform=3:17) and then converted to a hydrochloride with ethanol-hydrochloric acid and this was recrystallized from ethanol to obtain 110 mg of 5,7-dimethyl-8-methoxy-9-(2-aminoethyl)-1,2,3,4-tetrahydro-9H-fluorene hydrochloride.

Melting point: 227°–229° C. (decomposed).
Light green powdery crystal.
$^1$H-NMR CDCl$_3$) δ: 1.6–1.9 (4H, m), 2.23 (3H, s), 2.26 (3H, s), 2.1–2.6 (6H, m), 2.69 (2H, m), 3.50 (1H, m), 3.79 (3H, s), 6.82 (1H, s), 8.09 (3H, br).

EXAMPLE 162

25.00 Grams of 8-hydroxy-5-methyl-9-methylamino-7-(1-methyl-2-propenyl)-1,2,3,4,4a,9a-hexahydrofluorene was dissolved in 250 ml of chloroform. Under ice-cooling and stirring, to the solution were added 24.4 ml of triethylamine and then 14.95 ml of acetyl chloride, followed by stirring at room temperature for 1 hour. Extraction was carried out with addition of water and the organic layer was concentrated. The resulting residue was dissolved in 250 ml of methanol and thereto was added an aqueous solution containing 1.36 g of sodium bicarbonate in 50 ml of water, followed by refluxing for 2 hours. The reaction mixture was rendered weakly acidic with addition of dilute hydrochloric acid and extracted with chloroform. The organic layer was dried with magnesium sulfate, filtered and concentrated. The resulting residue was purified by a silica gel column chromatography (eluent: chloroform:methanol:ethyl acetate=100:1:5). The component of Rf value 0.29 in the eluate was recrystallized from ethanol to obtain 1.66 g of 8-hydroxy-5-methyl-9-(N-methyl-N-acetylamino)-7-(1-methyl-2-propenyl)-1,2,3,4,4a,9a-hexahydrofluorene (diastereomer B) having a melting point of 143°-145° C. and of colorless powdery crystal and the component of Rf value 0.21 was recrystallized from ethanol to obtain 16.43 g of 8-hydroxy-5-methyl-9-(N-methyl-N-acetylamino)-7-(1-methyl-2-propenyl)-1,2,3,4,4a,9a-hexahydrofluorene (diastereomer A) having a melting point of 166°-168° C. and of colorless granular crystal.

EXAMPLE 163

The following compound was prepared in the same manner as in Example 15 using a suitable starting material.

7-Acetylamino-8-hydroxy-5-methyl-9-methylimino-1,2,3,4,4a,9a-hexahydro-9-fluorene.

Melting point: 220°-228° C. (decomposed).

Yellowish orange needle-like crystal (recrystallized from methanol).

7-Nitro-8-hydroxy-5-methyl-9-methylimino-1,2,3,4,4a,-9a-hexahydro-9-fluorene.

Melting point: 122°-124° C.

Yellowish prism-like crystals (recrystallized from ethanol).

EXAMPLE 164

To 1.5 ml of pyridine were added 1.0 g of 7-(1-methyl-2-propenyl)-8-hydroxy-5-methyl-9-methylamino-1,2,3,4,4a,9a-hexahydrofluorene and 0.7 g of nicotinoyl chloride hydrochloride, followed by stirring at room temperature for 5 hours. The reaction mixture was concentrated and then extracted with chloroform. The chloroform layer was washed with water, dried with sodium sulfate and then concentrated. The residue was purified by a silica gel column chromatography (eluent: ethyl acetate) and then recrystallized from ethyl acetate-n-hexane to obtain 0.7 g of 7-(1-methyl-2-propenyl)-8-hydroxy-5-methyl-9-(N-methyl-N-nicotinoylamino)- 1,2,3,4,4a,9a-hexahydrofluorene having a melting point of 183°-184° C. and of colorless powdery crystal.

EXAMPLE 165

The compound of said Example 146 and the following compound were prepared in the same manner as in Example 63 using suitable starting materials.

7-(1-Methyl-2-propenyl)-8-hydroxy-5-methyl-9-[N-methyl-N-(1-pyrrolidinylacetyl)amino]-1,2,3,4,4a,9a-hexahydrofluorene hydrochloride.

Melting point: 241°-243° C.

Colorless needle-like crystal (recrystallized from ethanol-diisopropyl ether).

EXAMPLE 166

4.0 Grams of 9-amino-8-hydroxy-5,7-dimethyl-1,2,3,4,4a,9a-hexahydrofluorene and 2.5 g of potassium carbonate were added to a mixture of 50 ml of acetone and 20 ml of water and thereto was added dropwise 2.5 ml of γ-chlorobutyryl chloride under ice-cooling and stirring. After stirring for 2 hours, the reaction mixture was concentrated and to the residue was added water and extraction was effected with chloroform. The choroform layer was dried with magnesium sulfate and concentrated. Then, the residue was dissolved in 30 ml of DMF and to the solution was added 2.0 g of sodium hydride (60% oiliness), followed by stirring to generate a gas with generation of heat. Then, the reaction mixture was stirred at room temperature overnight and thereafter concentrated. To the residue was added water and extraction was effected with chloroform. The chloroform layer was dried with magnesium sulfate and concentrated. To the residue was added ethyl acetate and the produced precipitate was collected by filtration and recrystallized from hydrous ethanol to obtain 2.0 g of 8-hydroxy-5,7-dimethyl-9-(2-oxo-1-pyrrolidinyl)-1,2,3,4,4a,9a-hexahydrofluorene having a melting point of 240°-213° C. (decomposed) and of light brown powdery crystal.

EXAMPLE 167

0.34 Gram of aluminum lithium hydride was suspended in 30 ml of THF and to the suspension was gradually added dropwise 1.6 g of 8-hydroxy-5,7-dimethyl 9-(2-oxo-1-pyrrolidinyl)-1,2,3,4,4a,9a-hexahydrofluorene. This suspension was refluxed with heating for 5 hours and then ice-cooled and excess hydride was decomposed with ethyl acetate. To the reaction mixture was added 1.5 ml of saturated aqueous sodium sulfate solution, followed by stirring at room temperature for 1 hour and then filtration to remove the precipitate. The filtrate was concentrated and to the residue was added ethyl acetate and insoluble matter was removed by filtration. The filtrate was again concentrated and the residue was recrystallized from hydrous ethanol to obtain 1.06 g of 8-hydroxy-5,7-dimethyl-9-(1-pyrrolidinyl)-1,2,3,4,4a,9a-hexahydrofluorene having a melting point of 96°-97° C. and of colorless prism-like crystal.

The following compounds were prepared in the same manner as in Examples 20 and 21 using suitable starting materials.

EXAMPLES 168-178

By procedures similar to those described in Examples 20 and 21 and by using suitable starting materials, there were prepared compounds of Examples 168-178 as shown in the following Table 14.

TABLE 14

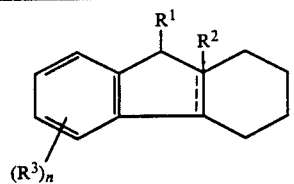

| Example No. | R³ | n | R¹ | R² | Bonding between 4a- and 9a- positions | Crystal form (Recrystallization solvent) | Melting point (°C.) (Salt form) |
|---|---|---|---|---|---|---|---|
| 168 | 5,8-diCH₃ 8-OCH₃ | 3 | —(CH₂)₂NH—CH₂—[pyrrolidine N-C₂H₅] | — | Double bond | Light yellow powdery crystals* | 153–154 (Oxalate) |
| 169 | 5,7-diCH₃ 8-OCH₃ | 3 | —(CH₂)₂NH(CH₂)₂NHCOCH₃ | — | Double bond | Colorless granular crystals (Diisopropyl ether-ethanol)* | 173–175 (dec.) (HCl) |
| 170 | 5,7-diCH₃ 8-OCH₃ | 3 | —(CH₂)₂—N((CH₂)₂OH)((CH₂)₂OH) | — | Double bond | Light yellow prism-like crystals (Ethanol)* | 160–163 (HCl) |
| 171 | 5,7-diCH₃ 8-OCH₃ | 3 | —(CH₂)₂NHCH₂CH(CH₂OH)(OH) | — | Double bond | Light yellow needle-like crystals (Ethanol)* | 188–191 (Oxalate) |
| 172 | 5,8-diCH₃ 8-OCH₃ | 3 | —(CH₂)₂NH(CH₂)₃OH | — | Double bond | White powdery substance (Ethanol)* | 200–201 (Oxalate) |
| 173 | 5,8-diCH₃ 8-OCH₃ | 3 | —(CH₂)₂NH(CH₂)₄OH | — | Double bond | White powdery substance (Ethanol)* | 182–183 (Oxalate) |
| 174 | 5,7-diCH₃ 8-OCH₃ | 3 | —(CH₂)₂—N(morpholine)O | — | Double bond | Colorless flake-like crystals (Ethanol)* | 222–226 (Oxalate) |
| 175 | 5,8-diCH₃ 8-OCH₃ | 3 | —(CH₂)₂NH—CH₂—[furan] | — | Double bond | Colorless flake-like crystals (Ethanol)* | 223–228 |
| 176 | 5-CH₃ 7-CH₂CH=CH₂ 8-OCH₃ | 3 | —N(CH₃)(CH₃) | H | Single bond | (*) | |
| 177 | 5-CH₃ 7-CH₂CH₂CH₃ 8-OH | 3 | —NHCH₃ | H | Single bond | (**) Isomer A Colorless needle-like crystals (Acetonitrile-ethanol) Isomer B | 178–180° C. (HCl) (—) |
| 178 | 5-CH₃ 7-CH₂CH=CH₂ 8-OCH₃ | 3 | —NHCH₃ | H | Single bond | Colorless powdery crystals (Acetonitrile) | 186–189 (dec.) (HCl) |

(*) Example 176: ¹H—NMR (CDCl₃) δ: (Free)
1.20–1.82 (m, 6H), 1.93–2.13 (m, 2H),
2.17–2.43 ([m, 10H, contains 2.25 (s, 3H), 2.30 (s, 6H)],
2.82 (m, 1H), 3.38 (d, J=6.5Hz, 2H), 3.73 (s, 3H), 4.08 (d, J=7Hz, 1H),
4.97–5.10 (m, 2H), 5.87–6.07 (m, 1H), 6.86 (s, 1H).

(**) Example 177: Isomer A:
¹H—NMR (CDCl₃) δ: (Free)
0.83–1.77 [m, 14H, contains (t, J=7Hz, 3H)], 2.25 (s, 3H),
2.33–2.63 [m, 7H, contains 2.47 (s, 3H)], 3.15 (m, 1H), 4.08 (m, 1H),
6.68 (s, 1H).

TABLE 14-continued

Isomer B:
$^1$H—NMR (CDCl$_3$) δ: (Free)
0.83-1.03 [m, 4H, contains 0.97 (t, J=7Hz, 3H)], 1.13-1.50 (m, 2H),
1.52-1.77 (m, 6H), 1.87-2.03 (m, 2H), 2.16 (s, 3H),
2.30-2.60 [m, 6H, contains 2.49 (s, 3H)], 2.92 (d, t, J=6Hz, 12Hz, 1H),
4.41 (d, J=10Hz), 6.75 (s, 1H).

1 NMR data of the compounds of Examples 168-175 are shown below.

Example 168
$^1$H—NMR (250 MHz) DMSO δ:
1.10 (3H, m), 1.70 (8H, m), 2.18 (3H, s),
2.37 (3H, s), 2.0-2.8 (8H, m),
2.8-3.4 (7H, m), 3.55 (1H, m),
3.72 (3H, s), 6.80 (1H, s).

Example 169
$^1$H—NMR (250 MHz) CDCl$_3$ δ:
1.75 (4H, m), 2.02 (3H, s), 2.23 (3H, s),
2.42 (3H, s), 2.15-3.1 (10H, m),
3.50 (1H, m), 3.57 (2H, m),
3.80 (3H, s), 6.82 (1H, s),
7.88 (1H, br), 8.99 (1H, br),
9.30 (1H, br).

Example 170
$^1$H—NMR (250 MHz) CDCl$_3$ δ:
1.77 (4H, m), 2.22 (3H, s), 2.43 (3H, s),
2.2-2.5 (4H, m), 2.4-2.85 (4H, m),
2.9-3.4 (4H, m), 3.56 (1H, m),
3.65-4.1 (4H, m), 3.77 (3H, s),
4.76 (2H, m), 6.83 (1H, s),
10.72 (1H, br).

Example 171
$^1$H—NMR (250 MHz) DMSO δ:
1.70 (4H, m), 2.18 (3H, s), 2.37 (3H, s),
2.1-2.8 (10H, m), 2.91 (1H, m),
3.33 (2H, m), 3.54 (1H, m), 3.60 (1H, m),
3.72 (3H, s), 6.80 (1H, s).

Example 172
$^1$H—NMR (250 MHz) DMSO δ:
1.71 (6H, m), 2.1-2.7 (8H, m),
2.19 (3H, s), 2.38 (3H, s),
2.84 (2H, m), 3.43 (2H, m),
3.56 (1H, m), 3.74 (3H, s), 6.81 (1H, s).

Example 173
$^1$H—NMR (250 MHz) DMSO δ:
1.3-1.6 (4H, m), 1.6-1.85 (4H, m),
2.18 (3H, s), 2.37 (3H, s),
2.1-2.55 (6H, m), 2.61 (2H, m),
2.77 (2H, m), 3.36 (2H, m), 3.56 (1H, m),
3.72 (3H, s), 6.81 (1H, s).

Example 174
$^1$H—NMR (250 MHz) DMSO δ:
1.74 (4H, m), 2.1-2.75 (8H, m),
2.18 (3H, s), 2.37 (3H, s), 2.85 (4H, m),
3.54 (1H, m), 3.68 (4H, m), 3.72 (3H, s),
6.79 (1H, s).

Example 175
$^1$H—NMR (250 MHz) DMSO δ:
1.69 (4H, m), 2.18 (3H, s),
2.37 (3H, s), 2.0-2.7 (8H, m),
3.54 (1H, m), 3.71 (1H, s),
4.10 (2H, s), 6.48 (2H, s),
6.80 (1H, s), 7.71 (1H, s).

EXAMPLE 179

By procedures similar to those described in Examples 20, 21, 53 and 54, and by using suitable starting materials, there were prepared compounds as follows:

o  8-Hydroxy-5,7-dimethyl-9-(piperidin-4-yl)methylamino-1,2,3,4,4a,9a-hexahydrofluorene
White powdery substance (from ethanol)
Melting point: 144°-146° C.

o  8-Hydroxy-5-methyl-7-(1-methyl-2-propenyl)-9-(1-benzylpiperidin-4-yl)amino-1,2,3,4,4a,9a-hexahydrofluorene
$^1$H-NMR CDCl$_3$): 0.9-1.95 (15H, m), 1.95-2.2 (2H, m), 2.24 (3H, s), 2.3-2.75 (2H, m), 2.85 (2H, m), 3.14 (1H, m), 3.51 (2H, s), 3.80 (1H, m), 4.31 (1H, m), 5.06 (1H, m), 6.06 (1H, m), 6.66 (1H, s), 7.31 (5H, m).

Pharmacological Tests

Pharmacological tests of hydrofluorene compounds of the present invention were conducted as follows.

(1) Test Compounds (1)  8-Hydroxy-5-methyl-7-(1-methyl-2-propenyl)-9-methylamino-1,2,3,4,4a,9a-hexahydrofluorene hydrochloride (Compound of Example 35)

(2)  8-Methoxy-5-methyl-7-(1-methyl-2-propenyl)-9-dimethylamino-1,2,3,4,4a,9a-hexahydrofluorene hydrochloride (Compound of Example 54)

(3)  8-Hydroxy-5,7-dimethyl-9-amino-1,2,3,4,4a,9a-hexahydrofluorene hydrochloride (Compound of Example 8)

(4)  8-Hydroxy-5-methyl-7-(2-propenyl)-9-ethylamino-1,2,3,4,4a,9a-hexahydrofluorene hydrochloride (Compound of Example 38)

(5)  8-Hydroxy-5-methyl-7-(1-phenyl-2-propenyl)-9-methylamino-1,2,3,4,4a,9a-hexahydrofluorene hydrochloride (Compound of Example 41)

(6)  8-Hydroxy-5-methyl-7-t-butyl-9-methylamino-1,2,3,4,4a,9a-hexahydrofluorene hydrochloride (Compound of Example 42)

(7) 8-Hydroxy-5-methyl-7-t-butyl-9-amino-1,2,3,4,4a,-9a-hexahydrofluorene hydrochloride (Compound of Example 9)
(8) 8-Hydroxy-5,7-dimethyl-9-n-octylamino-1,2,3,4,4a,-9a-hexahydrofluorene hydrochloride (Compound of Example 28)
(9) 5,7-Dimethyl-8-hydroxy-1,2,3,4,4a,9a-hexahydro-9-fluorene oxime isomer (A) (Compound of Example 1)
(10) 5,7-Dimethyl-8-hydroxy-9-allylamino-1,2,3,4,4a,-9a-hexahydrofluorene hydrochloride (Compound of Example 29)
(11) 5,7-Dimethyl-8-hydroxy-9-(1-ethyl-2-pyrrolidinyl)-methylamino-1,2,3,4,4a,9a-hexahydrofluorene isomer (A) (Compound of Example 21)
(12) 5,7-Dimethyl-8-hydroxy-9-(1-ethyl-2-pyrrolidinyl)-methylamino-1,2,3,4,4a,9a-hexahydrofluorene isomer (B) (Compound of Example 21)
(13) 5,7-Dimethyl-8-hydroxy-9-(1-benzyl-4-piperidinyl)amino-1,2,3,4,4a,9a-hexahydrofluorene (Compound of Example 46)
(14) 8-Methoxy-5-methyl-7-(1-methyl-2-propenyl)-9-methylamino-1,2,3,4,4a,9a-hexahydrofluorene hydrochloride (Compound of Example 37)
(15) 8-Hydroxy-5-methyl-7-t-butyl-9-ethylimino-1,2,3,4,4a,9a-hexahydrofluorene hydrochloride (Compound of Example 18)
(16) 8-Hydroxy-5-methyl-7-(1-methyl-2-propenyl)-9-(N-methyl-N-acetyl)amino-1,2,3,4,4a,9a-hexahydrofluorene (Compound of Example 57)
(17) 8-Hydroxy-5-methyl-7-t-butyl-9-methylimino-1,2,3,4,4a,9a-hexahydrofluorene (Compound of Example 17)
(18) 8-Hydroxy-5-methyl-7-t-butyl-9-d-chloroacetylamino 1,2,3,4,4a,9a-hexahydrofluorene (Compound of Example 61)
(19) 8-Hydroxy-5,7-dimethyl-9-ethylamino-1,2,3,4,4a,-9a-hexahydrofluorene (Compound of Example 25)
(20) 8-Hydroxy-5,7-dimethyl-9-n-propylamino-1,2,3,4,4a,9a-hexahydrofluorene hydrochloride (Compound of Example 26)
(21) 8-Hydroxy-5-methyl-9-methylimino-1,2,3,4,4a,9a-hexahydrofluorene (Compound of Example 15)
(22) 8-Hydroxy-5-methyl-7-sec-butyl-9-methylamino-1,2,2,4,4a,9a-hexahydrofluorene hydrochloride (Compound of Example 77)
(23) 8-Hydroxy-5-methyl-9-4-(3-methoxyphenyl)-1-piperazinyl acetylamino-1,2,3,4,4a,9a-hexahydrofluorene hydrochloride (Compound of Example 69)
(24) 8-Methoxy-5-methyl-7-bromo-9-dimethylamino-1,2,3,4,4a,9a-hexahydrofluorene hydrochloride (Compound of Example 78)
(25) 8-Hydroxy-5-methyl-7-t-butyl-9-(N-methyl-N-acetyl)amino-1,2,3,4,4a,9a-hexahydrofluorene (Compound of Example 85)
(26) 8-Hydroxy-5-methyl-7-(1-phenylpropyl)-9-methylamino-1,2,3,4,4a,9a-hexahydrofluorene hydrochloride (Compound of Example 79)
(27) 8-Hydroxy-5-methyl-7-(1-cyclohexylpropyl)-9-amino-1,2,3,4,4a,9a-hexahydrofluorene hydrochloride (Compound of example 13)
(28) 8-Hydroxy-5-methyl-7-(1-methyl-2-propenyl)-9-(N-methyl-N-dimethylaminoacetylamino)-1,2,3,4,4a,-9a-hexahydrofluorene hydrochloride (Compound of Example 146)
(29) 8-Hydroxy-5-methyl-7-acetylamino-9-(N-methyl-N-acetyl)-1,2,3,4,4a,9a-hexahydrofluorene (Compound of Example 147)
(30) 8-Hydroxy-5-methyl-7-acetylamino-9-methylamino-1,2,3,4,4a,9a-hexahydrofluorene (Compound of Example 119)
(31) 8-Methoxy-5-methyl-7-(2-cyclohexene-1-yl)-9-dimethylamino-1,2,3,4,4a,9a-hexahydrofluorene (Compound of Example 122)
(32) 8-Hydroxy-5-methoxy-7-(1-methyl-2-propenyl)-9-methylamino-1,2,3,4,4a,9a-hexahydrofluorene hydrochloride (Compound of Example 123)
(33) 8-Hydroxy-5,9a-dimethyl-7-tert-butyl-9-methylamino-1,2,3,,4a,9a-hexahydrofluorene (Compound of Example 124)
(34) 8-Hydroxy-5,9a-dimethyl-7-(1-methyl-2-propenyl)-9-(N-methyl-N-acetylamino)-1,2,3,4,4a,9a-hexahydrofluorene (Compound of Example 153)
(35) 8-Hydroxy-5,9a-dimethyl-7-(1-methyl-2-propenyl)-9-methylamino-1,2,3,4,4a,9a-hexahydrofluorene hydrochloride (Compound of Example 125)
(36) 8-Methoxy-5-methyl-7-cyclohexyl-9-dimethylamino-1,2,3,4,4a,9a-hexahydrofluorene hydrochloride (Compound of Example 126)
(37) 8-Hydroxy-5-methyl-7-cyclohexyl-9-methylamino-1,2,3,4,4a,9a-hexahydrofluorene (Compound of Example 127)
(38) 8-Hydroxy-5-methyl-7-(2-cyclohexene-1-yl)-9-methylamino-1,2,3,4,4a,9a-hexahydrofluorene (Compound of Example 128)
(39) 8-Hydroxy-5,7,9a-trimethyl-9-n-propylamino-1,2,3,4,4a,9a-hexahydrofluorene hydrochloride (Compound of Example 129)
(40) 8-Hydroxy-5-methyl-9-(N-methyl-N-acetylamino)-1,2,3,4,4a,9a-hexahydrofluorene (Compound of Example 154)
(41) 8-Hydroxy-5-fluoro-7-(1-methyl-2-propenyl)-9-(N-methyl-N-acetylamino)-1,2,3,4,4a,9a-hexahydrofluorene (Compound of Example 156)
(42) 8-Hydroxy-5-fluoro-7-(1-methyl-2-propenyl)-9-methylamino-1,2,3,4,4a,9a-hexahydrofluorene hydrochloride (Compound of Example 130)
(43) 8-Methoxy-5,7-dimethyl-9-(2-aminoethyl)-1,2,3,4-tetrahydrofluorene hydrochloride (Compound of Example 132)
(44) 8-Methoxy-5,7-dimethyl-9-[2-(methylamino)ethyl]-1,2,3,4-tetrahydrofluorene hydrochloride (Compound of Example 133)
(45) 8-Methoxy-5,7-dimethyl-9-[2-(dimethylamino)ethyl]-1,2,3,4-tetrahydrofluorene hydrochloride (Compound of Example 134)
(46) 8-Methoxy-5,7-dimethyl-9-{2-[4-(3-methylphenyl)-1-piperazinyl]ethyl}-1,2,3,4-tetrahydrofluorene hydrochloride (Compound of Example 135)
(47) 8-Methoxy-5,7-dimethyl-9-{2-[4-(3-methoxyphenyl)-1-piperazinyl]ether}-1,2,3,4-tetrahydrofluorene dihydrochloride (Compound of Example 136)
(48) 8-Methoxy-5,7-dimethyl-9-{2-[4-(3-chlorophenyl)-1-piperazinyl]ethyl}-1,2,3,4-tetrahydrofluorene dihydrochloride (Compound of Example 137)
(49) 8-Methoxy-5,7-dimethyl-9-[2-(4-methyl-1-piperazinyl)ethyl]-1,2,3,4-tetrahydrofluorene dihydrochloride (Compound of Example 138)
(50) 8-Methoxy-5,7-dimethyl-9-[2-(2-hydroxyethylamino)ethyl]-1,2,3,4-tetrahydrofluorene hydrochloride (Compound of Example 141)
(51) 8-Methoxy-5,7-dimethyl-9-[2-(1-pyrrolidinyl)ethyl]-1,2,3,4-tetradhyrofluorene hydrochloride (Compound of Example 143)

(52) 8-Methoxy-5-methyl-9-methylaminomethyl-1,2,3,4,4a,9a-hexahydrofluorene hydrochloride (Compound of Example 145)

(53) 8-Methoxy-5,7-dimethyl-9-{2-[(1-ethyl-2-pyrrolidynyl)methylamino]ethyl}-1,2,3,4-tetradhydrofluorene oxalate (Compound of Example 168)

(54) 8-Methoxy-5,7-dimethyl-9-[2-(2,3-dihydroxypropylamino)ethyl]-1,2,3,4-tetradhydrofluorene oxalate (Compound of Example 171)

(55) 8-Methoxy-5,7-dimethyl-9-[2-(4-hydroxybutylamino)ethyl]-1,2,3,4-tetradhyrofluorene oxalate (Compound of Example 173)

(56) 8-Methoxy-5,7-dimethyl-9-(2-morpholinoethyl)-1,2,3,4-tetradhyrofluorene oxalate (Compound of Example 174)

Pharmacological Test-I

Anti-chemical poisoning (potassium cyanide) test was conducted as follows:

A test solution containing each of the test compounds, in the concentration of 10 mg/ml, in 0.5%-gum arabi physiological saline was orally administered in the rate of 0.1 ml/10 g (of the body weight) to an ICR-strain male mouse. On the other hand, as to the control test, 0.5%-gum arabi physiological saline, without containing the test compound, was orally administered in the same rate of 0.1 ml/10 g (of the body weight) to another ICR-strain male mouse. One hour after the oral administration, 3 mg/kg of potassium cyanide was administered intravenously to each of the test mice. Survival time of each of the test mice was determined as a length of time between the intravenous administration and the complete arrest of breathing of each of the test mice. The data thus obtained were statistically treated by a method of Wilcoxon rank variable sum test.

The evaluation of the test was referred to as anti-potassium cyanide activity (%) and calculated by the following formula:

$$\text{Anti-potassium cyanide activity (\%)} = \frac{A}{B} \times 100$$

wherein

A: survival time of the mouse administered with test compound

B: survival time of the mouse administered without test compound.

The test results are shown in Table 15 as follows:

TABLE 15

| Test compound No. | Anti-potassium cyanide activity |
|---|---|
| 1 | 135 |
| 2 | 127 |
| 3 | 130 |
| 4 | 215 |
| 5 | 215 |
| 6 | 162 |
| 7 | 143 |
| 8 | 121 |
| 9 | 111 |
| 10 | 134 |
| 11 | 124 |
| 12 | 141 |
| 13 | 167 |
| 14 | 141 |
| 15 | 123 |

Pharmacological Test-II

Determination of choline transport rate was conducted as follows:

ICR-strain male mice of 4-week age were used as test animals, and four (4) mice were used as one test group.

A test suspension containing each of the test compounds, in the concentration of 10 mg/ml, in 0.5%-gum arabi physiological saline was orally administered in the rate of 0.1 ml/10 g (of the body weight) to the test mouse. One hour after the oral administration, the test mouse was killed by decapitation, and the brain was enucleated and the cerebral cortex containing the hippocampus was used as the tissue preparation in the test.

(1) Preparation of the cerebral synaprosome

By procedures as described in an article written by Simon, et al.: J. Neurochem., 26, pp. 909–922 (1976), the cerebral synaptosome was prepared. Thus, the cerebral cortex containing hippocampus was homogenized with 20 times amount of 0.32 M-sucrose solution and the homogenate was centrifuged at 1000 G for 10 minutes. The supernatant was further centrifuged at 17,000 G for 15 minutes. The sediment was suspended again with 0.32 M-sucrose solution so as to prepare the desired cerebral synaptosome for determination of Na-dependent HAChT (high-affinity choline transportation).

(2) Determination of HAChT

By procedures as described in an article written by Mantrone, et al.: Science, 213, pp. 579–580 (1981), the HAChT (high-affinity choline transportation) was determined.

0.1 Milliliter of the synaptosome was added to a buffer solution containing [$^3$H]-chloline (concentration: 0.5 M) and the final volume of this mixture was adjusted to 1 milliliter. The mixture was incubated at 30° C. for 4 minutes. The buffer solution used having the following formulation.

| Tris(hydroxymethyl)aminomethane | 40 mM |
|---|---|
| NaCl | 125 mM |
| KCl | 9.6 mM |
| MgSO$_4$ | 4.2 mM |
| CaCl$_2$ | 2.4 mM |
| Dextrose | 10 mM |

The reaction was stopped by cooling the mixture, and the mixture was filtered by using a glass fiber filter, the tissue thus remained on the glass fiber filter was then washed 3 times with 3 ml of chilled buffer solution having the above-mentioned formulation. The [$^3$H] remained on the glass fiber filter was measured by a liquid scintillation counter and the data thus obtained was referred to as the total uptake amount of [$^3$H]-choline.

On the other hand, the [$^3$H] count measured from the synaptosome which was incubated with Na-free buffer solution in which the Na in the above-mentioned buffer solution was substituted by the equivalent of sucrose was referred to as the non-specific uptake amount of [$^3$H]-choline.

The HAChT were measured as the total uptake amount and non-specific uptake amount and indicated as the amount of choline being uptook in the tissue within 4 minutes per 1 mg of protein (p mole/4 min./mg of protein).

The uptake amount of choline of control group in which each of the test mice was orally administeed with a 0.5%-gum arabi physiological saline in the rate of 0.1 ml/10 g (of the body weight) was referred to as 100%. The ratio of the uptake amount of choline of test group in which each of the test mice was orally administered with a test suspension containing each of the test compounds, in the concentration of 10 mg/ml, in 0.5%-gum arabi physiological saline in the same rate of 0.1 ml/10 g (of the body weight) to the uptake amount of choline of control group was calculated as ratio (%) of the uptake amount of choline.

The determination of the amount of protein was conducted by procedures as described in an article written by Lowry, et al.: J. Biol. Chem., 193, pp. 265-275, (1951).

The results are shown in Table 16 as follows.

TABLE 16

| Test compound No. | Uptake amount of choline (%) |
|---|---|
| 2 | 136 |
| 16 | 153 |
| 17 | 142 |
| 18 | 128 |
| 19 | 125 |
| 20 | 122 |
| 21 | 129 |
| 22 | 122 |
| 23 | 125 |
| 24 | 118 |
| 25 | 122 |
| 26 | 121 |
| 27 | 117 |
| 37 | 127 |
| 38 | 122 |
| 42 | 117 |

Pharmacological Test-III

Eight (8) directional radial maze test was conducted as follows:

(1) Test animals:

Wister-strain male rats (about 10 week-age) were used as the test animals. The test animals were feeded under restricted conditions during the test period so as to keep their body weight to about 85% of the body weight gained in free-feeding.

(2) Test apparatus:

The test apparatus is an eight (8) directional radial maze consisting of the central platform and 8 directional radial mazes which are connected and protruded from the central platform.

(3) Test procedures:

(1) Handling and acclimatization to the apparatus:

The test animal was placed in the apparatus for 5 minutes a day for handling the apparatus, and free exploring in the apparatus was allowed for 10 minutes a day for acclimatization to the apparatus which was repeated for 3 days.

(2) Training for study of radial maze exercise was conducted once (1 test run) a day. In conducting 1 test run, 1 pelet of feed was placed on the feed dish being located at the terminal of the all radial mazes. Then the rat was placed on the central platform and allowed to take the feed freely. When the rat took the all of 8 feeds, or 10 minutes laps of time, then the rat was taken out from the apparatus, which is referred to as 1 test run.

The action of rat entering any one of the radial mazes and takes the feed is referred to as "selection". Further, the action of rat in any one of 1 test run selecting any one of non-selected radial mazes is referred to as "correct selection". Among the first 8 selections, when 7 or more selections were correct selections which were continuously made in 5 test runs, such action of rat is referred to as "standard for learning". The training of rat was conducted to reach until such standard.

(3) Test compounds:

Each of the test compounds was administered orally 1 hour before the test. Further, scopolamine was administered subcutaneously 15 minutes before the test. Test for observing the selection reaction was conducted, thus the rat being administered each of the test compounds was placed in the apparatus by the procedures similar to those conducted in the training for study. An interval of a day for administration of test compound to another day for administration of test compound of the next test was kept at least 3 days or more, and during such intermission period, a confirmation test was conducted without administered any test compound so as to confirm the effects of the test compound administered in the previous test.

The test results are shown in Table 17 as follows.

TABLE 17

| Test compound No. | Dosage of test compound (mg/kg) | Dosage of scopolamine (mg/kg) | [Number of test rats which showed 7 or more correct corrections]/ [Total number of test rats] |
|---|---|---|---|
| Control | 0 | 0 | 8/8 |
| 2 | 0 | 0.5 | 3/8 |
|  | 10 | 0.5 | 5/8 |
|  | 0 | 0.5 | 5/8 |
|  | 30 | 0.5 | 8/8 |
| Control | 0 | 0 | 9/9 |
| 16 | 0 | 0.5 | 3/9 |
|  | 10 | 0.5 | 6/9 |
|  | 0 | 0.5 | 4/9 |
|  | 30 | 0.5 | 7/9 |
| Control | 0 | 0 | 9/9 |
| 19 | 0 | 0.5 | 3/9 |
|  | 10 | 0.5 | 5/9 |
|  | 0 | 0.5 | 5/9 |
|  | 30 | 0.5 | 7/9 |
| Control | 0 | 0 | 9/9 |
| 20 | 0 | 0 | 4/9 |
|  | 30 | 0.5 | 8/9 |

Pharmacological Test-IV

This test was conducted by procedures similar to those described in an article reported in "Arch. Int. Pharmacodyn., Pharmacodyn., Vol. 233, page 137, (1978)".

ICR-strain male mice (weighing 20 to 30 g) were used as the test animals. Four (4) mice were used as one test group, the mice were placed in a glass desciccator with which a stop valve was equipped. Inside pressure of the desiccator was reduced until 210 or 240 mm-Hg by sucking the air by using a vacuum pump, then the stop valve was closed.

Survival time of each of the test mice was determined as a length of time between the beginning of the vacuum pump operation and the arrest of breathing of the mouse.

Each of the test compounds was orally administered to the mouse 15 minutes before the beginning of the vacuum pump operation.

The survival time of the mouse of the reference group was referred to as 100, and the ratio of the survival time of the mouse of the test group was calculated by the following formula and obtained the survival ratio (%):

$$\text{Survival ratio (\%)} = \frac{[\text{Survival time of the mouse administered with test compound}]}{[\text{Survival time of the mouse of the reference group}]} \times 100$$

The test results are shown in Table 18 as follows:

TABLE 18

| Test compound No. | Dosage (mg/kg) | Survival ratio (%) |
|---|---|---|
| 28 | 100 | 134 |
| 29 | 100 | 138 |
| 30 | 100 | 131 |
| 31 | 100 | 168 |
| 33 | 100 | 151 |
| 34 | 100 | 170.9 |
| 35 | 100 | 146 |
| 38 | 100 | 139 |
| 39 | 100 | 118 |
| 40 | 100 | 119 |
| 41 | 100 | 110 |
| 42 | 100 | 122 |
| 43 | 100 | 110 |
| 44 | 100 | 144 |
| 45 | 100 | 125 |
| 46 | 100 | 163.7 |
| 47 | 100 | 145.2 |
| 48 | 100 | 143.0 |
| 49 | 100 | 115.7 |
| 50 | 100 | 179.3 |
| 51 | 100 | 110.6 |
| 52 | 100 | 154.0 |
| 53 | 100 | 111 |
| 54 | 100 | 113 |
| 55 | 100 | 127 |
| 56 | 100 | 131 |

Pharmacological Test-V

Acetylcholine release test was conducted as follows.

By using a tissue chopper, a slice (3×0.3×0.3 mm in size) of the prosencephalon of mouse was prepared. The slice (containing 5 to 7 mg of protein) was proincubated with a test compound in 1.8 ml of Krebs-Ringer bicarbonate buffer solution (containing 10 μM of choline and 1 mM of ascorbic acid) under an atmosphere of a mixed gas of 95% $O_2$—5% $CO_2$ at 37° C. for 15 minutes. Then 0.1 ml of eserine (the final concentration: 10 μM) as the cholinesterase inhibitor and 0.1 mM of potassium chloride (the final concentration: 25 mM) were added thereto. The whole mixture was further incubated at 37° C. for 20 minutes. Then the reaction was stopped at 40° C., and the reaction mixture was centrifuged at 3,000 rpm for 5 minutes at 4° C. To the supernatant was added 0.2 ml of 1 M-perchoric acid (containing 0.1%-EDTA-2Na), then to the precipitate thus obtained was added 2 ml of 0.1 M-perchloric acid (containing 0.01%-EDTA-2Na), and the mixture was homogenized. To each of the all samples was added 5 nMol of ethylhomocholine as the internal standard substance (i.s.), then the mixture was centrifuged at 3,000 rpm for 10 minutes. 0.2 Milliliter of the supernatant thus obtained was neutralized with 50 microliters of 250 mM-sodium phosphate, then purified by using Dowex 1×4 column (Cl−, 0.25 ml). The eluate and washing liquor were collected and separated and determined qualitatively the acetylcholine and ethylhomocholine respectively by means of a high permance liquid phase chromatography. A column for removing eserine, a column for separation as well as a column for the enzyme were all products manufactures by BAS Co., Ltd. (Tokyo, Japan). As to the phase transferring agent, 50 mM-sodium phosphate buffer solution (pH 8.3, containing 40 M of sodium actanesulfonate) was used.

The amount of the protein in the slice was determined by procedures according to Lowry's method [0. H. Lowery, N. J. Rosebrough, A. L. Farr and R. J. Randall: J. Biol. Chem., 193, pp. 265–275 (1951)].

The amount of acetylcholine (nMol/mg of protein) released in the buffer solution and the amount of acetylcholine (nMol/mg of protein) in the slice were referred to as percentage (%) to those of obtained in the control group, respectively.

$$\text{Amount of acetylcholine released in the buffer solution (\%)} = \frac{[\text{Amount of acetylcholine (nMol/mg of protein) in buffer solution treated with test compound}]}{[\text{Amount of acetylcholine (nMol/mg of protein) in buffer solution of control group}]} \times 100$$

$$\text{Amount of acetylcholine in the slice (\%)} = \frac{[\text{Amount of acetylcholine (nMol/mg of protein) in slice treated with test compound}]}{[\text{Amount of acetylcholine (nMol/mg of protein) in slice of control group}]} \times 100$$

The test results are shown in Table 19 as follows:

TABLE 19

| Test compound No. | Dosage (M) | Amount of acetylcholine released in the buffer solution (%) | Amount of acetylcholine contained in the slice (%) |
|---|---|---|---|
| 32 | 100 | 116 | 99 |
| 33 | 100 | 116 | 83 |
| 36 | 100 | 174 | 48 |
| 37 | 100 | 159 | 83 |
| 38 | 100 | 217 | 80 |
| 39 | 100 | 143 | 80 |
| 42 | 100 | 149 | 73 |
| 45 | 100 | 117 | 70 |
| 51 | 100 | 125 | 55 |

Examples of pharmaceutical preparations of hydrofluorene derivative according to the present invention are shown below:

| | |
|---|---|
| 5,7-Dimethyl-8-hydroxy-9-amino-1,2,3,4,4a,9a-hexahydrofluorene | 200 mg |
| Glucose | 250 mg |
| Distilled water for injection | q.s. |
| Total volume | 5 ml. |

5,7-Dimethyl-8-hydroxy-9-amino-1,2,3,4,4a,9a-hexahydrofluorene and glucose were dissolved in an adequate volume of distilled water for injection, then the total volume of the injection solution was adjusted to 5 ml and the solution was filled in an ampule of 5 ml volume. After the air in the filled ampule was replaced with nitrogen gas, the ampule was sterilized with steam under pressure at 121° C. for 15 minutes to obtain the injection preparation having the above-mentioned formulation.

| Pharmaceutical preparation - 2 (Tables preparation) | |
| --- | --- |
| 5-Methyl-7-allyl-8-hydroxy-9-ethylamino-1,2,3,4,4a,9a-hexahydrofluorene hydrochloride | 100 g |
| Avicel (a trademark for microcrystalline cellulose, manufactured by Asahi Chemical Industry Co., Ltd.) | 40 g |
| Corn starch | 30 g |
| Magnesium stearate | 2 g |
| TC-5 (a trademark for hydroxypropyl methylcellulose, manufactured by The Shin-Etsu Chemical Co., Ltd.) | 10 g |
| Polyethylene glycol-6000 | 3 g |
| Castor oil | 40 g |
| Methanol | 40 g |

5-Methyl-7-allyl-8-hydroxy-9-ethylamino-1,2,3,4,4a,9a-hexahydrofluorene hydrochloride, Avicel, corn starch and magnesium stearate were admixed together and ground, then the mixture obtained was shaped into tablets by using a tablet machine (having 10 mm in diameter). The tablets obtained were coated with a film coating consisting of TC-5, polyethylene glycol-6000, castor oil and methanol to prepare the film coated tablets having the above-mentioned formulation.

| Pharmaceutical preparation - 3 (Tablets preparation) | |
| --- | --- |
| 5-Methyl-7-(1-methyl-2-propenyl)-8-hydroxy-9-(N-methyl-N-acetyl)amino-1,2,3,4,4a,9a-hexahydrofluorene | 5 mg |
| Starch | 132 mg |
| Magnesium stearate | 18 mg |
| Lactose | 45 mg |
| | 200 mg |

By using an usual procedure, tablets having the above-mentioned formulation were prepared.

We claim:

1. A hydrofluorene compound or salt thereof of the formula

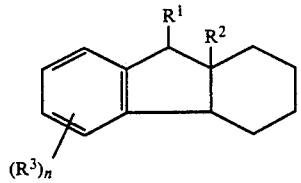

wherein $R^1$ is a group of the formula

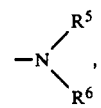

wherein $R^5$ and $R^6$ are each the same or different, and are each a hydrogen atom, an unsubstituted $C_1$–$C_8$ alkyl group, an unsubstituted $C_1$–$C_6$ alkanoyl group or a substituted $C_1$–$C_6$ alkanoyl group having halogen atoms as substituents; $R^2$ is a hydrogen atom; $R^3$ is a $C_1$–$C_6$ alkyl group, a $C_2$–$C_6$ alkenyl group, a hydroxy group, a halogen atom, a $C_3$–$C_8$ cycloalkyl group, a $C_3$–$C_8$ cycloalkenyl group having one double bond in the cycloalkyl ring, or a $C_1$–$C_6$ alkoxy group; n is an integer of 2 or 3; and the substituted position of $R^3$ is at the 5-, 7- or/and 8-positions in the hydrofluorene skeleton.

2. A pharmaceutical composition for improving anoxemic and hypoxic symptoms and syndromes comprising an effective amount of a hydrofluorene compound or salt thereof of claim 1 as the active ingredient and a pharmaceutically acceptable carrier.

3. A cholinergic nerve system activating composition comprising an effective amount of a hydrofluorene compound of salt thereof of claim 1 as the active ingredient and a pharmaceutical acceptable carrier.

4. An anti-oxidizing composition comprising an effective amount of a hydrofluorene compound or salt thereof of claim 1 as the active ingredient and a pharmaceutically acceptable carrier.

5. 5-Methyl-7-(1-methyl-2-propenyl)-8-methoxy-9-dimethylamino-1,2,3,4,4a,9a-hexahydrofluorene.

6. 5,7-Dimethyl-8-hydroxy-9-n-propylamino-1,2,3,4,4a,9a-hexahydrofluorene.

7. 5-Methyl-7-cyclohexyl-8-methoxy-9-dimethylamino-1,2,3,4,4a,9a-hexahydrofluorene.

8. 5-Methyl-7-(2-cyclohexen-1-yl)-8-hydroxy-9-methylamino-1,2,3,4,4a,9a-hexahydrofluorene.

9. 5-Fluoro-7-(1-methyl-2-propenyl)-8-hydorxy-9-methylamino-1,2,3,4,4a,9a-hexahydrofluorene.

10. 5-Methoxy-7-(1-methyl-2-propenyl)-8-hydroxy-9-methylamino-1,2,3,4,4a,9a-hexahydrofluorene.

11. 5-Methyl-7-bromo-8-methoxy-9-dimethylamino-1,2,3,4,4a,9a-hexahydrofluorene.

* * * * *